United States Patent
Chen et al.

(10) Patent No.: US 6,183,777 B1
(45) Date of Patent: *Feb. 6, 2001

(54) CONTROLLED RELEASE TACRINE DOSAGE FORM

(75) Inventors: Pao-Nien Chen; Chuan-Ming Lai; Shu-Jian Liu; Fan-Jung Liu; Shu-Bin Lu, all of Taipei (TW)

(73) Assignee: Development Center for Biotechnology, Taipei (TW)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/006,856

(22) Filed: Jan. 14, 1998

(30) Foreign Application Priority Data

Oct. 23, 1997 (CN) .................................................. 86115712

(51) Int. Cl.[7] .................................. A61K 9/24; A61K 9/36
(52) U.S. Cl. ........................... 424/472; 424/470; 424/480
(58) Field of Search .................. 424/472, 470, 424/473, 480

(56) References Cited

U.S. PATENT DOCUMENTS 5,576,022   11/1996   Yang et al. ............................ 424/472

FOREIGN PATENT DOCUMENTS

| 0 327 086 | 8/1989 | (EP) . |
| 95/03052 | 2/1995 | (WO) . |
| 95/14460 | 6/1995 | (WO) . |

Primary Examiner—Thurman K. Page
Assistant Examiner—Todd D Ware
(74) Attorney, Agent, or Firm—McDonnell Boehnen Hulbert & Berghoff

(57) ABSTRACT

Disclosed is a controlled release tacrine dosage form, which comprises:

(a) a core;
(b) an inner active layer comprising tacrine and a binder;
(c) a release-controlling layer comprising one or more release-controlling-film-forming polymer; and
(d) an active overcoat comprising tacrine and a binder.

Also disclosed is a process for preparing the controlled release dosage form.

22 Claims, 43 Drawing Sheets

CONTROLLED RELEASE TACRINE DOSAGE FORM

FIELD OF THE INVENTION

The invention relates to a controlled release tacrine dosage form and the preparation process thereof.

BACKGROUND OF THE INVENTION

Alzheimer's Disease (AD) is a progressive form of presenile neuropathy which causes chronic symptoms of serious neurodegeneration, and which is prone to progress to dementia. The recognition and intelligence functions of AD patients are seriously destroyed. The disease is the main cause of adult dementia and it is estimated that about 2.5 million individuals are infected with such disease in the United States and Canada. With the growth of senile population, it is expected that the impact of AD on public health will continuously increase. Accordingly, the development of effective medicines for AD therapy is in urgent need.

Tacrine, also known as 1,2,3,4-tetrahydro-9-acridinamine hydrochloride (THA), is a reversible acetyl cholinesterase inhibitor which may increase cerebral acetyl choline concentration, in particular in the cerebral cortex, by counteracting the destruction of acetyl choline by acetyl cholinesterase. Tacrine has been approved by U.S. Food and Drug Administration (FDA) for use in AD therapy in 1993, and is the only agent for treating mild to medium AD. It can significantly improve the memory and recognition of patients.

Tacrine has also been used as the analgesic for end-staged cancers, myasthenia gravis, tricyclic anti-depressive agent toxication and tardive dyskinesia.

It is known that tacrine may cause reversible hepatoxicity and many adverse effects, e.g. gastro-intestinal side effects, such as nausea, vomiting, diarrhea, dyspepsia and loss of appetite; kinetic ataxia of voluntary muscles and myalgia; sweating and bradycardia induced by overexcitement of vagus nerues.

The conventional preparations of tacrine should be administered four times a day. The compliance to senile people is therefore poor. Moreover, the pharmacokinetics of tacrine reveal that the oral bioavailability of tacrine may significantly vary in different individuals, and patients should experience a dosage adjustment period.

Accordingly, it is desired in the art to develop controlled release dosage forms of tacrine in order for maintaining stable concentration of the medicine in blood and brain to lower side effects, and for reducing the administration frequency to increase the compliance of the medicine, in particular to senile people.

U.S. Pat. No. 5,576,022 discloses a controlled release tacrine drug delivery system comprising immediate release pellets and sustained release pellets. The immediate release pellets are formed by coating non-pareil seeds with a coating comprising tacrine and a binder, and then with a coating comprising a sealing agent and a plasticizing agent. The sustained release pellets are formed by coating the immediate release pellets with a sustained release coating comprising a water insoluble polymer, a water soluble polymer and a second plasticizing agent.

The delivery system of the above patent may control the release of tacrine. However, as the sustained release pellets are multilayered, the preparation procedures are complex. In addition, as the size of the immediate pellets and the sustained release pellets are different, it would be inconvenient to fill them into capsules.

SUMMARY OF THE INVENTION

Accordingly, the object of the invention is to provide a controlled release tacrine dosage form comprising a single type of pellets.

DETAILED DESCRIPTION OF THE INVENTION

Figure 1:
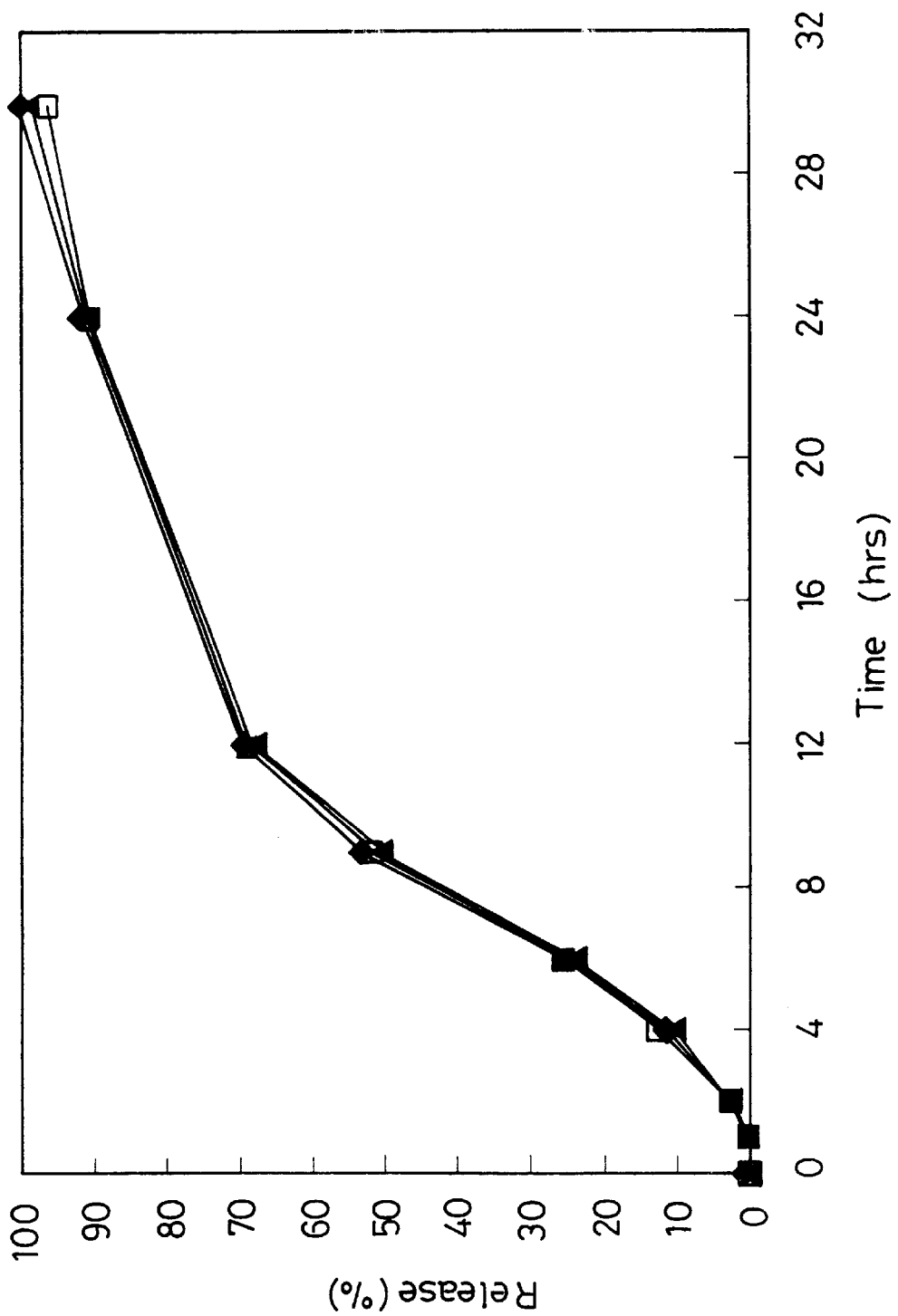
FIG. 1 depicts the dissolution curves of release-controlling-film coated pellets F-1 in $H_2O$.

It has been surprisingly found that pellets which release controlled amount of tacrine can be prepared by forming a release-controlling film on tacrine-coated pellets, and then coating thereon a second tacrine coating.

Accordingly, in the first aspect of the invention, there is provided a controlled release tacrine dosage form composed of single type of pellets, said dosage form comprising:

(a) a core;

(b) an inner active layer comprising tacrine and a binder;

(c) a release-controlling layer comprising one or more release-controlling film-forming polymer; and (d) an active overcoat comprising tacrine and a binder.

The first part of the controlled release dosage form of the invention is a core which serves as the basis for proceeding layer-coatings.

The term "core" used herein refers to any inner cores which are known in the art to be suitable for use in pharmaceutical coating technology, e.g. granules or beads made of sugars, sugar alcohols (such as sucrose, lactose, mannitol and xylitol), celluloses and starch which do not chemically react with pharmacologically active substances. For instance, Nu-pareil seeds available from Ingrient Technology, U.S.A. can be conveniently used in the invention.

The second part of the controlled release dosage form in accordance with the invention is an active inner layer coated on the core. The layer comprising the active ingredient, i.e. tacrine, and a binder serves as the reservoir for continuously releasing tacrine.

The term "tacrine" used herein refers to any tacrine forms known in the art that provide pharmacologically active 1,2,3,4-tetrahydro-9-acridinamine. It may be in the form of a free tacrine or the pharmaceutically acceptable salts, solvates or hydrates thereof. In one embodiment of the invention, the tacrine form used is tacrine hydrochloride monohydrate.

The amount of tacrine contained in the inner active layer of the controlled release dosage form of the invention may vary depending on the subject to apply the dosage form to, the recommended dosage amount and the rest components in the controlled release dosage form of the invention. The amount should be sufficient to allow the controlled release dosage form of the invention to continuously release therapeutically effective amount of tacrine for at least 24 hours. In general, tacrine comprises about 10 to 70% by weight of the inner active layer and core of the controlled release dosage form of the invention, preferably about 20 to 60%, more preferably 25 to 45%, and most preferably 28 to 38%.

The term "binder" used herein refers to a compound that exerts a physicochemical attractive force between molecules. Binders suitable for use in the invention include, but not limited to, polyvinylpyrrolidone, acacia, gelatin, glucose, guar gum, pregelatinized starch, sodium alginate, cellulose derivatives, and the like, and mixtures thereof.

Preferably, the binder used in the invention is a cellulose derivative, e.g. ethylcellulose, hydroxypropylcellulose, hydroxypropylmethylcellulose, methylcellulose, sodium carboxymethylcellulose, and the like, and mixtures thereof. Most preferably, the binder is hydroxypropylmethylcellulose.

The amount of the binder in the inner active layer of the invention should be sufficient to effectively bind tacrine to the core. The amount may vary depending on the desired release effect, and the species of the core, the binder, and the rest components in the inner active layer and the components of the release-controlling layer. In general, the binder comprises about 0.1 to 30% by weight of the active inner layer, preferably about 1 to 25%, more preferably about 2 to 20%, and most preferably 3 to 15%.

Typically, the weight ratio of the core to the inner active layer of the controlled release dosage form of the invention is in the range from about 3:7 to about 9:1, preferably about 4:6 to about 8:2, and most preferably about 5:5 to about 7:3.

The third part of the controlled release dosage form of the invention is a release-controlling layer comprising one or more release-controlling-film forming polymer. The layer is coated on the active inner layer to control the active ingredient contained therein, i.e. tacrine, to release in an desired amount.

The "release-controlling-film-forming polymer" used herein refers to a polymer that forms a film on the inner active layer comprising tacrine to control said active ingredient to be released in a suitable amount. The polymer may be any film-forming polymer that is conventionally used in the art for preparing controlled release dosage forms. Examples of the polymer include, but not limited to, water insoluble polymers, water soluble polymers, enteric polymers, and the like, and mixtures thereof.

Water insoluble polymers suitable for use in the invention include, but not limited to, cellulose derivatives, such as ethylcellulose; acrylic polymers, such as polyacrylamide, polyacrylic dextrin, polyalkylcyanoacrylates, polymethylmethacrylates and methacrylic resins; polyvinyl acetate; polyvinyl chloride; polyethylene; and the like; and mixtures thereof. Preferably, the water insoluble polymer used in the invention is ethylcellulose.

In the invention, the water insoluble polymer comprises about 40 to 95% by weight of the release-controlling layer, preferably about 50 to 85%, and most preferably about 65 to 80%.

Water soluble polymers suitable for use in the invention include, but not limited to, hydroxycellulose, hydroxypropylmethylcellulose, carboxymethylcellulose, and the like, and mixtures thereof. Preferably, the water soluble polymer used in the invention is hydroxypropylcellulose or hydroxypropylmethylcellulose. More preferably, the polymer is hydroxypropylmethylcellulose.

In the invention, the water soluble polymer comprises about 0 to 50% by weight of the release-controlling layer, preferably about 10 to 40%, and most preferably about 15 to 30%.

Enteric polymers suitable for use in the invention include, but not limited to, cellulose acetate phthalate, hydroxypropylmethylcellulose phthalate, hydroxypropylmethylcellulose acetate succinate, carboxymethylethylcellulose, styrene acrylic copolymers, methacrylic copolymers, maleic anhydride copolymers, shellac, and the like, and mixtures thereof. Preferably, the enteric polymer used in the invention is shellac.

In accordance with the invention, the release-controlling layer may comprise one or more the above described film-forming polymer. For instance, the water soluble polymer may be used alone. In one embodiment of the invention, ethylcellulose is used alone. The water soluble polymer may also be used in combination with a water insoluble polymer. In other embodiments of the invention, ethylcellulose is used in combination with hydroxypropylcellulose or hydroxypropylmethylcellulose. In addition, the enteric polymer may also be used alone. In a firer embodiment of the invention, shellac is used alone. Furthermore, it is possible to use two polyacrylates. A still further embodiment of the invention uses the combination of acrylic acid and a methacrylate polymer.

The amount of release-controlling-film-forming polymer in the controlled release dosage form of the invention should be sufficient to effectively control tacrine to be released in a desired amount. Preferably, the amount is effective to allow the controlled release dosage form of the invention to release therapeutically effective amount of tacrine for at least 24 hours after administration.

The release-controlling layer of the controlled release dosage form of the invention may further comprise one or more plasticizing agent.

The "plasticizing agent" used herein refers to any organic molecule capable of increasing the flexibility and toughness of final products by internally modifying or solvating polymer molecules. Plasticizing agents suitable for use in the invention include, but not limited to, phthalates, such as dibutyl phthalate; adipates; sebacates, such as dibutyl sebacate; ethylene glycol; polyethylene glycol and their derivatives; tricresyl phosphate; castor oil; citrates, such as triethyl citrate, tributyl citrate, acetyl tributyl citrate; triacetin; acetylated mono-, di- and triglycerides; and the like; and mixtures thereof. Preferably, the plasticizing agent used in the invention is selected from the group consisting of dibutyl phthalate, dibutyl sebacate and triethyl citrate.

In general, the plasticizing agent used in the invention comprises about 1 to 15% by weight of the release-controlling layer of the invention, preferably about 1.5 to 20%, and more preferably about 2 to 15%.

The fourth part of the controlled release dosage form of the invention is an active overcoat coated on the release-controlling layer. Said overcoat comprises tacrine and a binder, and provides an impulse of tacrine upon administration of the dosage form.

The amount of tacrine contained in the active overcoat of the controlled release dosage form of the invention may vary depending on the subject to apply the dosage form to, the recommended dosage amount and the rest components in the controlled release dosage form of the invention. The amount should be sufficient to allow the controlled release dosage form of the invention to release therapeutically effective amount of tacrine upon administration. In general, tacrine comprises about 55 to 99% by weight of the active overcoat, preferably about 60 to 98%, more preferably 65 to 97%, and most preferably 70–95%.

Any binder that is suitable for use in the active inner layer of the controlled release dosage form of the invention is suitable for use in the active overcoat. The amount of the binder in the active overcoat should be sufficient to bind tacrine to the release-controlling layer and may vary depending on the desired release effect, the species of the binder and the components in the release-controlling layer and the rest components in the active overcoat. In general, the binder comprises about 1 to 45% by weight of the active overcoat, preferably about 2 to 40%, more preferably 3 to 35%, and most preferably 5 to 30%.

The controlled release dosage form of the invention is constituted as stated above and can effectively release therapeutically effective amount of tacrine upon administration and continue the release for at least 24 hours. In general, to achieve the effect of immediate and continuous release of therapeutically effective amount of tacrine, the weight ratio of the tacrine component in the active inner layer to the active overcoat is in the range about 12:1 to about 1:1, preferably about 10:1 to about 3:1, and most preferably about 8:1 to 5:1.

The weight percentage of the core, the active inner layer, the release-controlling layer and the active overcoat in the controlled release dosage form of the invention may vary depending on the desired release effect. Typically, the four parts may comprise 42–62%, 25–45%, 3.5–13.5% and 2.5–6.5% by weight of the dosage form, respectively. In one embodiment of the invention, the four parts comprise 52%, 35%, 8.5% and 4.5% by weight of the dosage form, respectively.

In another aspect of the invention, there is provided a process for preparing a controlled release tacrine dosage form, which comprises:

(a) coating a suitable core with a mixture of tacrine and a binder to obtain a coated pellet;

(b) further coating the pellet obtained in step (a) with a release-controlling-film-forming polymer or a mixture thereof; and (c) further coating the pellet obtained in step (b) with a mixture of tacrine and a binder.

The components in each layer of the controlled release dosage form of the invention can be formulated to coating solutions with a suitable solvent or solvent system and then used to coat the core or the resultant pellets. For instance, the coating solutions can be formulated with water, an organic solvent or a mixture of organic solvents. Suitable organic solvents are those customarily used in the art, e.g. alcohols, such as ethanol, propanol or isopropanol; ketones such as acetone; and hydrocarbon chloride, such as methylene chloride. A mixture of water and an organic solvent of suitable ratios may also be used, e.g. a 3:7 to 7:3 mixture.

To facilitate the processing, one or more conventional pharmaceutically acceptable excipient and additive can be added to the coating solutions of active inner layer, release-controlling layer, and active overcoat, e.g. anti-foam agents, fillers, coloring agents, flavoring agents, perfumes, sweetening agents, surface active agents, lubricants, stabilizing agents, anti-tacking agents, and the like, and mixtures thereof.

For instance, one or more anti-tacking agent can be used in the coating solution to uniformly disperse the components. Anti-tacking agents suitable for use in the invention are those customarily used in the art, which include, but not limited to, polymeric electrolytes, condensed silicates, polyphosphates, xylin derivatives, such as aluminum stearate, aluminum laurate, magnesium stearate, calcium stearate, zinc stearate, talc, kaolin, fumed silica, and the like, and mixtures thereof. Preferably, the anti-tacking agent is talc or silica, which also acts as a light-barrier.

The dosage form of the present invention may be prepared using standard techniques and equipment known to those skilled in the art. The core may be prepared by suspension layering, powder layering, or extrusion/spheronization techniques, or other standard procedures, using standard techniques and equipment known to those skilled in the art. The core and pellets may be coated by fluid-bed coating, pan coating, or other standard coating procedures using standard techniques and equipment known to those skilled in the art. The exact conditions for forming and coating pellets will vary with the particular apparatus selected and are readily determined by those skilled in the art without the need for undue experimentation. Fluid-bed coating and pan coating are well known in the arts and therefore the selection of the specific apparatus will be apparent to the artisan.

The invention is further illustrated in the following examples, which, however, are not limitations of the invention.

In the following examples, the tacrine form used is tacrine hydrochloride monohydrate commercially available from Effechem Co. Italy; Pharmacoat 645 comprising hydroxypropylmethylcellulose is from Shin-Etsu Co., Japan; EC N-10 and EC D-30 comprising 27% ethylcellulose are from Aqualon Co., U.S.A.; methylene chloride HPLC grade is from Merck Co., German; Nu-pareil PG is from Ingrient Technology Co., U.S.A.; talc is from Nakarai Tesque Co., Japan; Surelease comprising ethylcellulose and fractionally distilled coconut oil is from Colorcon Co., U.S.A.; Aerosil comprises silica; triethyl citrate (TEC) is form Pfizer Co., Japan; hydroxypropylcellulose is form Shin-Etsu Co.; dibutyl phthalate (DBP) is from Nacalai Tesque Co.; Eudragit RS 30D, Eudragit RL 30D, Eudragit RS PO and Eudragit RL PO comprising acrylic acid/methacrylate copolymers are from Rohm Pharma Co., German; and Tween 80 comprising polysorbitol is from Merck Co., Germany.

EXAMPLE 1

Preparation of Inner Active Layer-Coated Pellets

The coating solution of active inner layer is of the following composition:

| | |
|---|---|
| Tacrine HCl | 36 g |
| Pharmacoat 645 | 24 g |
| Ethanol (EtOH) | 265 ml |
| H$_2$O | 265 ml |

Ethanol and water were mixed first. Pharmacoat 645 was dissolved in the mixture, and thereafter Tacrine HCl was added. The resultant mixture was heated to 50° C. to dissolve the components.

Nu-pareil seeds (60 g, 25–30 mesh) were coated with the above coating solution on Aerocoater Model Strea-1 (Aeromatic AG, Swiss) under the following conditions:

| | |
|---|---|
| Inlet: | 50° C. |
| Outlet: | 40° C. |
| Air: | 1.2 Bar |
| Air volume: | 100 M$^3$/hr |
| Spray: | 4 ml/min |

The seeds coated to a suitable diameter were dried at 50° C. for 30 min. to obtain inner active layer-coated pellets P-1 (yield: 109.8 g; efficiency: 83%).

Following the similar procedures, inner active layer-coated pellets P-2 to P-38 were prepared on Aerocoater Model Stea-1 or Model GPC G-3 (Glatt GmbH, Germany) fluid-bed granulator with the cores and coating solutions shown in Table 1 below:

TABLE 1

| No. | core | coating solution | | result | | conditions | |
|---|---|---|---|---|---|---|---|
| P-2 | 50 g Nupareil (25–30 mesh) | Tacrine Hcl Pharmacoat 645 EtOH H$_2$O | 40 g 12 g 210 ml 105 ml | efficiency yield | 82.9% 93.1 g | Aeromatic inlet outlet spray air air volume | 48° C. 38° C. 4 ml/min 1.2 bar 100 m$^3$/hr |
| P-3 | 1000 g Nupareil (25–30 mesh) | Tacrine Hcl Pharmacoat 645 EtOH H$_2$O | 36 g 24 g 300 ml 300 ml | acceptable | | Glatt inlet outlet spray air air volume | 52° C. 40° C. 20 ml/min 1.8 bar 0.35 bar |
| P-4 | 1000 g Nupareil (25–30 mesh) | Tacrine Hcl Pharmacoat 645 Talc EtOH H$_2$O | 40 g 40 g 15 g 300 ml 300 ml | acceptable | | Glatt inlet outlet spray air air volume | 52° C. 38° C. 25 ml/min 1.8 bar 95 m$^3$/hr |
| P-5 | 1000 g Nupareil (25–30 mesh) | Tacrine Hcl Pharmacoat 645 Talc EtOH H$_2$O | 40 g 20 g 20 g 250 ml 250 ml | acceptable | | Glatt inlet outlet spray air air volume | 52° C. 36° C. 30 ml/min 1.8 bar 2.35 bar |
| P-6 | 1000 g Nupareil (25–30 mesh) | Tacrine Hcl Pharmacoat 645 Talc EtOH H$_2$O | 40 g 20 g 20 g 200 ml 200 ml | acceptable | | Glatt inlet outlet spray air air volume | 52° C. 36° C. 30 ml/min 1.8 bar 0.35 bar |
| P-7 | 1000 g Nupareil (25–30 mesh) | Tacrine Hcl EtOH H$_2$O | 40 g 200 ml 100 ml | acceptable | | Glatt inlet outlet spray air air volume | 50° C. 36° C. 35 ml/min 1.8 bar 0.35 bar |
| P-8 | 1000 g Nupareil (25–30 mesh) | Tacrine Hcl Pharmacoat 645 EtOH H$_2$O | 40 g 10 g 200 ml 100 ml | acceptable | | Glatt inlet outlet spray air air volume | 50° C. 36° C. 35 ml/min 1.8 bar 0.35 bar |
| P-9 | 1000 g Nupareil (25–30 mesh) | Tacrine Hcl Pharmacoat 645 EtOH H$_2$O | 40 g 12 g 200 ml 100 ml | acceptable | | Glatt inlet outlet spray air air volume | 50° C. 37° C. 30 ml/min 1.8 bar 0.34 bar |
| P-10 | 50 g Nupareil (25–30 mesh) | Tacrine Hcl Pharmacoat 645 EtOH H$_2$O | 40 g 12 g 210 ml 105 ml | efficiency yield | 82.9% 93.1 g | Aeromatic inlet outlet spray air air volume | 48° C. 38° C. 4 ml/min 1.2 bar 100 m$^3$/hr |
| P-11 | 60 g Nupareil (25–30 mesh) | Tacrine Hcl Pharmacoat 645 EtOH H$_2$O | 48 g 14.4 g 252 ml 126 ml | efficiency yield | 85.3% 113.2 g | Aeromatic inlet outlet spray air air volume | 48° C. 34° C. 30 ml/min 1.2 bar 100 m$^3$/hr |
| P-12 | 630 g Nupareil (25–30 mesh) | Tacrine Hcl Pharmacoat 645 EtOH H$_2$O | 480 g 144 g 2520 ml 1260 ml | efficiency yield | 95.81% 1227.88 g | Glatt inlet outlet spray air air volume | 30° C. 34° C. 30 ml/min 1.8 bar 0.35 bar |
| P-13 | 650 g Nupareil (25–30 mesh) | Tacrine Hcl Pharmacoat 645 EtOH H$_2$O | 480 g 150 g 2500 ml 1250 ml | efficiency yield | 92.06% 1230 g | Glatt inlet outlet spray air air volume | 50° C. 34° C. 30 ml/min 1.8 bar 0.35 bar |

TABLE 1-continued

| No. | core | coating solution | | result | | conditions | |
|---|---|---|---|---|---|---|---|
| P-14 | 60 g Nupareil (25–30 mesh) | Tacrine Hcl Pharmacoat 645 H₂O | 48 g 15 g 250 ml | efficiency yield | 90.5% 117 g | Aeromatic inlet outlet spray air air volume | 55° C. 45° C. 3 ml/min 1.2 bar 100 m³/hr |
| P-15 | 60 g Nupareil (25–30 mesh) | Tacrine Hcl Pharmacoat 645 Talc H₂O | 48 g 15 g 1 g 250 ml | efficiency yield | 92% 118.71 g | Aeromatic inlet outlet spray air air volume | 55° C. 45° C. 3 ml/min 1.2 bar 100 m³/hr |
| P-16 | 70 g Nupareil (25–30 mesh) | Tacrine Hcl Pharmacoat 645 H₂O | 48 g 12 g 250 ml | efficiency yield | 91.2% 124.7 g | Aeromatic inlet outlet spray air air volume | 60° C. 44° C. 3.3 ml/min 1.3 bar 100 m³/hr |
| P-17 | 85.4 g Nupareil (25–30 mesh) | Tacrine Hcl Pharmacoat 645 EtOH H₂O | 60 g 12 g 180 ml 120 ml | efficiency yield | 85.5% 147 g | Aeromatic inlet outlet spray air air volume | 55° C. 43° C. 3.3 ml/min 1.2 bar 100 m³/hr |
| P-18 | 85 g Nupareil (25–30 mesh) | Tacrine Hcl Pharmacoat 645 EtOH H₂O | 60 g 12 g 150 ml 150 ml | efficiency yield | 86.4% 147.2 g | Aeromatic inlet outlet spray air air volume | 55° C. 43° C. 3–3.5 ml/min 1.2 bar 100 m³/hr |
| P-19 | 700 g Nupareil (25–30 mesh) | Tacrine Hcl Pharmacoat 645 EtOH H₂O | 480 g 96 g 1200 ml 1200 ml | efficiency yield | 93.5% 1238.5 g | Glatt inlet outlet spray air air volume | 55° C. 38° C. 30–33 ml/min 1.8 bar 0.35 bar |
| P-20 | 85 g Nupareil (25–30 mesh) | Tacrine Hcl Pharmacoat 645 EtOH H₂O | 60 g 11.25 g 150 ml 150 ml | efficiency yield | 87.16% 147.1 g | Aeromatic inlet outlet spray air air volume | 50° C. 40° C. 3 ml/min 1.2 bar 100 m³/hr |
| P-21 | 86 g Nupareil (25–30 mesh) | Tacrine Hcl Pharmacoat 645 EtOH H₂O | 60 g 10 g 130 ml 130 ml | efficiency yield | 85.71% 146 g | Aeromatic inlet outlet spray air air volume | 50° C. 40° C. 3 ml/min 1.2 bar 100 m³/hr |
| P-22 | 1210.5 g Nupareil (25–30 mesh) | Tacrine Hcl Pharmacoat 645 EtOH H₂O | 816 g 161.5 g 2125 ml 2125 ml | efficiency yield | 98.16% 2170 g | Glatt inlet outlet spray air air volume | 55° C. 33° C. 30–36 ml/min 1.8 bar 0.35 bar |
| P-23 | 1250.7 g Nupareil (25–30 mesh) | Tacrine Hcl Pharmacoat 645 EtOH H₂O | 816 g 161.5 g 2125 ml 2125 ml | efficiency yield | 95.58% 2185 g | Glatt inlet outlet spray air air volume | 55° C. 36° C. 30–36 ml/min 1.8 bar 0.35 bar |
| P-24 | 1450 g Nupareil (25–30 mesh) | Tacrine Hcl Pharmacoat 645 EtOH H₂O | 816 g 161.5 g 2125 ml 2125 ml | efficiency yield | 98.63% 2414.1 g | Glatt inlet outlet spray air air volume | 54° C. 34° C. 30–36 ml/min 1.8 bar 0.35 bar |
| P-25 | 1300 g Nupareil (25–30 mesh) | Tacrine Hcl Pharmacoat 645 EtOH H₂O | 816 g 161.5 g 2125 ml 2125 ml | efficiency yield | 99.0% 2270 g | Glatt inlet outlet spray air air volume | 54° C. 34° C. 30–36 ml/min 1.8 bar 0.35 bar |

TABLE 1-continued

| No. | core | coating solution | | result | | conditions | |
|---|---|---|---|---|---|---|---|
| P-26 | 1399 g Nupareil (25–30 mesh) | Tacrine Hcl Pharmacoat 645 EtOH H$_2$O | 816 g 161.5 g 2125 ml 2125 ml | efficiency yield | 96.256% 2339.9 g | Glatt inlet outlet spray air air volume | 54° C. 34° C. 30–36 ml/min 1.8 bar 0.35 bar |
| P-27 | 820 g Nupareil (25–30 mesh) | Tacrine Hcl Pharmacoat 645 H$_2$O | 480 g 95 g 2500 ml | efficiency yield | 99.0% 1389 g | Glatt inlet outlet spray air air volume | 60° C. 36° C. 30 ml/min 1.8 bar 0.35 bar |
| P-28 | 820 g Nupareil (25–30 mesh) | Tacrine Hcl Pharmacoat 645 H$_2$O | 480 g 95 g 2500 ml | efficiency yield | 99.0% 1338.9 g | Glatt inlet outlet spray air air volume | 60° C. 36° C. 30 ml/min 1.8 bar 0.35 bar |
| P-29 | 1399 g Nupareil (25–30 mesh) | Tacrine Hcl Pharmacoat 645 EtOH H$_2$O | 816 g 161.5 g 2125 ml 2125 ml | efficiency yield | 95.13% 2328.9 g | Glatt inlet outlet spray air air volume | 54° C. 34° C. 30–36 ml/min 1.8 bar 0.35 bar |
| P-30 | 1399 g Nupareil (25–30 mesh) | Tacrine Hcl Pharmacoat 645 EtOH H$_2$O | 816 g 161.5 g 2125 ml 2125 ml | efficiency yield | 95.33% 2330.8 g | Glatt inlet outlet spray air air volume | 54° C. 34° C. 30–36 ml/min 1.5 bar 0.35 bar |
| P-31 | 93 g Nupareil (25–30 mesh) | Tacrine Hcl Pharmacoat 645 Tween 80 EtOH H$_2$O | 61.5 g 11.875 g 4 g 166 ml 156 ml | efficiency yield | 86.46% 159.9 g | Aeromatic inlet outlet spray air air volume | 53° C. 41° C. 3–3.3 ml/min 1.2 bar 90 m$^3$/hr |
| P-32 | 90 g Nupareil (25–30 mesh) | Tacrine Hcl Pharmacoat 645 Tween 80 EtOH H$_2$O | 60 g 11.875 g 2 g 156 ml 156 ml | efficiency yield | 86.94% 154.23 g | Aeromatic inlet outlet spray air air volume | 53° C. 41° C. 3–3.3 ml/min 1.2 bar 90 m$^3$/hr |
| P-33 | 80 g Nupareil (25–30 mesh) | Tacrine Hcl Pharmacoat 645 Tween 80 EtOH H$_2$O | 60 g 11.875 g 0.2 g 156 ml 156 ml | efficiency yield | 86.94% 142.7 g | Glatt inlet outlet spray air air volume | 53° C. 41° C. 3–3.3 ml/min 1.2 bar 90 m$^3$/hr |
| P-34 | 1399 g Nupareil (25–30 mesh) | Tacrine Hcl Pharmacoat 645 EtOH H$_2$O | 816 g 161.5 g 2125 ml 2125 ml | efficiency yield | 95.95% 2336.9 g | Glatt inlet outlet spray air air volume | 54° C. 33° C. 30–36 ml/min 1.5 bar 0.35 bar |
| P-35 | 1399 g Nupareil (25–30 mesh) | Tacrine Hcl Pharmcoat 645 EtOH H$_2$O | 816 g 161.5 g 2125 ml 2125 ml | efficiency yield | 95% 2325.7 g | Glatt inlet outlet spray air air volume | 54° C. 33° C. 30–36 ml/min 1.8 bar 0.35 bar |
| P-36 | 685 g Nupareil (25–30 mesh) | Tacrine Hcl Pharmacoat 645 EtOH H$_2$O | 408 g 80.75 g 1062.5 ml 1062.5 ml | efficiency yield | 93% 1140 g | Glatt inlet outlet spray air air volume | 54° C. 33° C. 30–36 ml/min 1.8 bar 0.35 bar |
| P-37 | 1399 g Nupareil (25–30 mesh) | Tacrine Hcl Pharmacoat 645 EtOH H$_2$O | 816 g 161.5 g 2125 ml 2125 ml | efficiency yield | 95% 2325.7 g | Glatt inlet outlet spray air air volume | 54° C. 33° C. 30–36 ml/min 1.8 bar 0.35 bar |

TABLE 1-continued

| No. | core | coating solution | | result | | conditions | |
|---|---|---|---|---|---|---|---|
| P-38 | 1399 g Nupareil (25–30 mesh) | Tacrine Hcl Pharmacoat 645 EtOH H$_2$O | 816 g 161.5 g 2125 ml 2125 ml | efficiency yield | 95% 2327.5 g | Glatt inlet outlet spray air air volume | 54° C. 33° C. 30–36 ml/min 1.8 bar 0.35 bar |

EXAMPLE 2
Preparation of Release-Controlling-Film-Coated Pellets

The coating solution of release controlling film is of the following composition:

| | |
|---|---|
| ECN-1O | 5 g |
| Pharmacoat 645 | 1.25 g |
| DBS | 1 g |
| EtOH | 60 ml |
| Methylene Chloride | 60 ml |

EC N-10 was dissolved in ethanol. Pharmacoat 645, DBS and water were then added. After the mixture was uniformly nixed, methylene chloride was added. The mixture was stirred to be thoroughly uniform.

Inner active layer-coated pellets P-1 prepared in Example 1 (50 g) were coated on Aerocoater Model Strea-1 fluid-bed granulator under the following conditions:

| | |
|---|---|
| Inlet: | 40° C. |
| Outlet: | 30° C. |
| Air: | 1.2 Bar |
| Air volume: | 100 M$^3$/hr |
| Spray: | 4 ml/min |

The pellets coated to a suitable diameter were dried at 35° C. for 30 min. to obtain release-controlling-film-coated pellets F-1 (yield: 55.72 g; efficiency: 97%).

EXAMPLE 3
Preparation of Release-Controlling-Film-Coated Pellets

The coating solution of release-controlling-film is of the following composition:

| | |
|---|---|
| ECN-30 | 5 g |
| DBS | 1 g |
| H$_2$O | 50 ml |

EC N-30, DBS and water were uniformly mixed. Inner active layer-coated pellets P-2 prepared in Example 1 (40 g) were coated on Aerocoater Model Strea-1 fluid-bed granulator under the following conditions:

| | |
|---|---|
| Inlet: | 50° C. |
| Outlet: | 35° C. |
| Air: | 1.2 Bar |
| Air volume: | 100 M$^3$/hr |
| Spray: | 4 ml/min |

The pellets coated to a suitable diameter were dried at 50° C. for 30 min. to obtain release-controlling-film-coated pellets F-2 (yield: 44.74 g; efficiency: 79%).

Following the similar procedures to Example 2 or 3, release-controlling-film-coated pellets F-3 to F-58 were prepared on Aerocoater Model Stea-1 or Model GPC G-3 with the cores and coating solutions shown in Table 2 below:

TABLE 2

| No. | core | coating solution | | result | | conditions | |
|---|---|---|---|---|---|---|---|
| F-3 | 50 g P-2 | EC N-10 Pharmacoat 645 DBS EtOH M.C | 5 g 1.25 g 1 g 60 ml 60 ml | efficiency yield | 81.4% 55.9 g | Aeromatic inlet outlet spray air air volume | 37° C. 30° C. 5 ml/min 1.2 bar 100 m$^3$/hr |
| F-4 | P-10 40 g | Surelease H$_2$O | 40 g 50 ml | efficiency yield | 80% 48 g | Aeromatic inlet outlet spray air air volume | 40° C. 32° C. 4 ml/min 1.2 bar 103 m$^3$/hr |
| F-5 | P-10 50 g | Surelease H$_2$O | 30 g 50 ml | efficiency yield | 88.53% 56.6 g | Aeromatic inlet outlet spray air air volume | 40° C. 32° C. 4 ml/min 1.2 bar 103 m$^3$/hr |

TABLE 2-continued

| No. | core | coating solution | | result | | conditions | |
|---|---|---|---|---|---|---|---|
| F-6 | P-10 60 g | Surelease H$_2$O | 20 g 50 ml | efficiency yield | 86.4% 54.3 g | Aeromatic inlet outlet spray air air volume | 40° C. 32° C. 4 ml/min 1.2 bar 103 m$^3$/hr |
| F-7 | P-10 40 g | Surelease Pharmacoat 645 H$_2$O | 16 g 0.2 g 40 ml | efficiency yield | 84.52% 43.55 g | Aeromatic inlet outlet spray air air volume | 40° C. 32° C. 4 ml/min 1.2 bar 103 m$^3$/hr |
| F-8 | P-11 50 g | Surelease Pharmacoat 645 H$_2$O | 6 g(24 g) 0.12 g 40 ml | efficiency yield | 87.58% 55.36 g | Aeromatic inlet outlet spray air air volume | 40° C. 32° C. 4 ml/min 1.2 bar 103 m$^3$/hr |
| F-9 | P-11 50 g | ECN-10 Pharmacoat 645 DBS EtOH M.C | 5 g 1.25 g 1.0 g 60 ml 60 ml | efficiency yield | 79.17% 55.74 g | Aeromatic inlet outlet spray air air volume | 38° C. 32° C. 4 ml/min 1.2 bar 100 m$^3$/hr |
| F-10 | 600 g P-12 | EC N-10 Pharmacoat 645 DBS EtOH M.C | 50 g 12.5 g 10 g 600 ml 600 ml | efficiency yield | 78.21% 655.6 g | Glatt inlet outlet spray air air volume | 44° C. 30° C. 30 ml/min 1.8 bar 0.35 bar |
| F-11 | 600 g P-12 | Surelease Pharmacoat 645 H$_2$O | 264 g 1.32 g 440 ml | efficiency yield | 90% 660.6 g | Glatt inlet outlet spray air air volume | 50° C. 32° C. 18 ml/min 1.8 bar 0.35 bar |
| F-12 | 600 g P-13 | Surelease Pharmacoat 645 H$_2$O | 264 g 1.4 g 300 ml | efficiency yield | 92.73% 662.5 g | Glatt inlet outlet spray air air volume | 50° C. 33° C. 24 ml/min 1.8 bar 0.33 bar |
| F-13 | 600 g P-19 | Surelease Pharmacoat 645 H$_2$O | 264 g 1.4 g 400 ml | efficiency yield | 90.8% 661.2 g | Glatt inlet outlet spray air air volume | 50.C 34° C. 24 ml/min 1.8 bar 0.34 bar |
| F-14 | 1903 g P-23 | Surelease Pharmacoat 645 H$_2$O | 792 g 4.2 g 1200 ml | efficiency yield | 94.11% 2093.3 g | Glatt inlet outlet spray air air volume | 50° C. 34° C. 24 ml/min 1.8 bar 0.35 bar |
| F-15 | 2205.45 g P-24 | Surelease Pharmacoat 645 H$_2$O | 924 g 4.9 g 1400 ml | yield | 2395.5 g | Glatt inlet outlet spray air air volume | 50° C. 34° C. 24 ml/min 1.8 bar 0.35 bar |
| F-16 | 2240 g P-25 | Surelease Pharmacoat 645 H$_2$O | 924 g 4.9 g 1400 ml | efficiency yield | 90.28% 2453.2 g | Glatt inlet outlet spray air air volume | 50° C. 34° C. 24 ml/min 1.8 bar 0.35 bar |
| F-17 | 600 g P-26 | Surelease Pharmacoat 645 H$_2$O | 264 g 2.64 g 400 ml | yield efficiency | 659.4 g 86.54% | Glatt inlet outlet spray air air volume | 50° C. 34° C. 24 ml/min 1.8 bar 0.35 bar |

TABLE 2-continued

| No. | core | coating solution | | result | | conditions | |
|---|---|---|---|---|---|---|---|
| F-18 | 600 g P-26 | Surelease Pharmacoat 645 H₂O | 264 g 2.64 g 400 ml | yield | 661.6 g | Glatt inlet outlet spray air air volume | 50° C. 34° C. 24 ml/min 1.8 bar 0.35 bar |
| F-19 | 50 g P-26 | Surelease Pharmacoat 645 Talc H₂O | 24 g 0.24 g 5 g 40 ml | efficiency yield | 81.4% 59.15 g | Aeromatic inlet outlet spray air air volume | 50° C. 38° C. 4 ml/min 1.2 bar 95 m³/hr |
| F-20 | 50 g P-26 | Surelease Pharmacoat 645 Talc H₂O | 24 g 0.18 g 3 g 40 ml | efficiency yield | 80% 57.54 g | Aeromatic inlet outlet spray air air volume | 50° C. 38° C. 4 ml/min 1.2 bar 95 m³/hr |
| F-21 | 75 g P-26 | Shellac PVP Talc EtOH | 9 g 1 g 5 g 65 ml | efficiency yield | 80% 87 g | Aeromatic inlet outlet spray air air volume | 40° C. 32° C. 4 ml/min 1.2 bar 95 m³/hr |
| F-22 | 50 g P-26 | Surelease Pharmacoat 645 Aerosil H₂O | 24 g 0.18 g 2 g 40 ml | efficiency yield | 85.57% 57.0 g | Aeromatic inlet outlet spray air air volume | 50° C. 38° C. 4 ml/min 1.2 bar 95 m³/hr |
| F-23 | 50 g P-26 | EC-N10 HPC Talc EtOH | 8 g 1.6 g 2 g 130 ml | efficiency yield | 80% 59.7 g | Aeromatic inlet outlet spray air air volume | 45° C. 35° C. 4 ml/min 1.2 bar 95 m³/hr |
| F-24 | 65 g P-26 | EC-N10 HPC TEC Talc EtOH | 8 g 1.6 g 0.8 g 2 g 180 ml | efficiency yield | 80% 75 g | Aeromatic inlet outlet spray air air volume | 45° C. 35° C. 4 ml/min 1.2 bar 95 m³/hr |
| F-25 | 65 g P-26 | EudragitRS 30D EudragitRL 30D DBP Talc H₂O | 32 g 8 g 1.25 g 5 g 70 ml | efficiency yield | 84.9% 80.5 g | Aeromatic inlet outlet spray air air volume | 48° C. 36° C. 4 ml/min 1.2 bar 95 m³/hr |
| F-26 | 60 g P-26 | EudragitRS 30D EudragitRL 30D DBP Talc H₂O | 39 g 1 g 1.2 g 5 g 70 ml | efficiency yield | 84.62% 75.4 g | Aeromatic inlet outlet spray air air volume | 48° C. 36° C. 4 ml/min 1.2 bar 95 m³/hr |
| F-27 | 63.5 g P-26 | EudragitRS 30D DBP Talc H₂O | 50 g 1.5 g 6.25 g 87.5 ml | efficiency yield | 87.64% 83 g | Aeromatic inlet outlet spray air air volume | 48° C. 36° C. 4 ml/min 1.2 bar 95 m³/hr |
| F-28 | 50 g P-26 | Surelease Pharmacoat 645 H₂O | 36 g 0.45 g 60 ml | efficiency yield | 81.4% 57.5 g | Aeromatic inlet outlet spray air air volume | 50° C. 38° C. 4 ml/min 1.2 bar 95 m³/hr |
| F-29 | 50 g P-26 | Surelease Pharmacoat 645 H₂O | 40 g 0.6 g 60 ml | efficiency yield | 85% 59.1 g | Aeromatic inlet outlet spray air air volume | 50° C. 38° C. 4 ml/min 1.2 bar 95 m³/hr |

TABLE 2-continued

| No. | core | coating solution | | result | | conditions | |
|---|---|---|---|---|---|---|---|
| F-30 | 50 g P-26 | EudragitRS PO EudragitRL PO DBP Talc Acetone isopropanol | 7.5 g 0.2 g 1.5 g 10 g 50 ml 75 ml | efficiency yield | 67.7% 63 g | Aeromatic inlet outlet spray air air volume | 40° C. 34° C. 4 ml/min 1.2 bar 90 m³/hr |
| F-31 | 50 g P-26 | Surelease Pharmacoat 645 H₂O | 40 g 1 g 60 ml | efficiency yield | 85% 59.8 g | Aeromatic inlet outlet spray air air volume | 50° C. 36° C. 4 ml/min 1.2 bar 95 m³/hr |
| F-32 | 65 g P-26 | EC-N10 HPC TEC Talc EtOH | 8 g 1.8 g 0.8 g 4 g 150 ml | efficiency yield | 80.48% 77.05 g | Aeromatic inlet outlet spray air air volume | 43° C. 35° C. 4 ml/min 1.2 bar 95 m³/hr |
| F-33 | 65 g P-26 | EC-N10 HPC DBS Talc EtOH | 8 g 1.8 g 0.8 g 4 g 150 ml | efficiency yield air | 80.0% 76.66 g 1.2 bar | Aeromatic inlet outlet spray air volume | 43° C. 35° C. 4 ml/min 95 m³/hr |
| F-34 | 66 g P-26 | EC-N10 HPC DBS Talc isopropanol | 8 g 1.8 g 0.8 g 4 g 150 ml | efficiency yield | 80.0% 77.9 g | Aeromatic inlet outlet spray air air volume | 43° C. 35° C. 4 ml/min 1.2 bar 95 m³/hr |
| F-35 | 80 g P-26 | EC-N10 HPC Talc isopropanol | 8 g 2 g 5 g 160 ml | efficiency yield | 85.0% 93.1 g | Aeromatic inlet outlet spray air air volume | 43° C. 35° C. 4 ml/min 1.2 bar 95 m³/hr |
| F-36 | 600 g P-29 | EC-N10 Pharmacoat 645 DBS EtOH M.C | 50 g 12.5 g 5 g 600 ml 600 ml | efficiency yield | 83.5% 656.35 g | Aeromatic inlet outlet spray air air volume | 44° C. 36° C. 30 ml/min 1.5 bar 0.34 m³/hr |
| F-37 | 600 g P-29 | EC-N10 Pharmacoat 645 TEC EtOH M.C | 60 g 15 g 6 g 600 ml 600 ml | efficiency yield | 84.32% 668.3 g | Aeromatic inlet outlet spray air air volume | 44° C. 36° C. 30 ml/min 1.8 bar 0.34 m³/hr |
| F-38 | 100 g P-26 | EudragitRS 30D EudragitRL 30D DBP Talc H₂O | 32 g 8 g 1.25 g 5 g 70 ml | efficiency yield | 84.9% 115.5 g | Aeromatic inlet outlet spray air air volume | 48° C. 35° C. 4–5 ml/min 1.2 bar 95 m³/hr |
| F-39 | 65 g P-26 | EudragitRS 30D EudragitRL 30D DBP Talc H₂O | 32 g 8 g 1.25 g 5 g 70 ml | efficiency yield | 85% 80.75 g | Aeromatic inlet outlet spray air air volume | 48° C. 35° C. 4–5 ml/min 1.2 bar 95 m³/hr |
| F-40 | 70 g P-29 | EC-N10 Pharmacoat 645 TEC Talc EtOH M.C | 8 g 1.8 g 0.8 g 3 g 130 ml 30 ml | efficiency yield | 80% 80.8 g | Aeromatic inlet outlet spray air air volume | 44° C. 36° C. 4–5 ml/min 1.2 bar 95 m³/hr |
| F-41 | 600 g P-29 | Surelease Pharmacoat 645 H₂O | 264 g 2.64 g 400 ml | efficiency yield | 94.7% 665 g | Glatt inlet outlet spray air air volume | 50° C. 34° C. 24 ml/min 1.5 bar 0.35 bar |

TABLE 2-continued

| No. | core | coating solution | | result | | conditions | |
|---|---|---|---|---|---|---|---|
| F-42 | 600 g P-29 | Surelease Pharmacoat 645 H$_2$O | 264 g 2.64 g 400 ml | efficiency yield | 91.8% 663.2 g | Glatt inlet outlet spray air air volume | 50° C. 34° C. 24 ml/min 1.8 bar 0.35 bar |
| F-43 | 65 g P-31 | EC-N10 Pharmacoat 645 TEC Talc EtOH M.C | 8 g 1.8 g 0.8 g 3 g 130 ml 50 ml | efficiency yield | 80% 75.8 g | Glatt inlet outlet spray air air volume | 44° C. 36° C. 3.5 ml/min 1.2 bar 95 |
| F-44 | 60 g P-32 | EC-N10 Pharmacoat 645 TEC Talc EtOH M.C | 8 g 1.8 g 0.8 g 4 g 110 ml 50 ml | efficiency yield | 79.45% 71.6 g | Aeromatic inlet outlet spray air air volume | 44° C. 36° C. 3.5 ml/min 1.2 bar 95 m$^3$/hr |
| F-45 | 53 g P-33 | EC-N10 Pharmacoat 645 TEC Talc EtOH M.C | 8 g 1.8 g 0.8 g 4 g 110 ml 50 ml | efficiency yield | 80.14% 64.7 g | Aeromatic inlet outlet spray air air volume | 44° C. 36° C. 3.5 ml/min 1.2 bar 95 m$^3$/hr |
| F-46 | 600 g P-30 | EC-N10 Pharmacoat 645 TEC EtOH M.C | 60 g 18 g 6 g 600 ml 600 ml | efficiency yield | 80.23% 667.4 g | Glatt inlet outlet spray air air volume | 44° C. 34° C. 33 ml/min 1.8 bar 0.35 bar |
| F-47 | 600 g P-30 | EC-N10 Pharmacoat 645 TEC EtOH M.C | 60 g 17 g 6 g 600 ml 600 ml | acceptable | | Glatt inlet outlet spray air air volume | 44° C. 36° C. 33 ml/min 1.8 bar 0.35 bar |
| F-48 | 600 g P-30 | EC-N10 Pharmacoat 645 DBS EtOH M.C | 50 g 15 g 5 g 600 ml 600 ml | efficiency yield | 80.3% 656.2 g | Glatt inlet outlet spray air air volume | 44° C. 36° C. 33 ml/min 1.8 bar 0.35 bar |
| F-49 | 600 g P-35 | Surelease Pharmacoat 645 H$_2$O | 262 g 2.64 g 400 ml | efficiency yield | 95.5% 665.6 g | Glatt inlet outlet spray air air volume | 50° C. 34° C. 24 ml/min 1.8 bar 0.35 bar |
| F-50 | 600 g P-34 | Surelease Pharmacoat 645 H$_2$O | 262 g 2.64 g 400 ml | efficiency yield | 93.82% 664.4 g | Glatt inlet outlet spray air air volume | 50° C. 34° C. 24 ml/min 1.8 bar 0.35 bar |
| F-51 | 600 g P-35 | EC-N10 Pharmacoat 645 DBS EtOH M.C | 50 g 15 g 5 g 600 ml 600 ml | efficiency yield | 82% 657.6 g | Glatt inlet outlet spray air air volume | 44° C. 36° C. 33 ml/min 1.8 bar 0.35 bar |
| F-52 | 1115 g P-36 | EC-N10 Pharmacoat 645 DBS EtOH M.C | 92.5 g 27.75 g 9.25 g 925 ml 925 ml | efficiency yield | 85% 1225.1 g | Glatt inlet outlet spray air air volume | 44° C. 36° C. 33 ml/min 1.8 bar 0.35 bar |
| F-53 | 2330 g P-34 | EC-N10 Pharmacoat 645 DBS EtOH M.C | 175 g 52.5 g 17.5 g 1750 ml 1750 ml | efficiency yield | 85.6% 2539.45 g | Glatt inlet outlet spray air air volume | 44° C. 36° C. 36 ml/min 1.8 bar 0.35 bar |

TABLE 2-continued

| No. | core | coating solution | | result | | conditions | |
|---|---|---|---|---|---|---|---|
| F-54 | 2320 g P-37 | EC-N10 Pharmcoat 645 DBS EtOH M.C | 190 g 57 g 19 g 1900 ml 1900 ml | efficiency ° yield | 85.7% 2547.96 g | Glatt inlet outlet spray air air volume | 44° C. 36° C. 33 ml/min 1.8 bar 0.35 bar |
| F-55 | 2322.5 g P-38 | EC-N10 Pharmacoat 645 DBS EtOH M.C | 190 g 57 g 19 g 1900 ml 1900 ml | efficiency yield | 85.7% 2550.5 g | Glatt inlet outlet spray air air volume | 44° C. 36° C. 33 ml/min 1.8 bar 0.35 bar |

EXAMPLE 4

Preparation of Active Over-Coated Pellets

The coating solution of active overcoat layer is of the following composition:

| | |
|---|---|
| Tacrine HCl | 5.506 g |
| Pharmacoat 645 | 1.1012 g |
| EtOH | 30 ml |
| $H_2O$ | 30 ml |

Ethanol and water were mixed first. Pharmacoat 645 was dissolved in the mixture, and thereafter Tacrine HCl was added. The resultant mixture was heated to 50° C. to dissolve the components.

Release-controlling-film-coated pellets F-13 prepared in Example 3 were coated on Aerocoater Model Strea-1 under the following conditions:

| | |
|---|---|
| Inlet: | 50° C. |
| Outlet: | 40° C. |
| Air: | 1.2 Bar |
| Air volume: | 100 $M^3$/hr |
| Spray: | 3 ml/min |

The pellets coated to a suitable diameter were dried at 50° C. for 30 min. to obtain active overcoat-coated pellets O-1 (yield: 105.5 g; efficiency: 83%).

Following the similar procedures, active overcoat-coated pellets O-2 to O-10 were prepared on Aerocoater Model Stea-1 or Glatt Model GPC G-3 fluid-bed granulator with the cores and coating solutions shown in Table 3 below:

TABLE 3

| No. | core | coating solution | | result | | conditions | |
|---|---|---|---|---|---|---|---|
| O-1 | 100 g F-13 | Tacrine Hcl Pharmacoat 645 EtOH $H_2O$ | 5.506 g 1.1012 g 30 ml 30 ml | efficiency yield | 83% 105.5 g | Aeromatic inlet outlet spray air air volume | 50° C. 40° C. 3 ml/min 1.2 bar 100 $m^3$/hr |
| O-2 | 2070 g F-14 +Talc 10 g | Tacrine Hcl Pharmacoat 645 $H_2O$ | 100 g 19.8 g 700 ml | efficiency yield | 98.0% 2197.2 g | Glatt inlet outlet spray air air volume | 50° C. 36° C. 24 ml/min 1.8 bar 0.35 bar |
| O-3 | 52 g F-45 | Tacrine Hcl Pharmacoat 645 $H_2O$ | 2.5 g 0.5 g 50 ml | efficiency yield | 86.7% 54.6 g | Aeromatic inlet outlet spray air air volume | 50° C. 40° C. 3 ml/min 1.2 bar 95 $m^3$/hr |
| O-4 | F-47 | Tacrine Hcl Pharmacoat 645 $H_2O$ | 29 g 5.8 g 300 ml | efficiency yield | 86.7% 54.6 g | Glatt inlet outlet spray air air volume | 50° C. 38° C. 18 ml/min 1.8 bar 0.35 bar |
| O-5 | 600 g F-48 | Tacrine Hcl Pharmacoat 645 $H_2O$ | 25.5 g 5.1 g 300 ml | efficiency yield | 92% 627.85 g | Glatt inlet outlet spray air air volume | 50° C. 38° C. 18 ml/min 1.8 bar 0.35 bar |
| O-6 | 600 g F-36 | Tacrine Hcl Pharmacoat 645 $H_2O$ | 27 g 5.4 g 300 ml | efficiency yield | 90% 628.8 g | Glatt inlet outlet spray | 50° C. 38° C. 18 ml/min |

TABLE 3-continued

| No. | core | coating solution | | result | | conditions | |
|---|---|---|---|---|---|---|---|
| O-7 | 600 g F-51 | Tacrine Hcl Pharmacoat 645 H$_2$O | 26 g 5.2 g 300 ml | efficiency yield | 93% 628.9 g | air air volume Glatt inlet outlet spray air air volume | 1.8 bar 0.35 bar 50° C. 38° C. 18 ml/min 1.8 bar 0.35 bar |
| O-8 | 1200 g F-52 | Tacrine Hcl Pharmacoat 645 H$_2$O | 52 g 10.4 g 450 ml | efficiency yield | 96% 1260 g | Glatt inlet outlet spray air air volume | 50° C. 40° C. 18 ml/min 1.8 bar 0.35 bar |
| O-9 | 2540 g F-53 | Tacrine Hcl Pharmacoat 645 H$_2$O | 111.8 g 22.36 g 967.5 ml | efficiency yield | 98% 2674.16 g | Glatt inlet outlet spray air air volume | 50° C. 38° C. 18 ml/min 1.8 bar 0.35 bar |
| O-10 | 2540 g F-55 | Tacrine Hcl Pharmacoat 645 H$_2$O | 111.8 g 22.36 g 970 ml | efficiency yield | 98% 2671.2 g | Glatt inlet outlet spray air air volume | 50° C. 38° C. 20 ml/min 1.8 bar 0.35 bar |

EXAMPLE 5

Encapsulation

Active overcoat-coated pellets O-10 were encapsulated in #2 capsules on MG2 automatic encapsulator (Mgfutura Co, Italy). The ingredients and their ratios, on the basis of 10,000 capsules, are shown below:

| Active Inner Layer-Coated Pellets | |
|---|---|
| Nu-Pareil (25–30 mesh) | 1201.7 g |
| Tacrine HCl Monohydrate | 665.86 g |
| Hydroxypropyl Methylcellulose 2910 USP | 131.78 g |
| Ethanol (95%) | 1825 ml |
| Water | 1825 ml |
| Release-Controlling-Film-Coated Pellets | |
| Ethyl Cellulose | 139.86 g |
| Hydroxypropyl Methylcellulose 2910 USP | 41.96 g |
| Dibutyl Sebacate | 13.986 g |
| Ethanol (95%) | 1632 ml |
| Methylene Chloride | 1632 ml |
| Active Overcoat-Coated Pellets | |
| Tacrine HCl Monohydrate | 94.1 g |
| Hydroxypropyl Methylcellulose 2910 USP | 18.82 g |
| Water | 859 ml |
| Total | 2308.1 g |

Each capsule contains 230.8 mg of pellets, with a label claim of 76 mg of Tacrine.HCl:H$_2$O.

EXAMPLE 6

Dissolution Test

Figure 2:
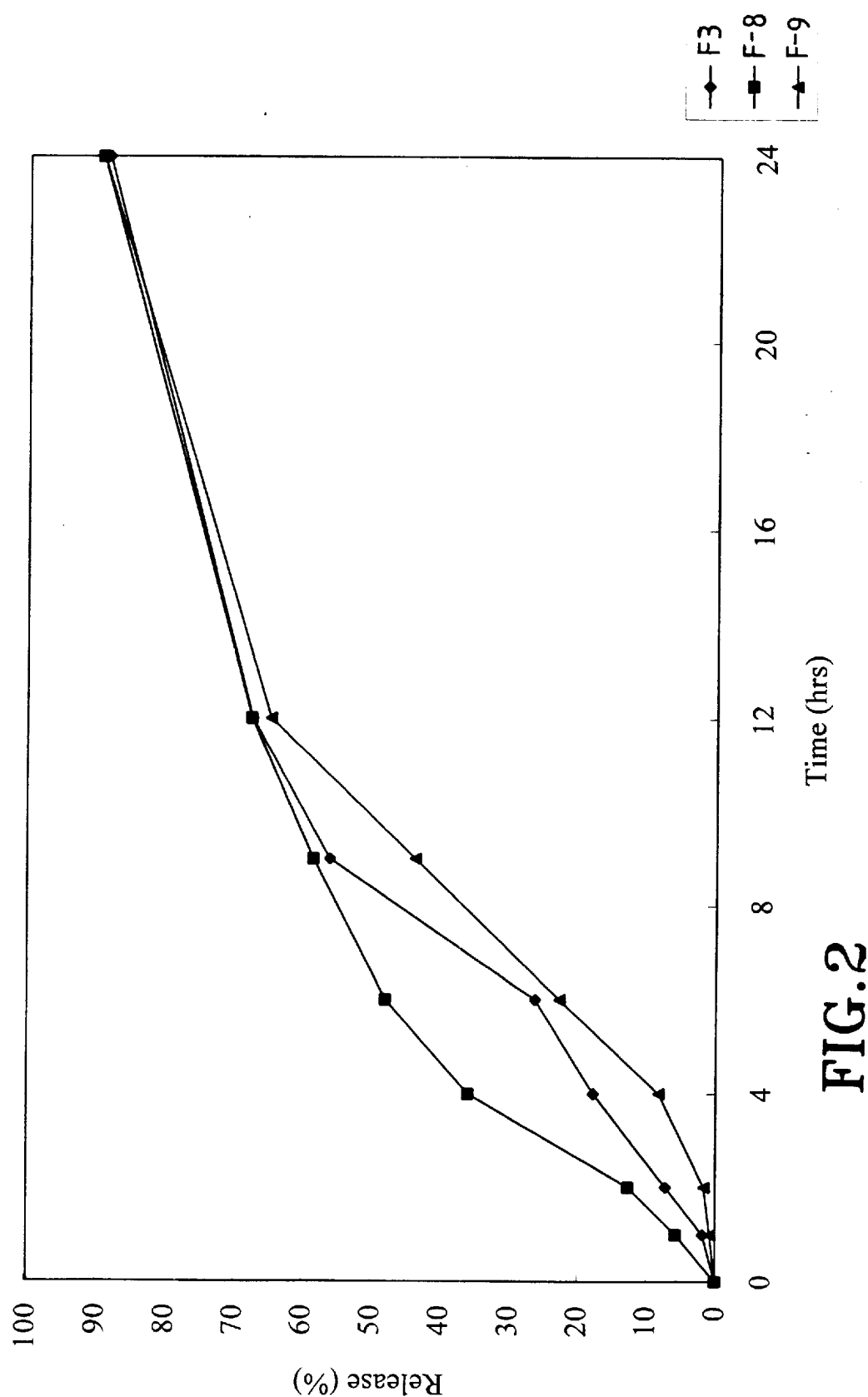
FIG. 2 depicts the dissolution curves of release-controlling-film coated pellets F-3 (240.8 mg, —◆—), F-8 (235 mg, —■—), and F-9 (240.8 mg, —▲—) in $H_2O$.
Figure 3:
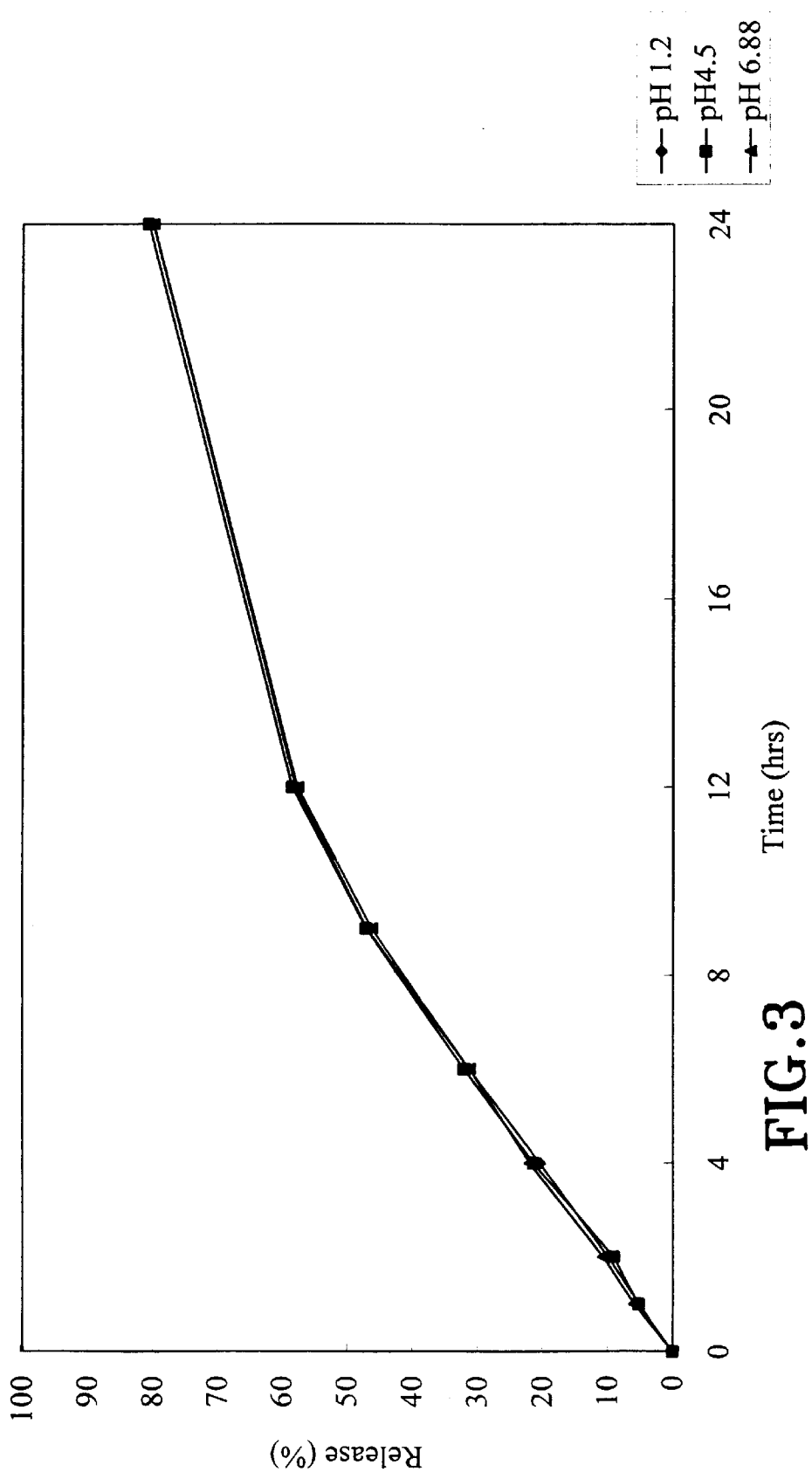
FIG. 3 depicts the dissolution curves of release-controlling-film coated pellets F-10 (240.8 mg) at pH 1.2 (—◆—), 4.5 (—■—) and 6.88 (—▲—).
Figure 4:
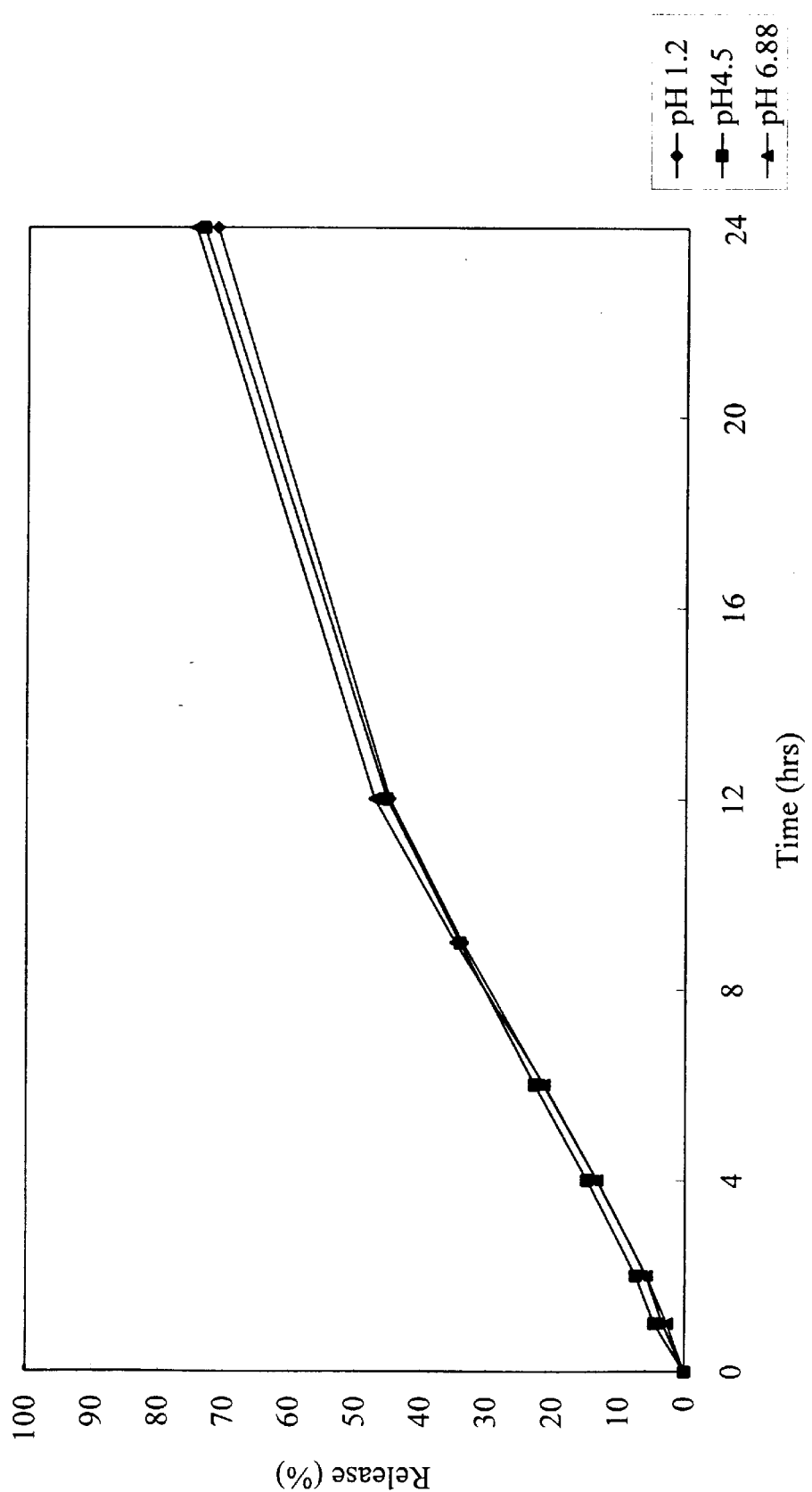
FIG. 4 depicts the dissolution curves of release-controlling-film coated pellets F-11 (235 mg) at pH 1.2 (—◆—), 4.5 (—■—) and 6.88 (—▲—).
Figure 5:
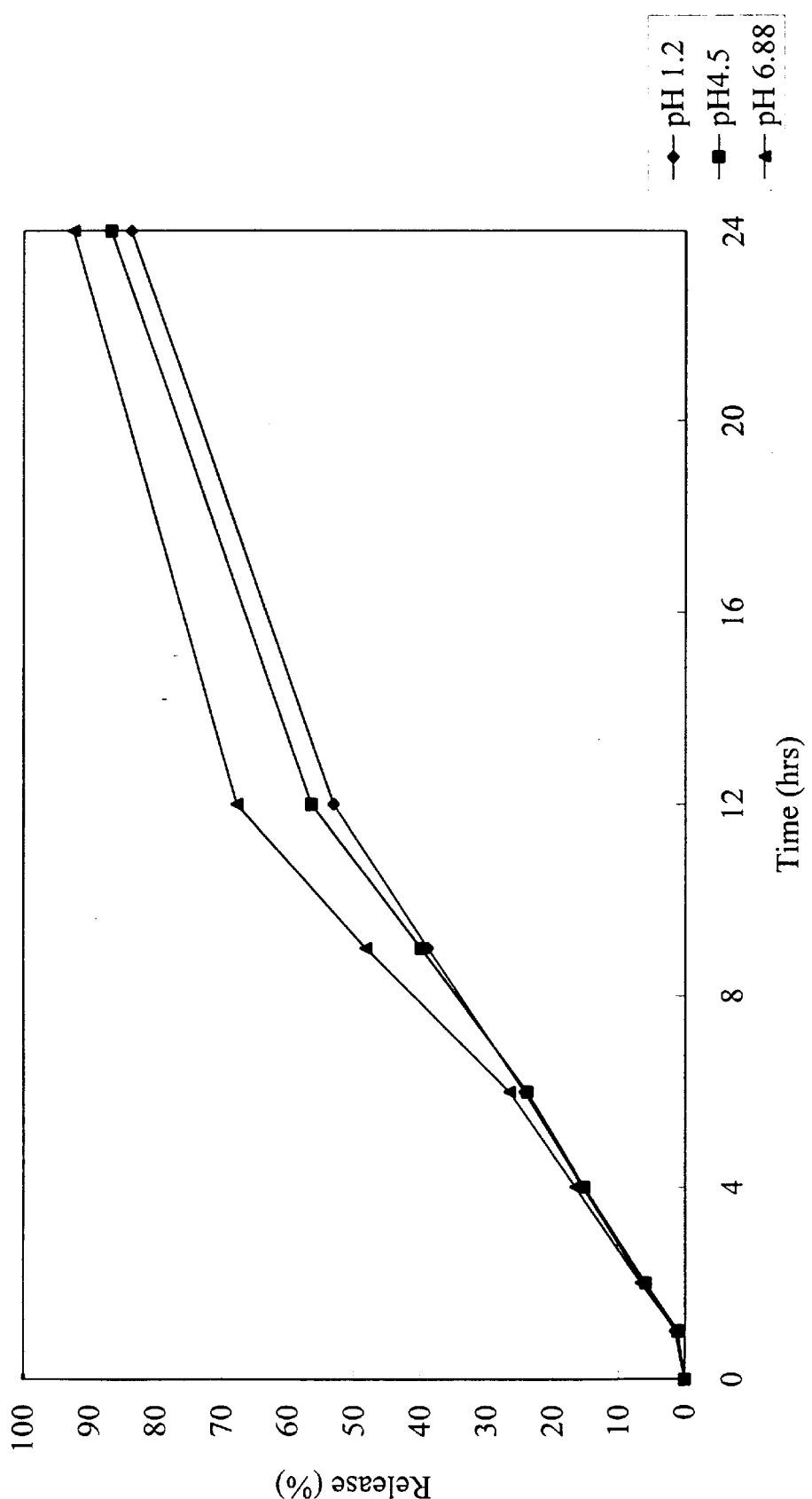
FIG. 5 depicts the dissolution curves of release-controlling-film coated pellets F-12 (235 mg) at pH 1.2 (—◆—), 4.5 (—■—) and 6.88 (—▲—).
Figure 6:
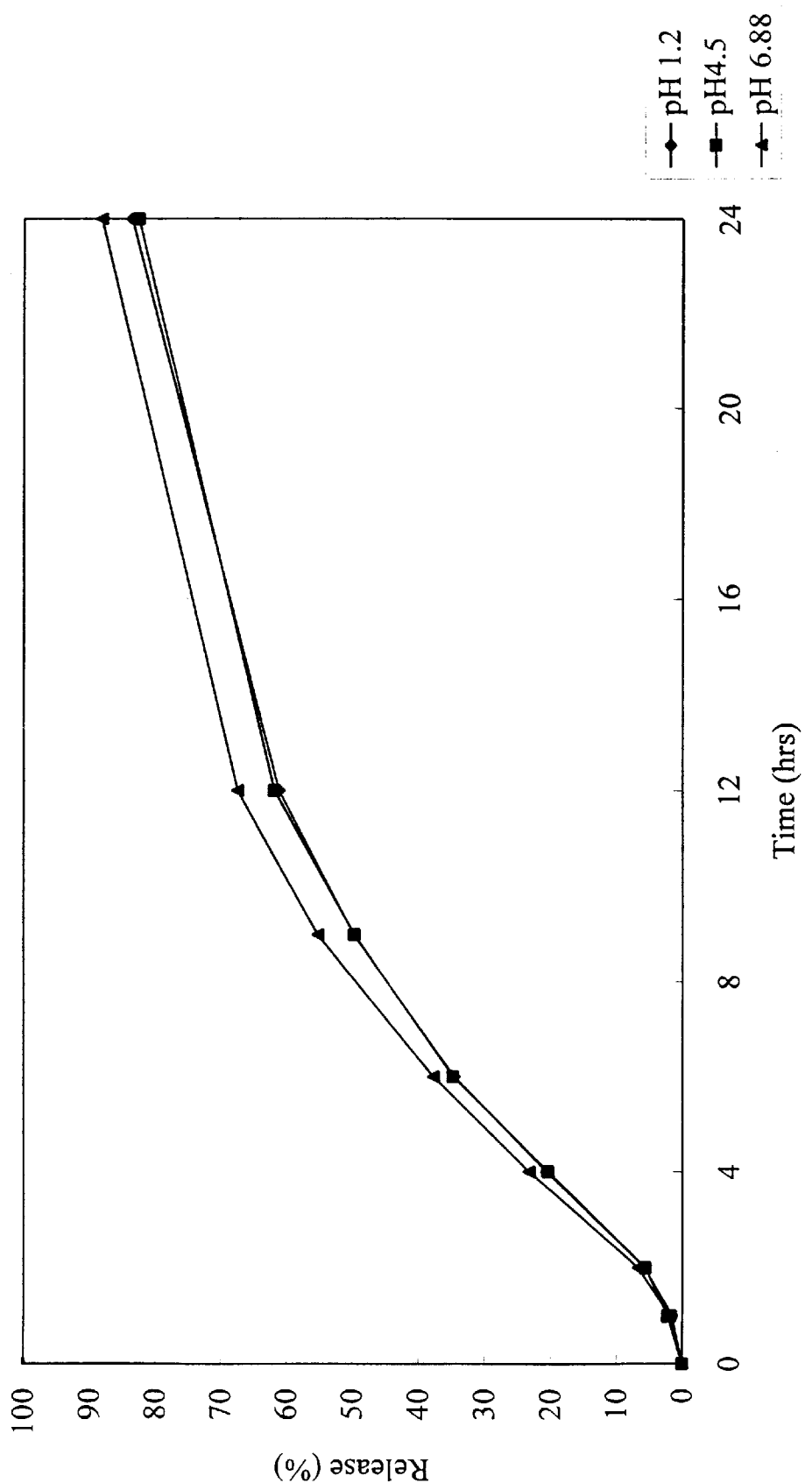
FIG. 6 depicts the dissolution curves of release-controlling-film coated pellets F-13 (232 mg) at pH 1.2 (—◆—), 4.5 (—■—) and 6.88 (—▲—).
Figure 7:
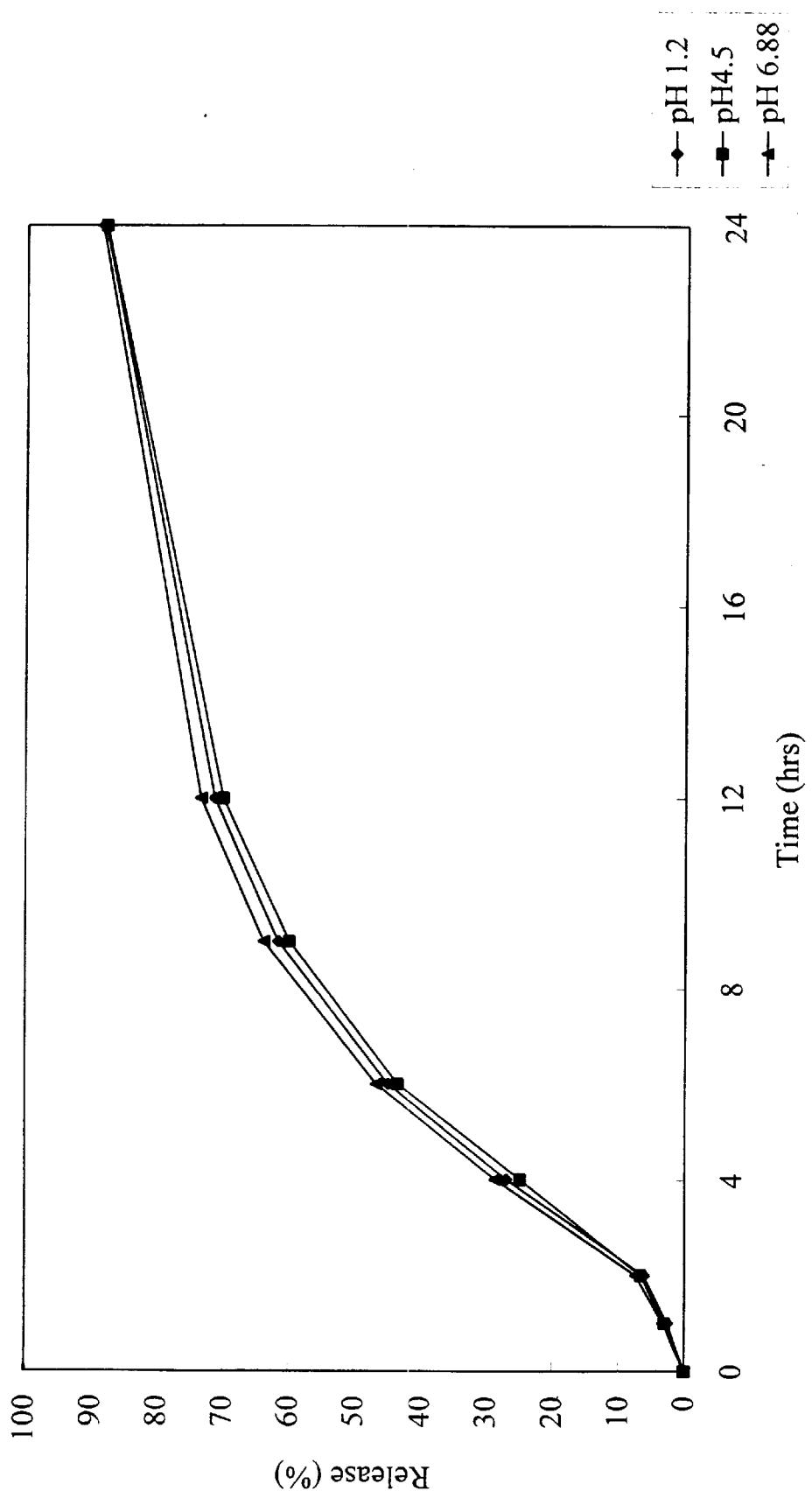
FIG. 7 depicts the dissolution curves of release-controlling-film coated pellets F-14 (233 mg) at pH 1.2 (—◆—), 4.5 (—■—) and 6.88 (—▲—).
Figure 8:
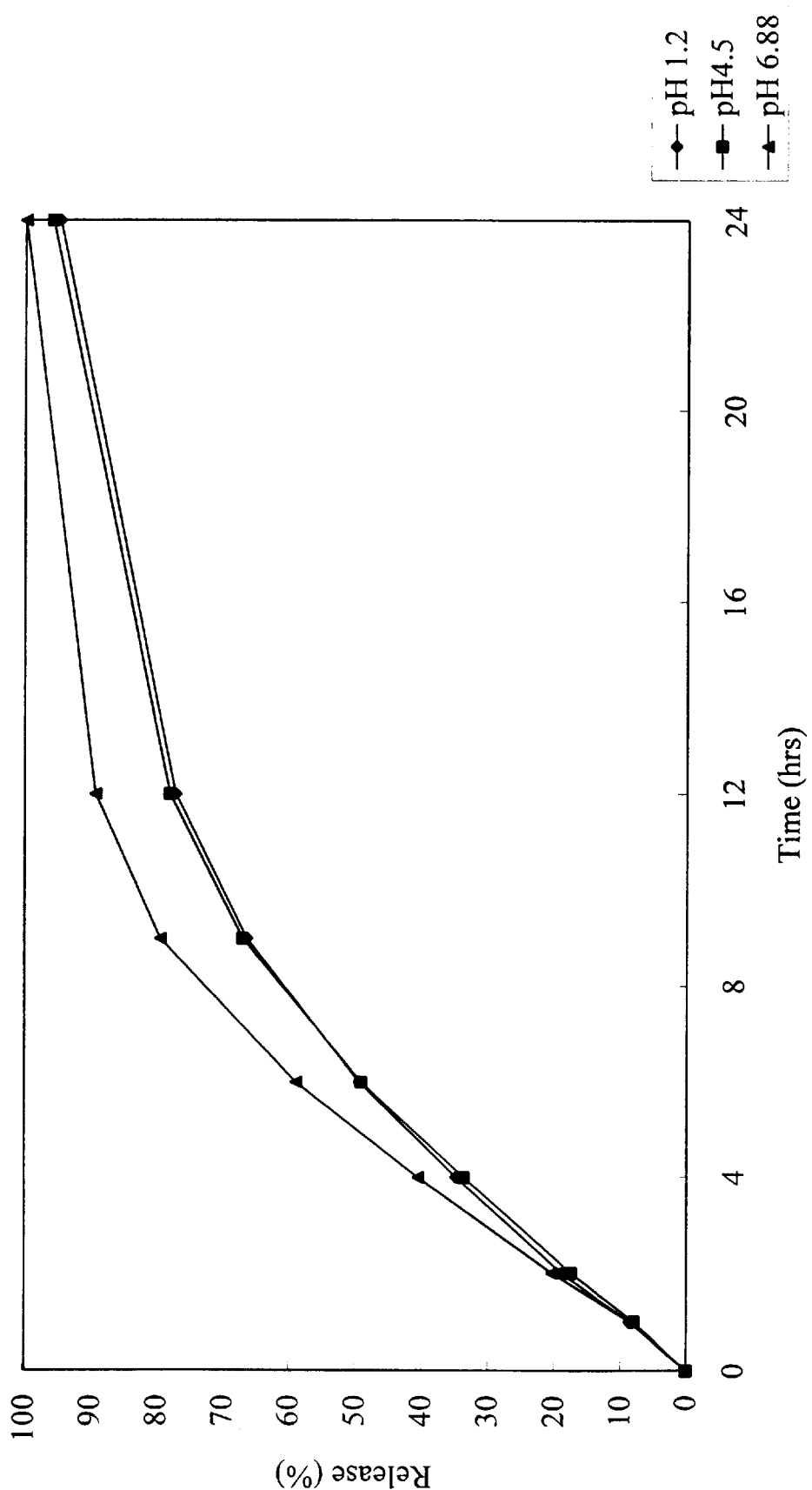
FIG. 8 depicts the dissolution curves of release-controlling-film coated pellets F-18 (252.2 mg) at pH 1.2 (—◆—), 4.5 (—■—) and 6.88 (—▲—).
Figure 9:
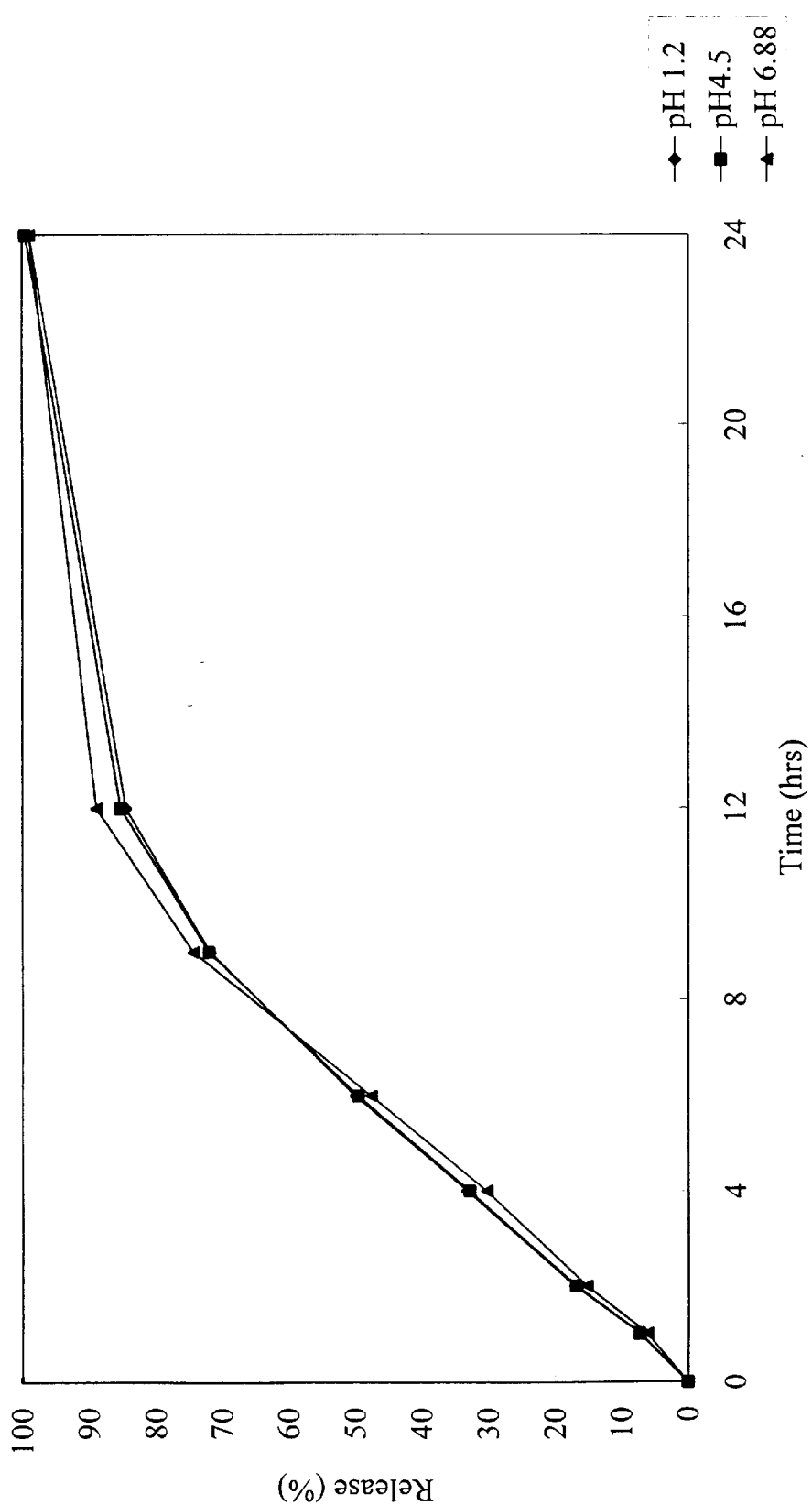
FIG. 9 depicts the dissolution curves of release-controlling-film coated pellets F-20 (265 mg) at pH 1.2 (—◆—), 4.5 (—■—) and 6.88 (—▲—).
Figure 10:
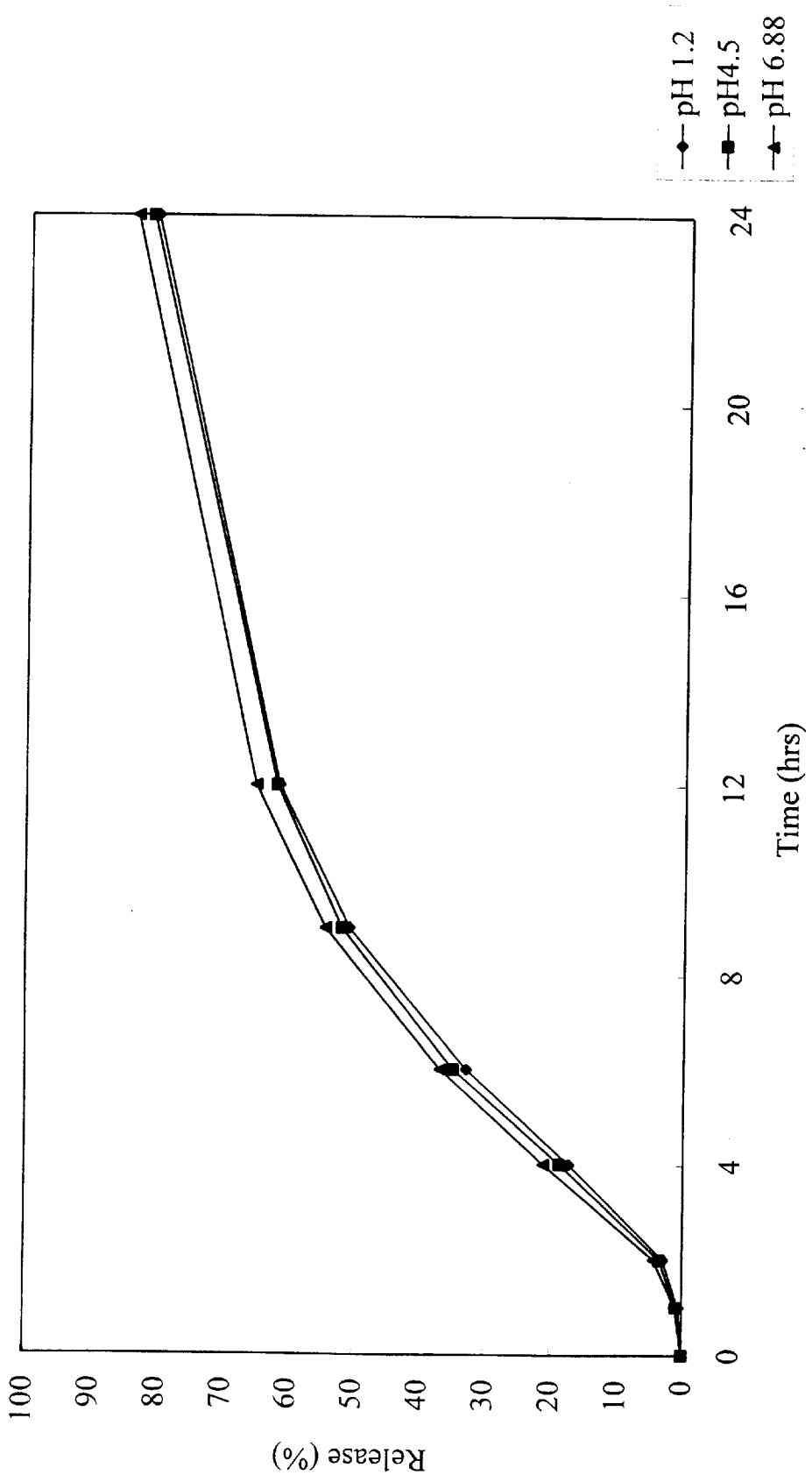
FIG. 10 depicts the dissolution curves of release-controlling-film coated pellets F-24 (265 mg) at pH 1.2 (—◆—), 4.5 (—■—) and 6.88 (—▲—).
Figure 11:
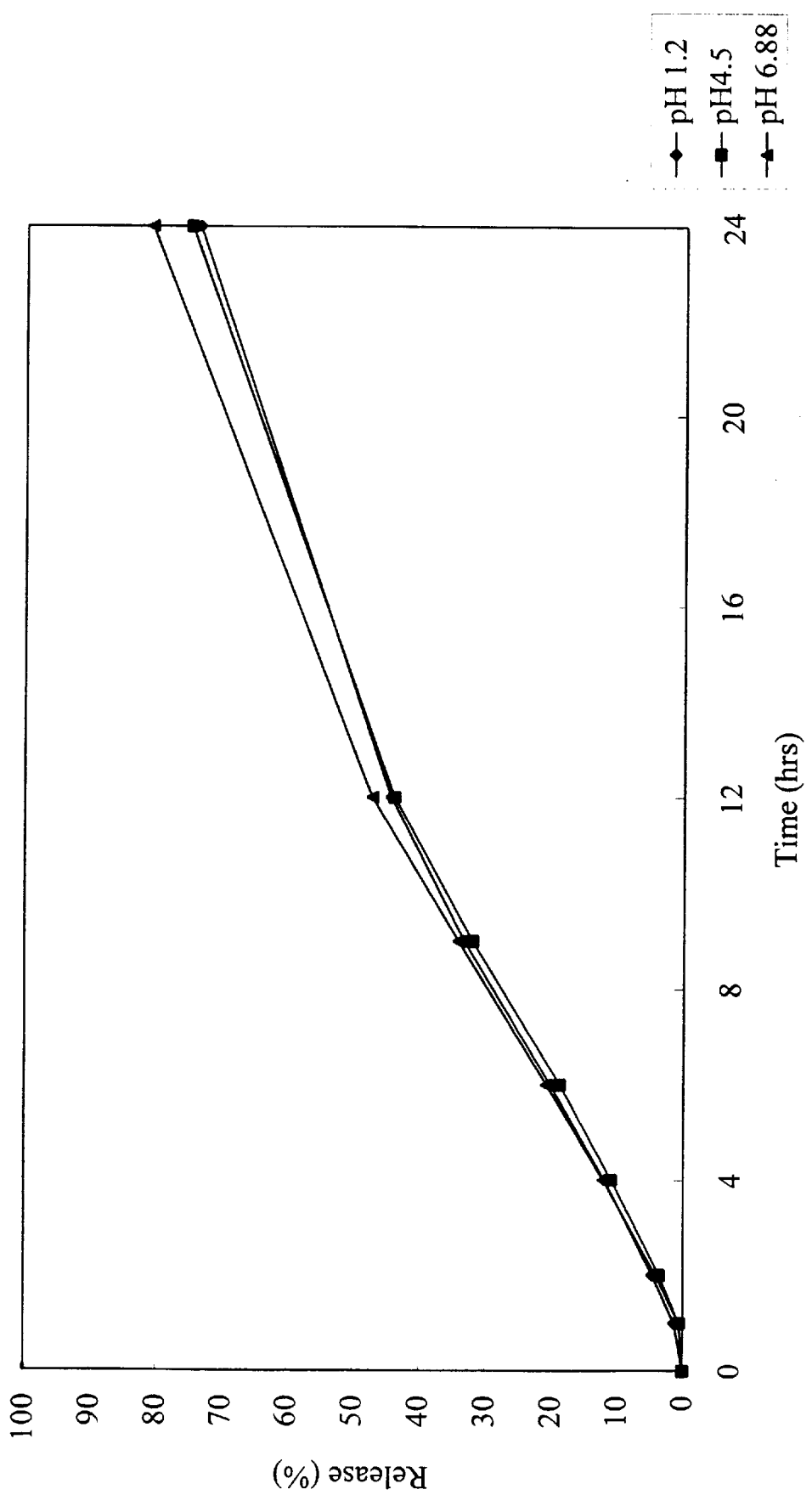
FIG. 11 depicts the dissolution curves of release-controlling-film coated pellets F-28 (274.5 mg) at pH 1.2 (—◆—), 4.5 (—■—) and 6.88 (—▲—).
Figure 12:
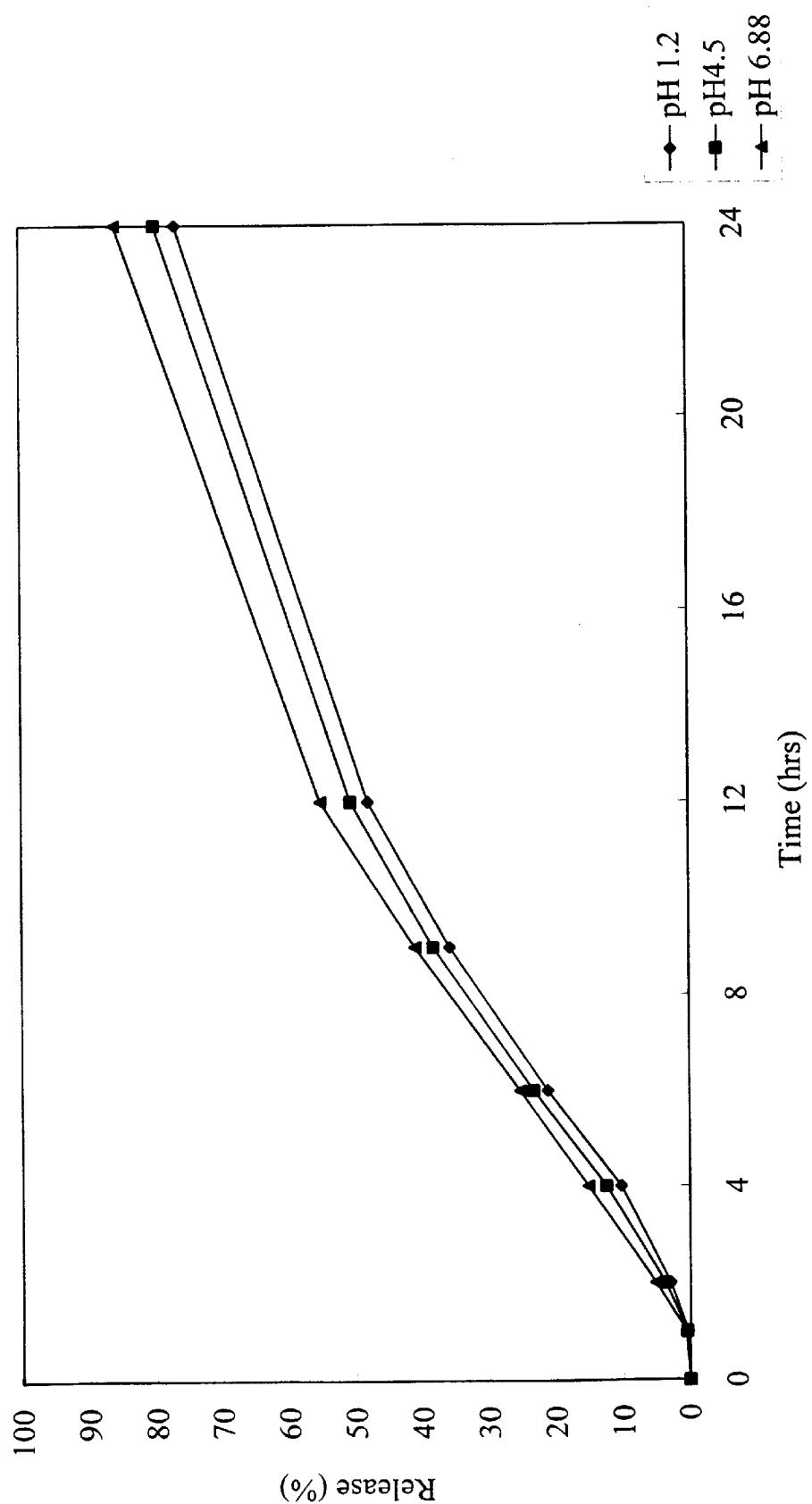
FIG. 12 depicts the dissolution curves of release-controlling-film coated pellets F-29 (270.4 mg) at pH 1.2 (—◆—), 4.5 (—■—) and 6.88 (—▲—).
Figure 13:
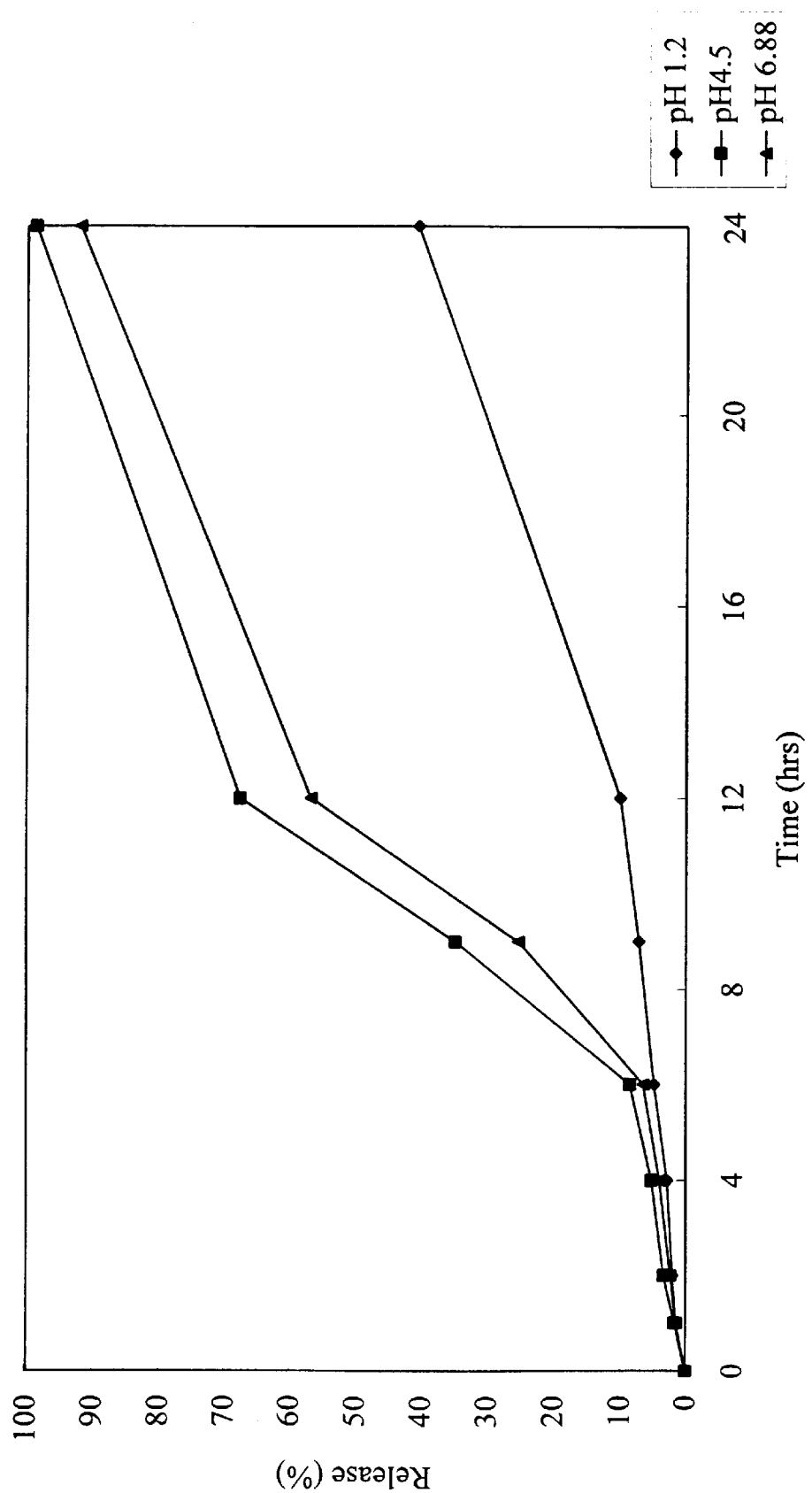
FIG. 13 depicts the dissolution curves of release-controlling-film coated pellets F-30 (289 mg) at pH 1.2 (—◆—), 4.5 (—■—) and 6.88 (—▲—).
Figure 14:
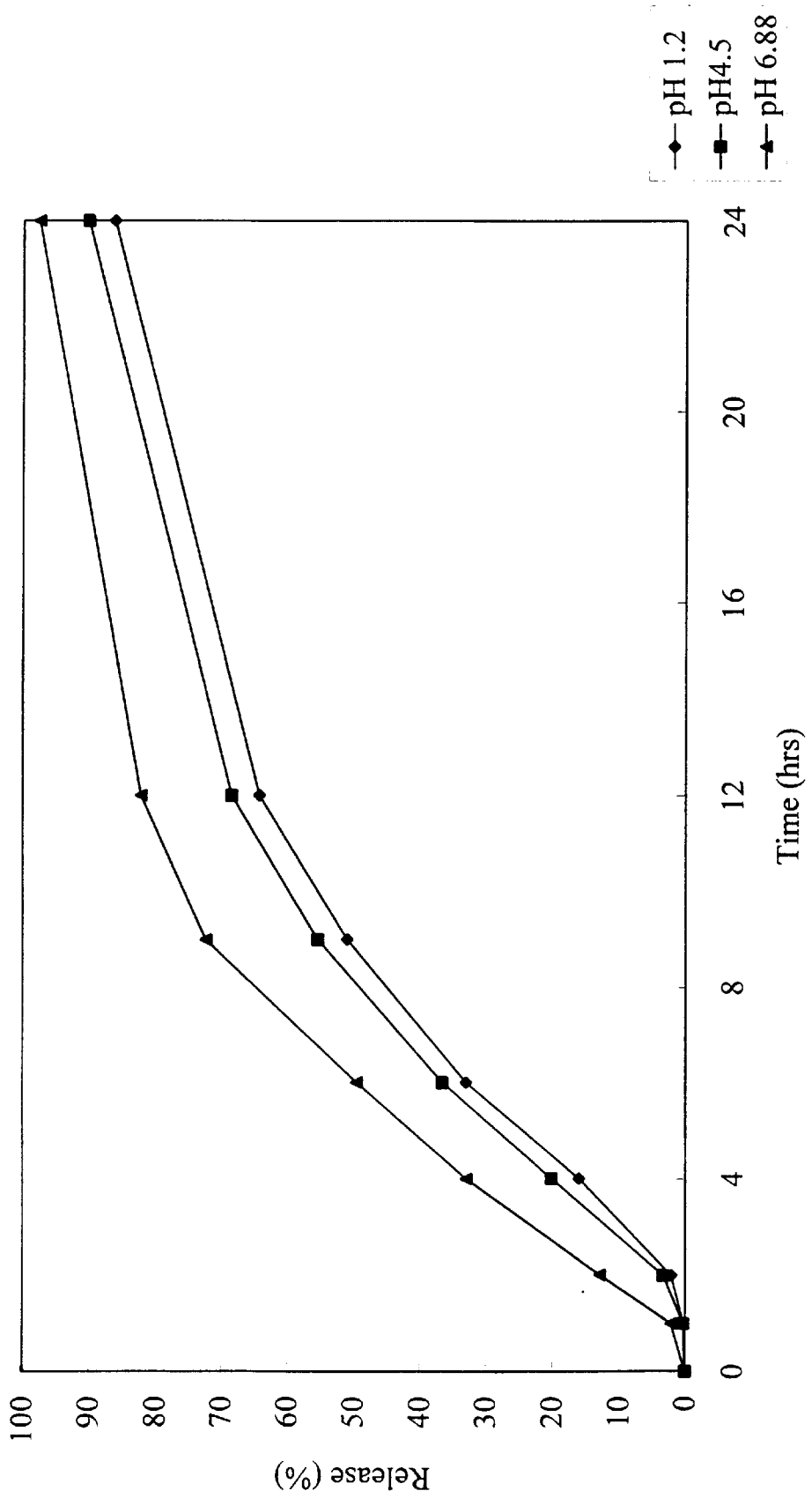
FIG. 14 depicts the dissolution curves of release-controlling-film coated pellets F-31 (237.5 mg) at pH 1.2 (—◆—), 4.5 (—■—) and 6.88 (—▲—).
Figure 15:
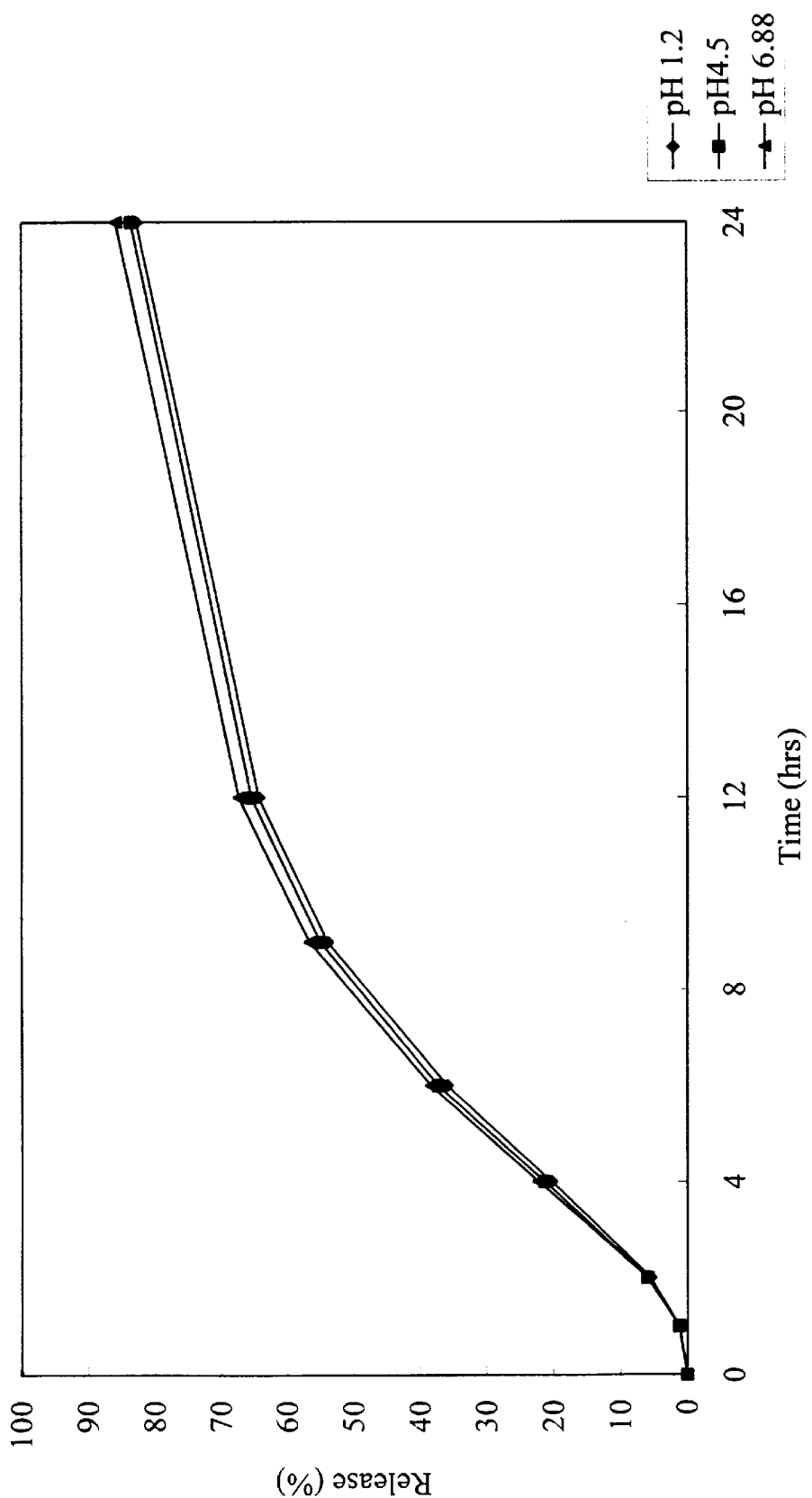
FIG. 15 depicts the dissolution curves of release-controlling-film coated pellets F-32 (271 mg) at pH 1.2 (—◆—), 4.5 (—■—) and 6.88 (—▲—).
Figure 16:
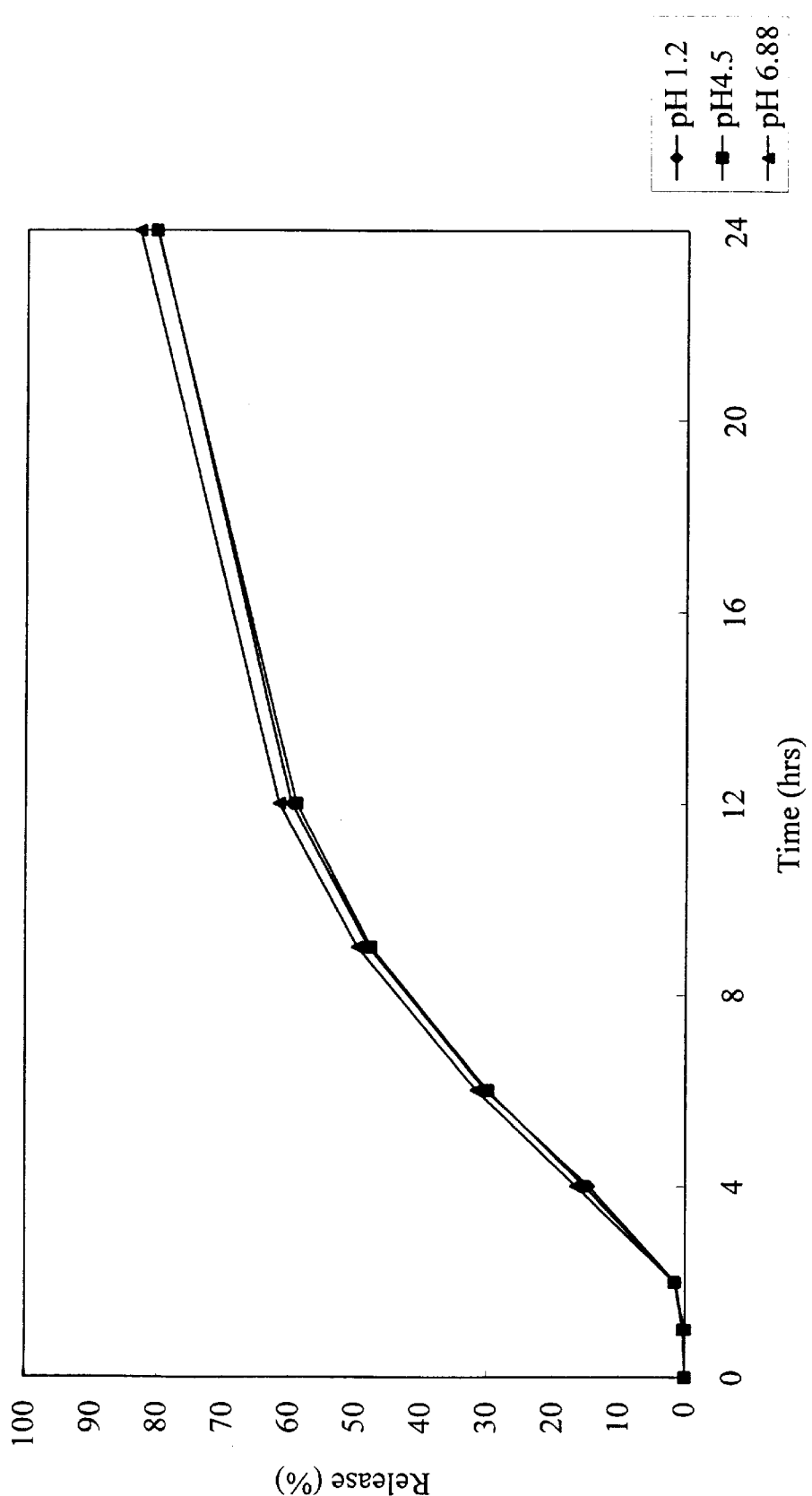
FIG. 16 depicts the dissolution curves of release-controlling-film coated pellets F-33 (270 mg) at pH 1.2 (—◆—), 4.5 (—■—) and 6.88 (—▲—).
Figure 17:
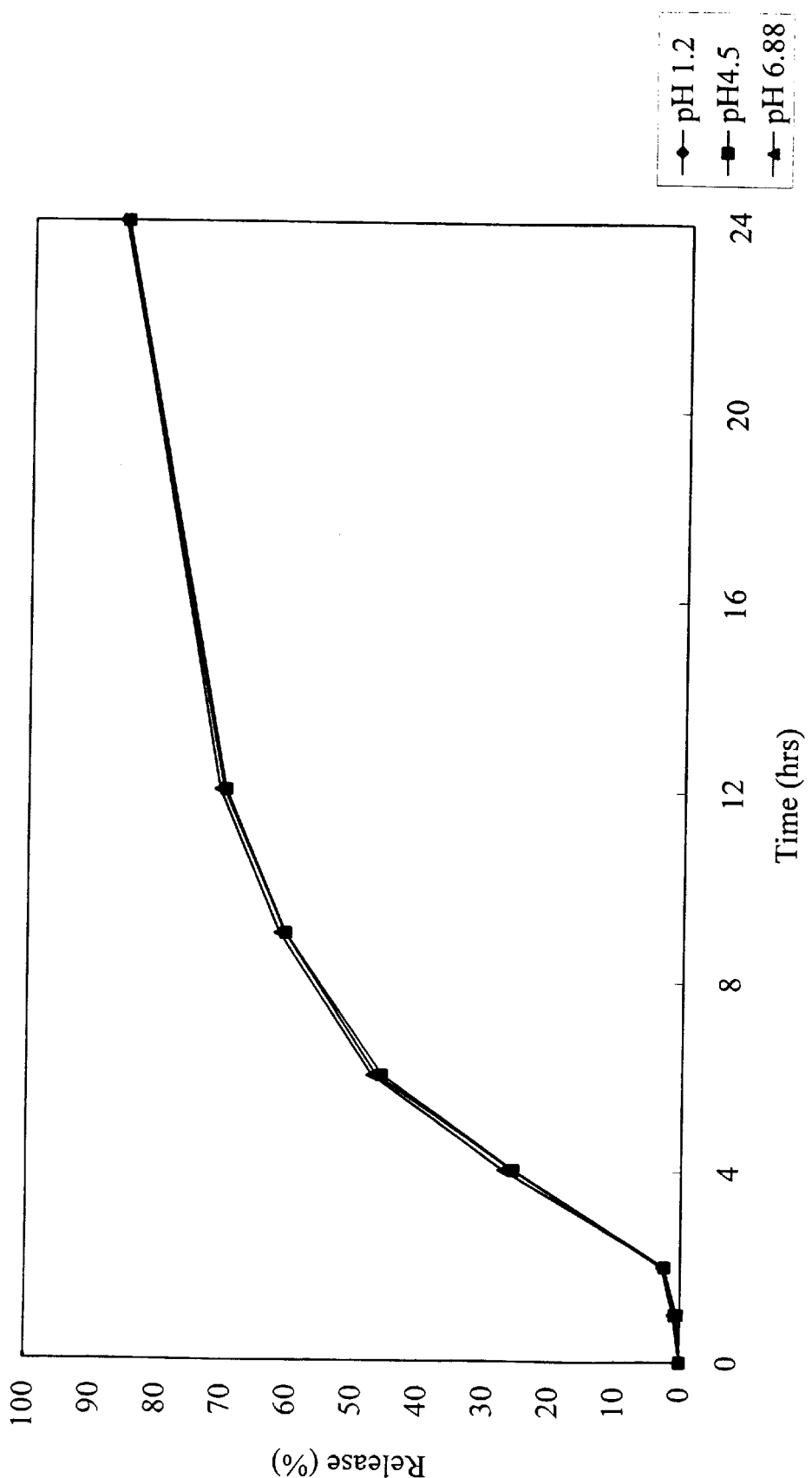
FIG. 17 depicts the dissolution curves of release-controlling-film coated pellets F-36 (250.8 mg) at pH 1.2 (—◆—),4.5(—■—) and 6.88 (—▲—).
Figure 18:
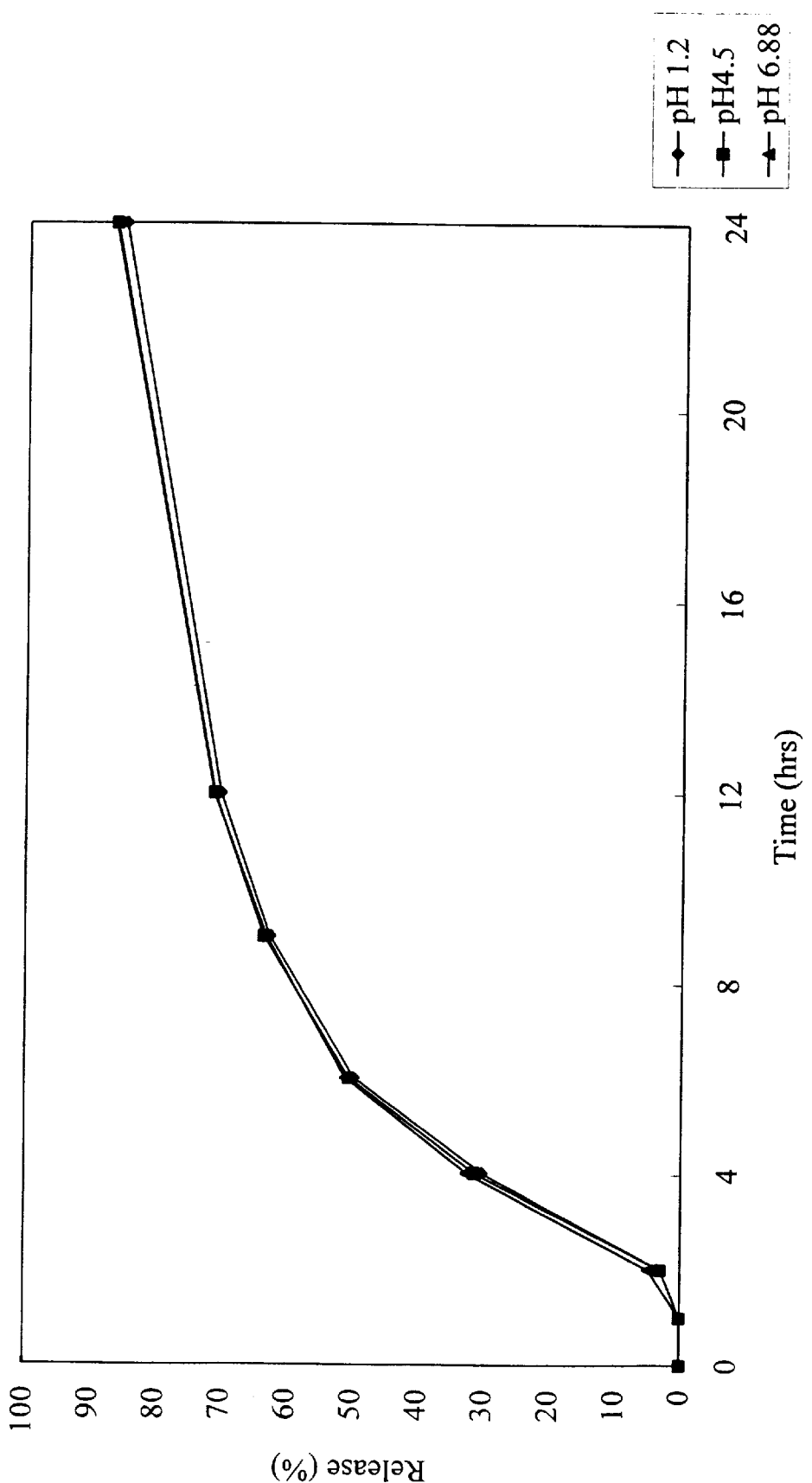
FIG. 18 depicts the dissolution curves of release-controlling-film coated pellets F-37 (253.3 mg) at pH 1.2 (—◆—), 4.5 (—■—) and 6.88 (—▲—).
Figure 19:
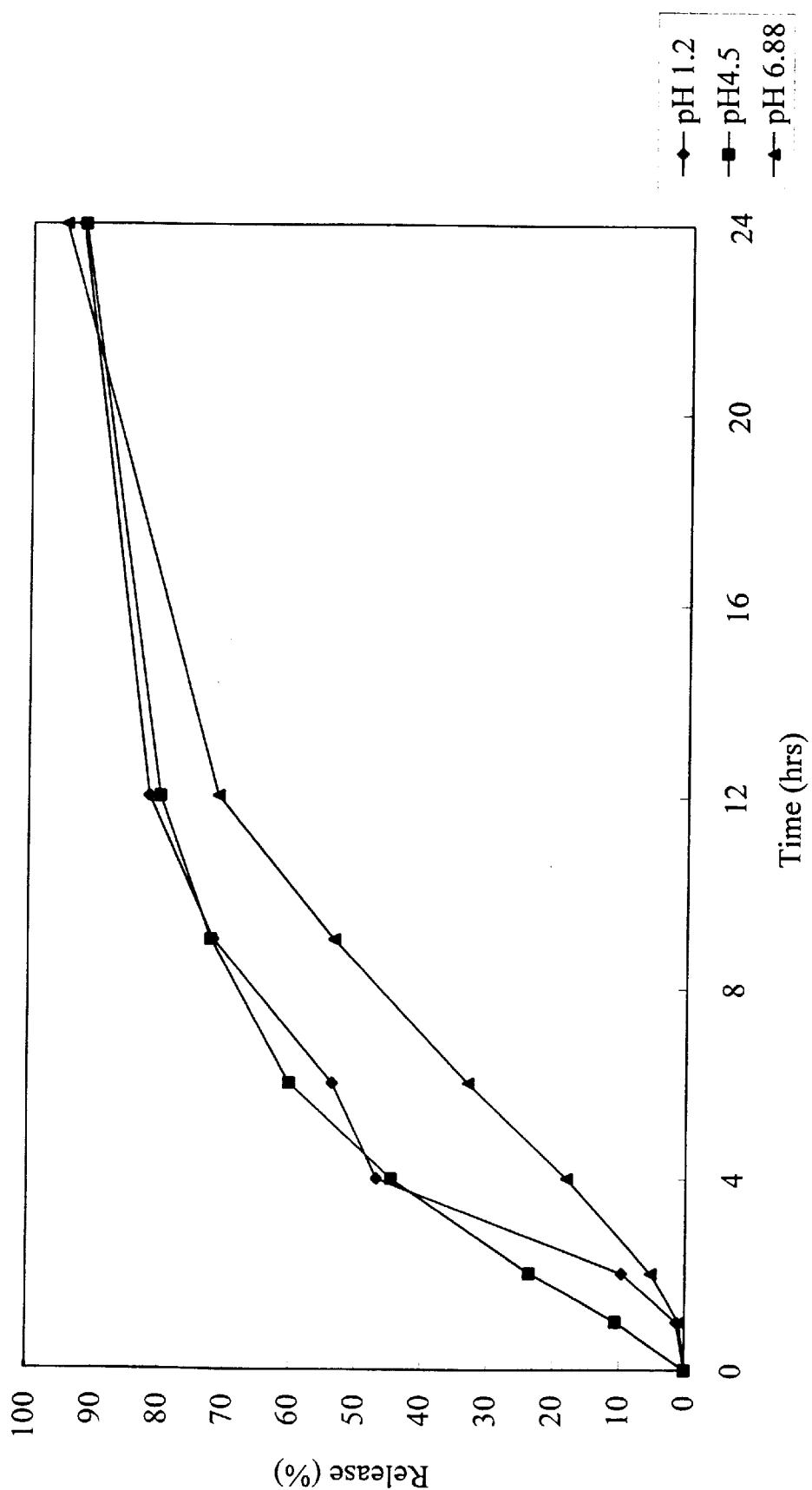
FIG. 19 depicts the dissolution curves of release-controlling-film coated pellets F-39 (310.7 mg) at pH 1.2 (—◆—), 4.5 (—■—) and 6.88 (—▲—).
Figure 20:
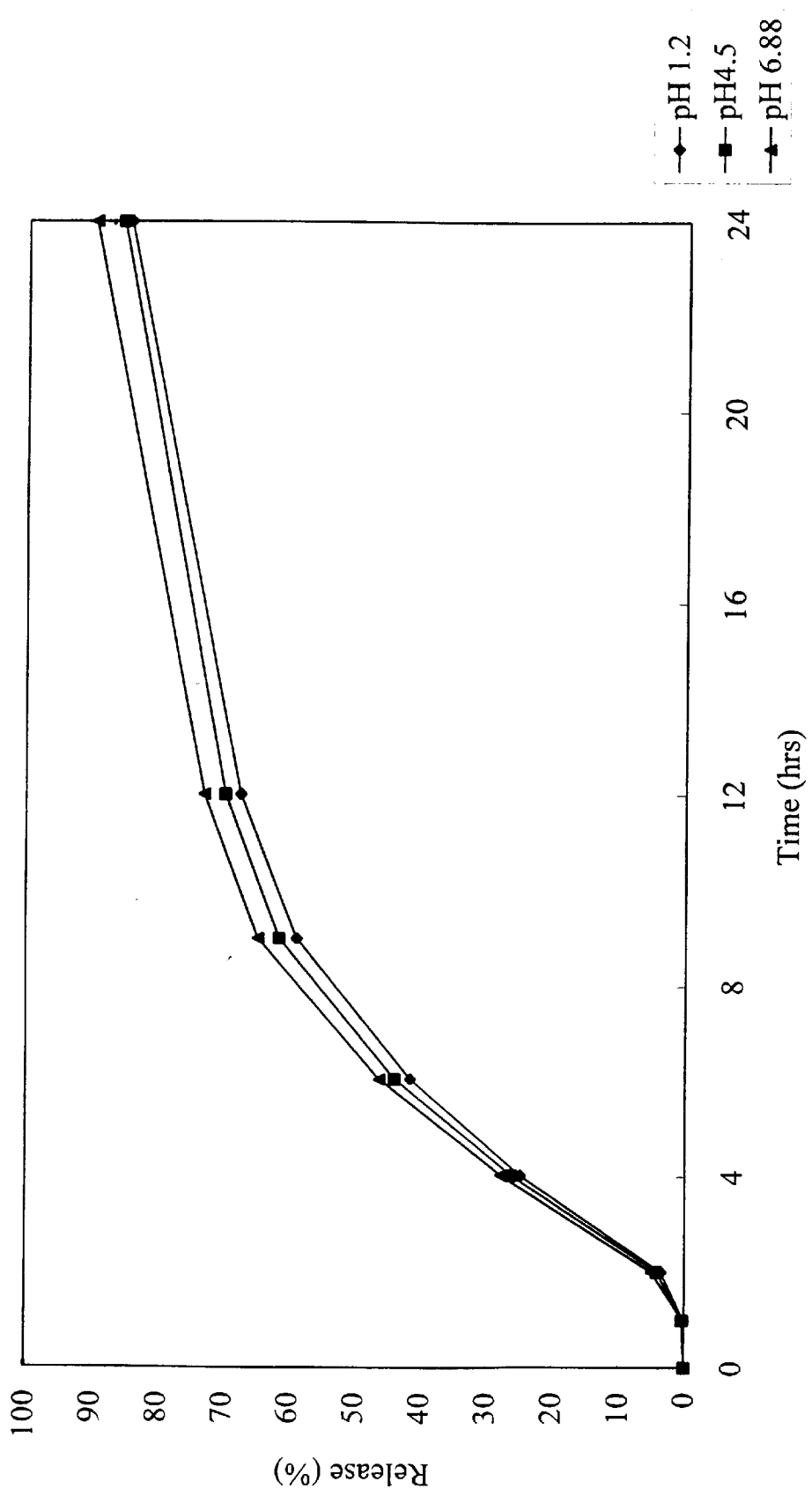
FIG. 20 depicts the dissolution curves of release-controlling-film coated pellets F-40 (263.85 mg) at pH 1.2 (—♦—), 4.5 (—■—) and 6.88 (—▲—).
Figure 21:
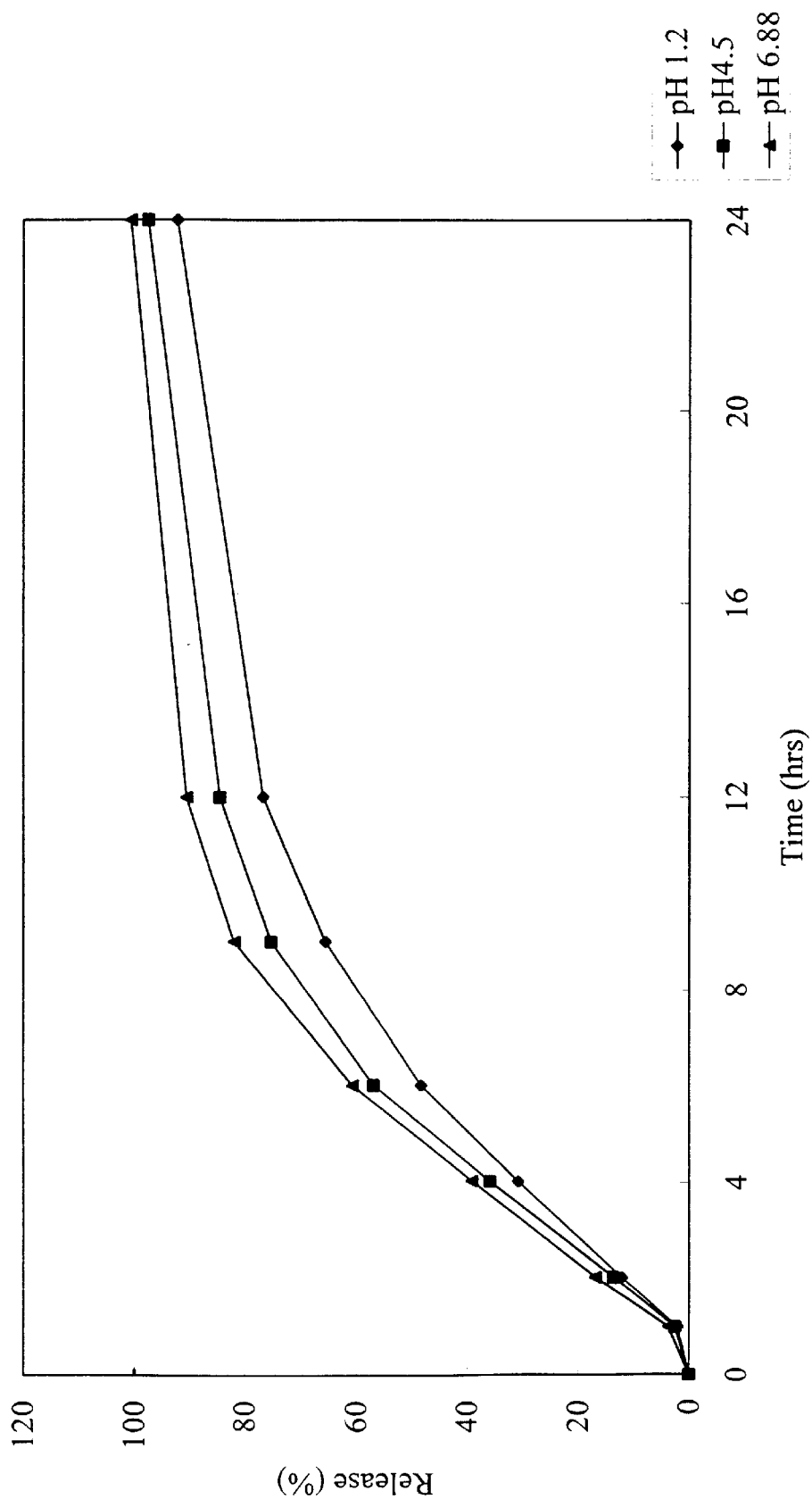
FIG. 21 depicts the dissolution curves of release-controlling-film coated pellets F-41 (252.7 mg) at pH 1.2 (—♦—), 4.5 (—■—) and 6.88 (—▲—).
Figure 22:
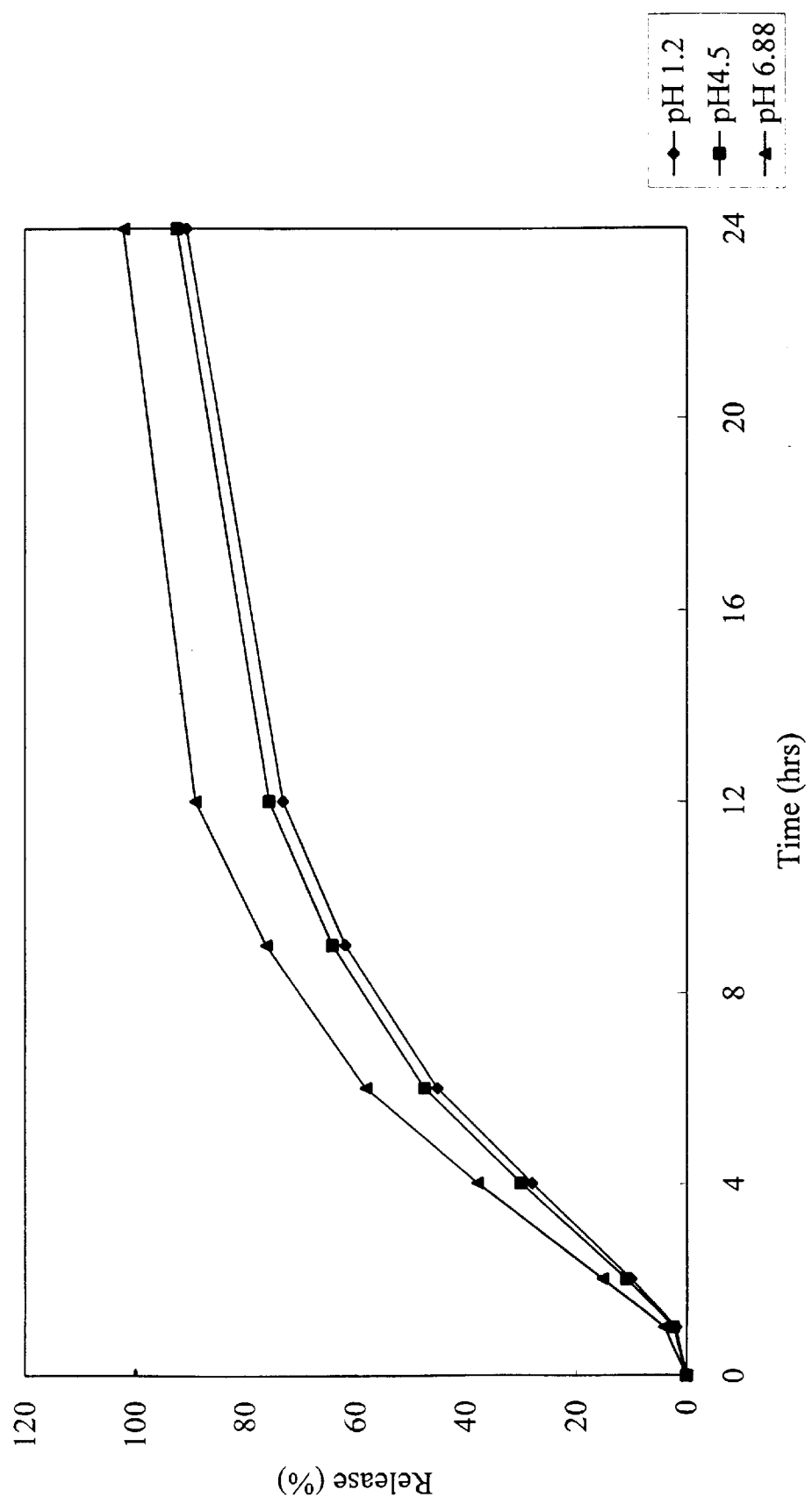
FIG. 22 depicts the dissolution curves of release-controlling-film coated pellets F-42 (253.33 mg) at pH 1.2 (—♦—), 4.5 (—■—) and 6.88 (—▲—).
Figure 23:
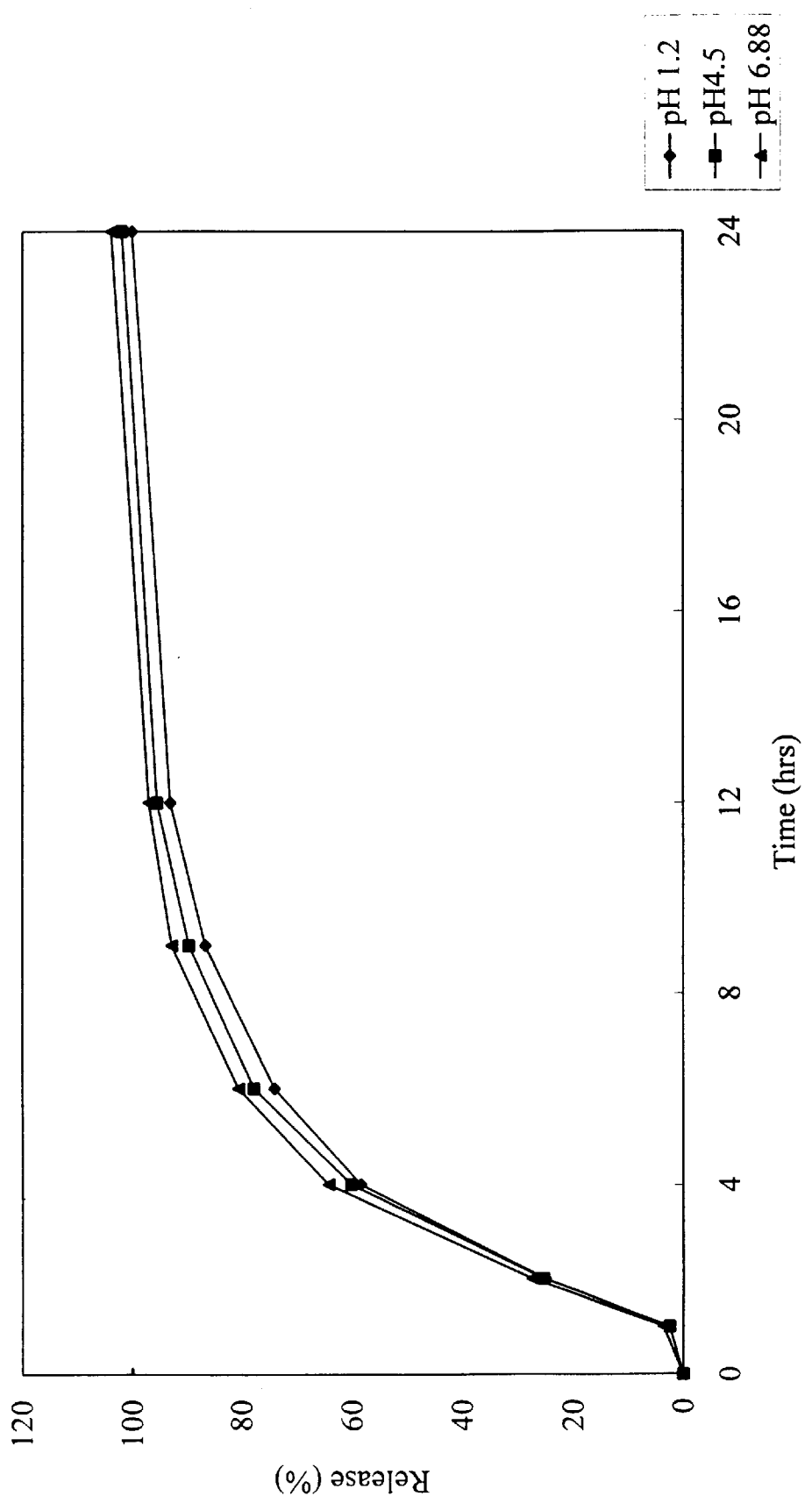
FIG. 23 depicts the dissolution curves of release-controlling-film coated pellets F-43 (267.22 mg) at pH 1.2 (—♦—), 4.5 (—■—) and 6.88 (—▲—).
Figure 24:
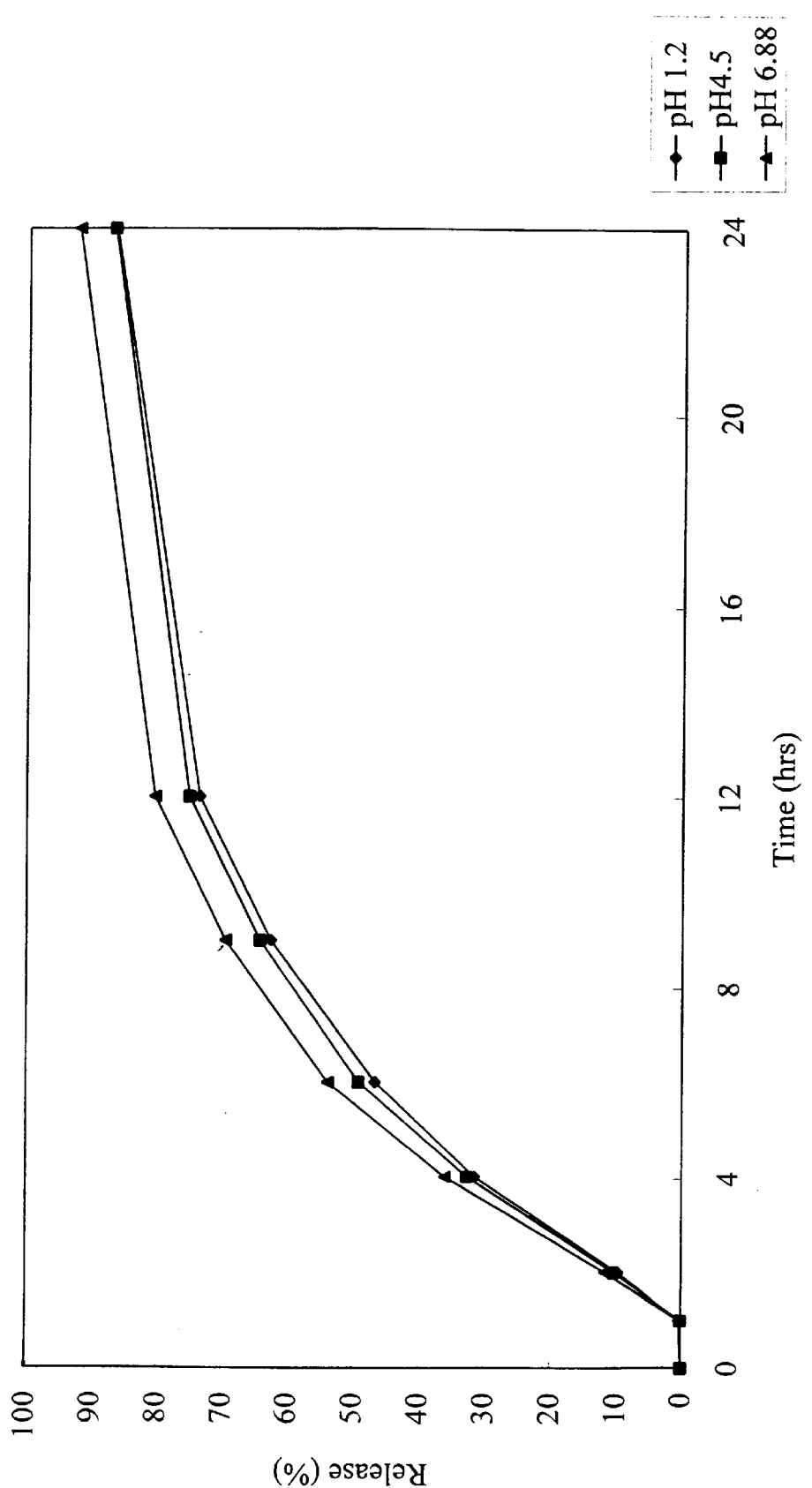
FIG. 24 depicts the dissolution curves of release-controlling-film coated pellets F-45 (254.18 mg) at pH 1.2 (—♦—), 4.5 (—■—) and 6.88 (—▲—).
Figure 25:
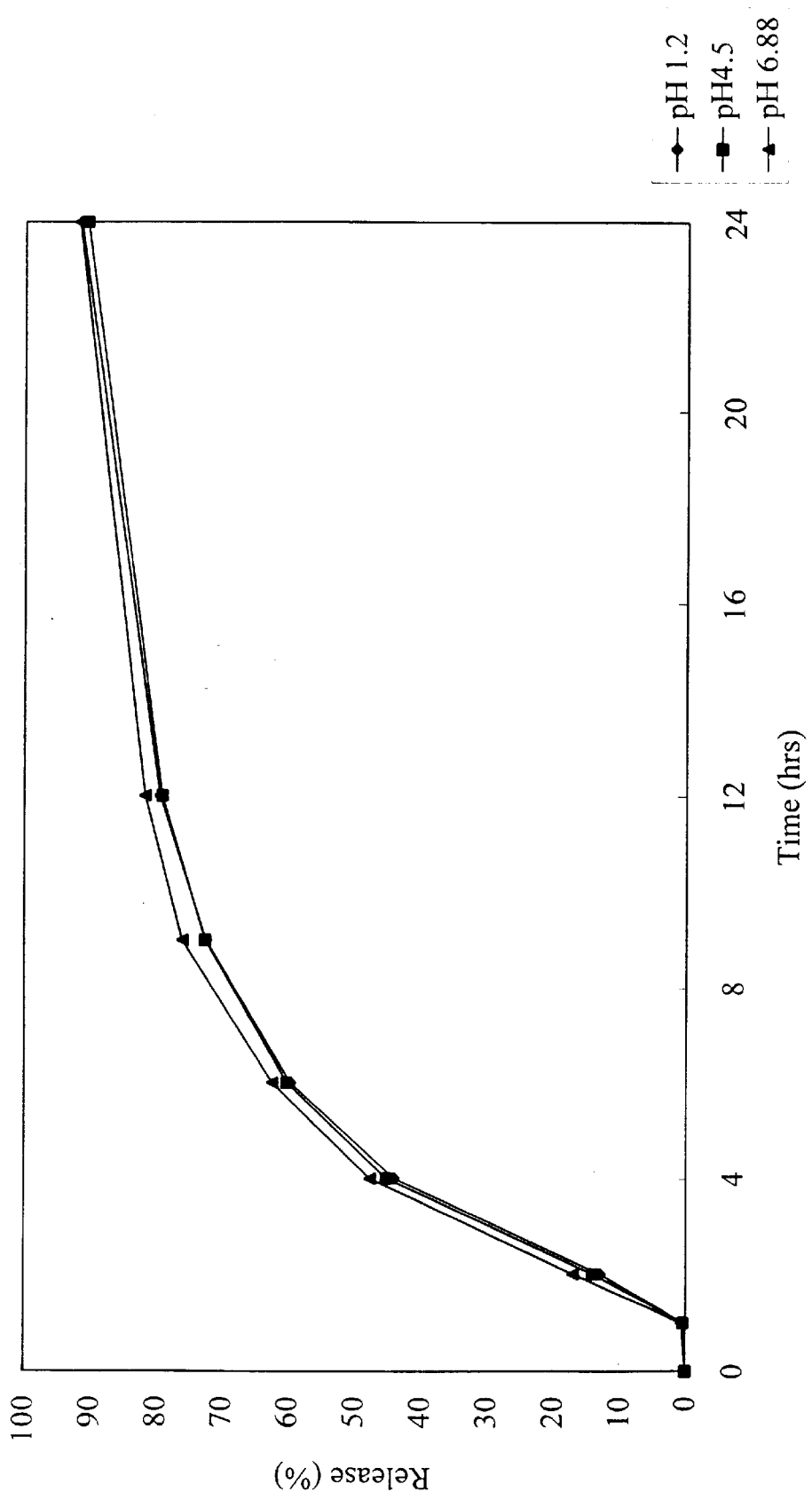
FIG. 25 depicts the dissolution curves of release-controlling-film coated pellets F-46 (253.33 mg) at pH 1.2 (—♦—), 4.5 (—■—) and 6.88 (—▲—).
Figure 26:
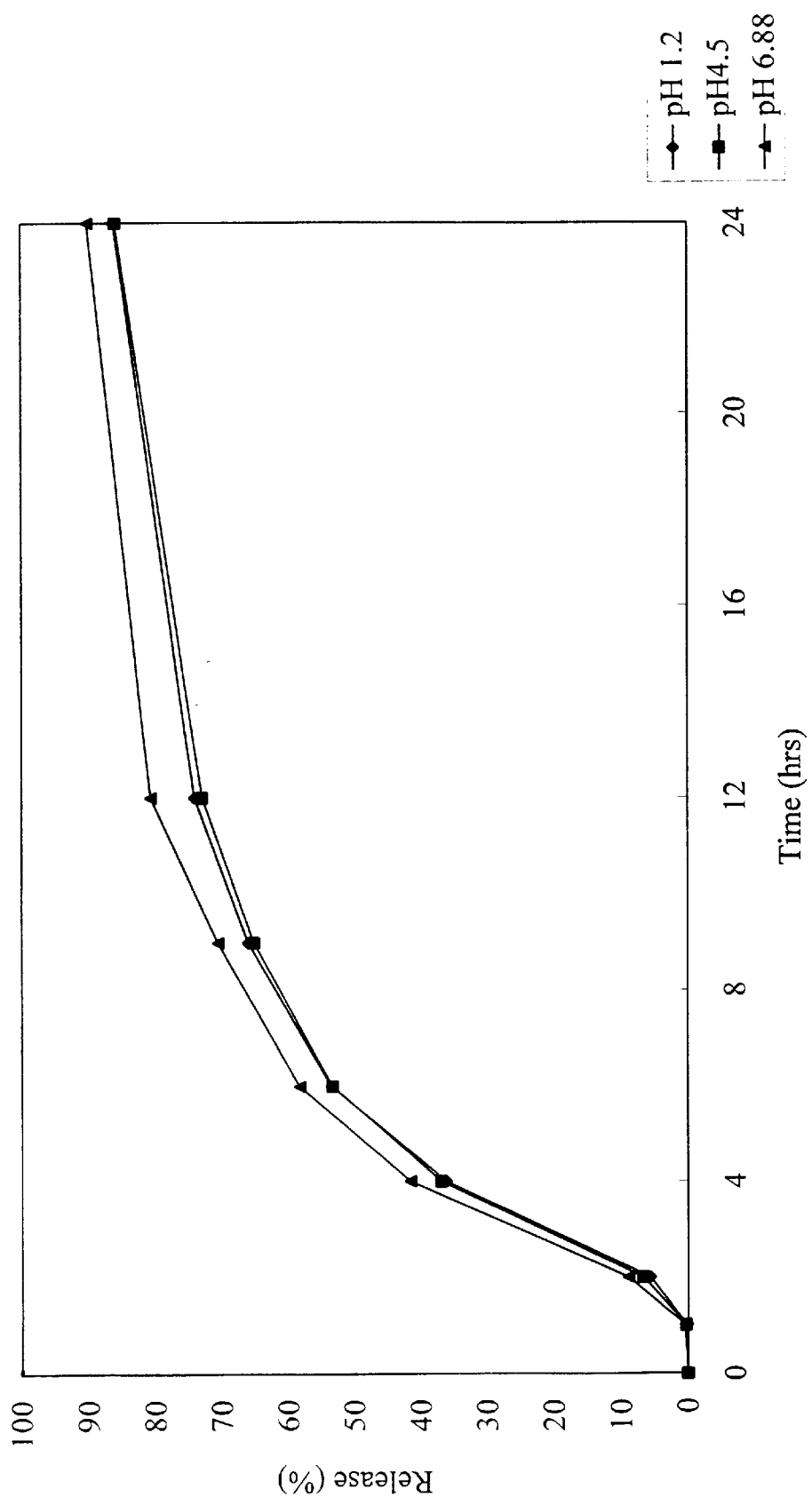
FIG. 26 depicts the dissolution curves of release-controlling-film coated pellets F-48 (249 mg) at pH 1.2 (—♦—), 4.5 (—■—) and 6.88 (—▲—).
Figure 27:
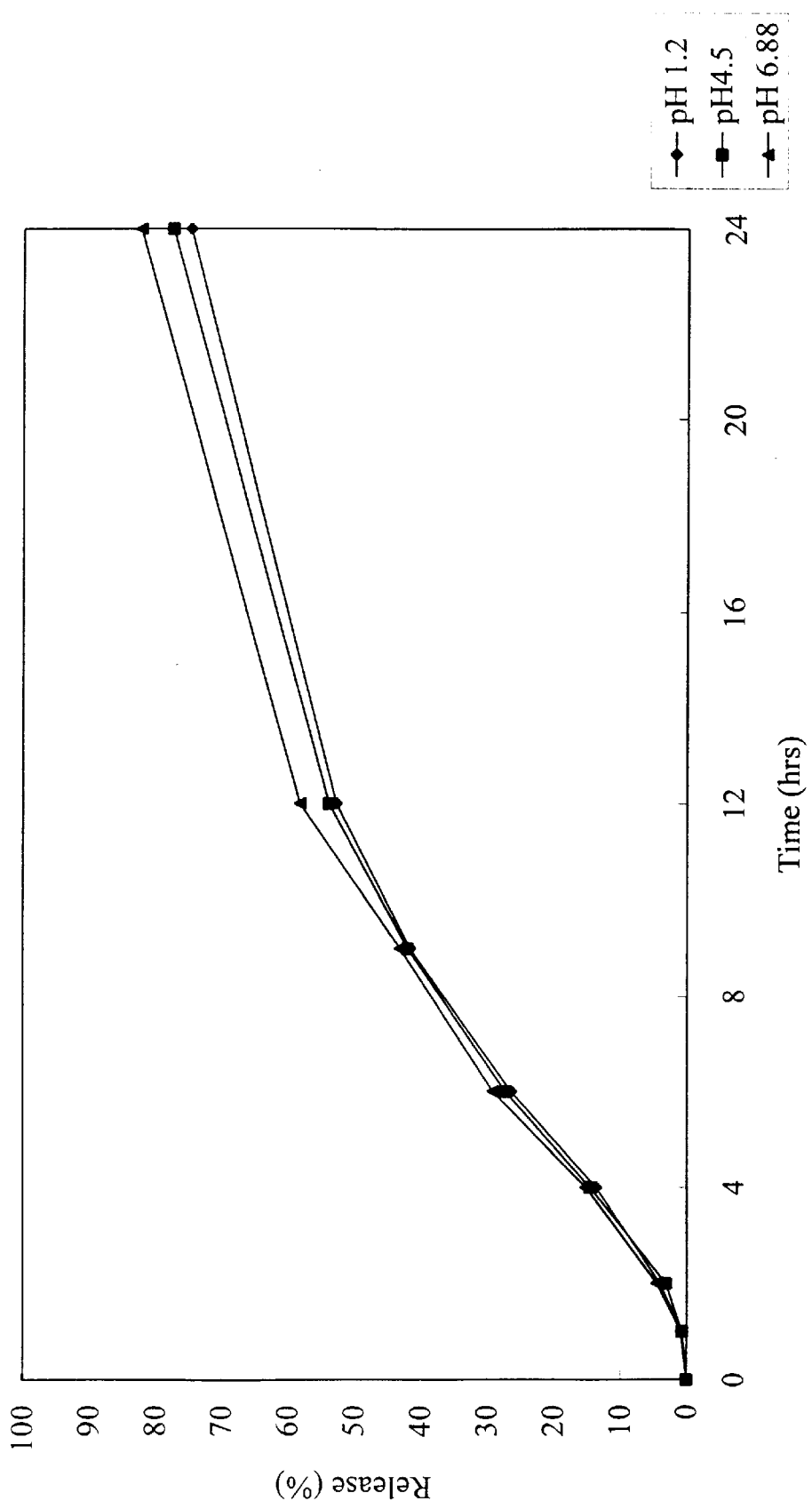
FIG. 27 depicts the dissolution curves of release-controlling-film coated pellets F-49 (253.33 mg) at pH 1.2 (—♦—), 4.5 (—■—) and 6.88 (—▲—).
Figure 28:
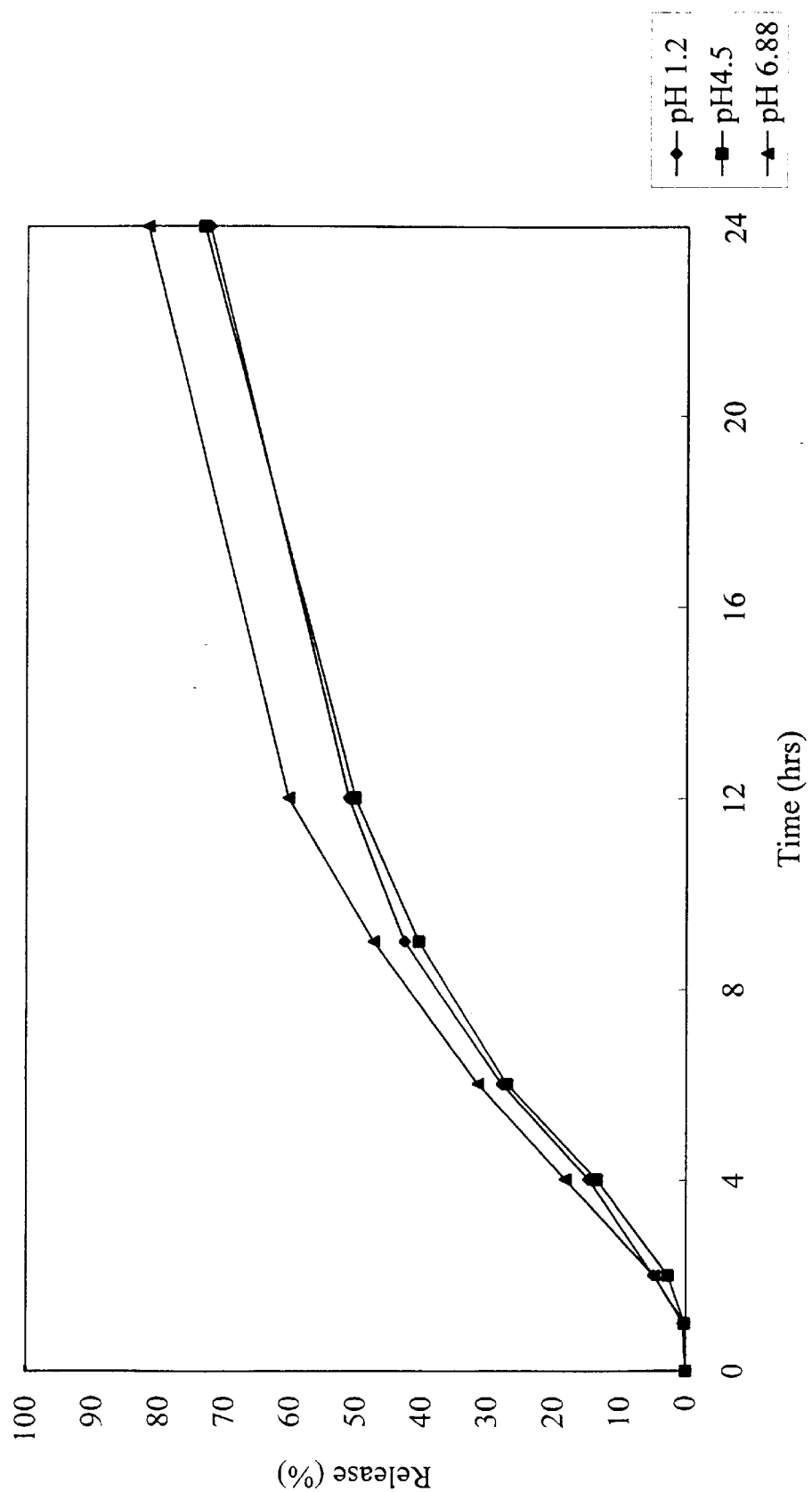
FIG. 28 depicts the dissolution curves of release-controlling-film coated pellets F-50 (250 mg) at pH 1.2 (—♦—), 4.5 (—■—) and 6.88 (—▲—).
Figure 29:
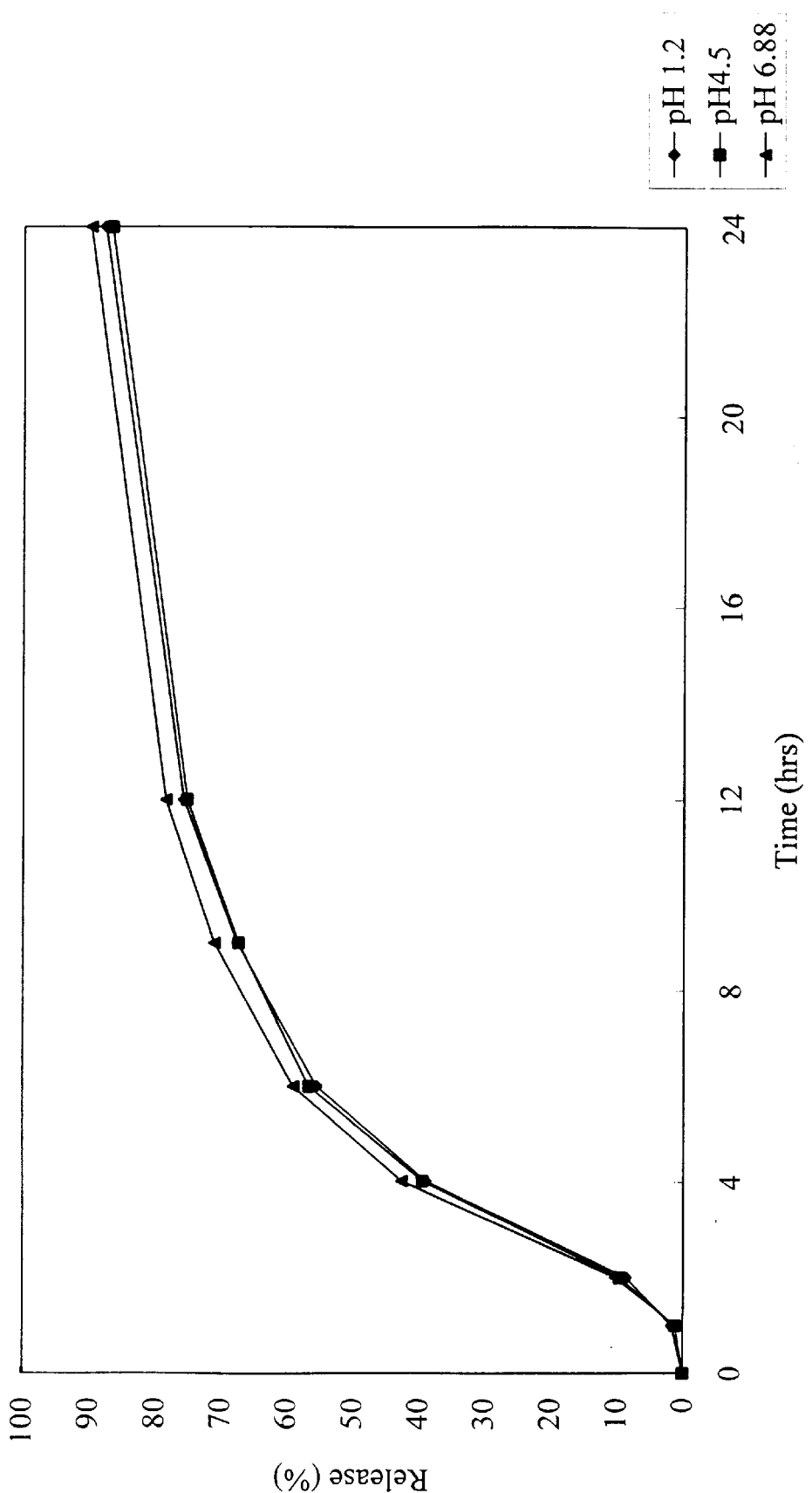
FIG. 29 depicts the dissolution curves of release-controlling-film coated pellets F-51 (250 mg) at pH 1.2 (—♦—), 4.5 (—■—) and 6.88 (—▲—).
Figure 30:
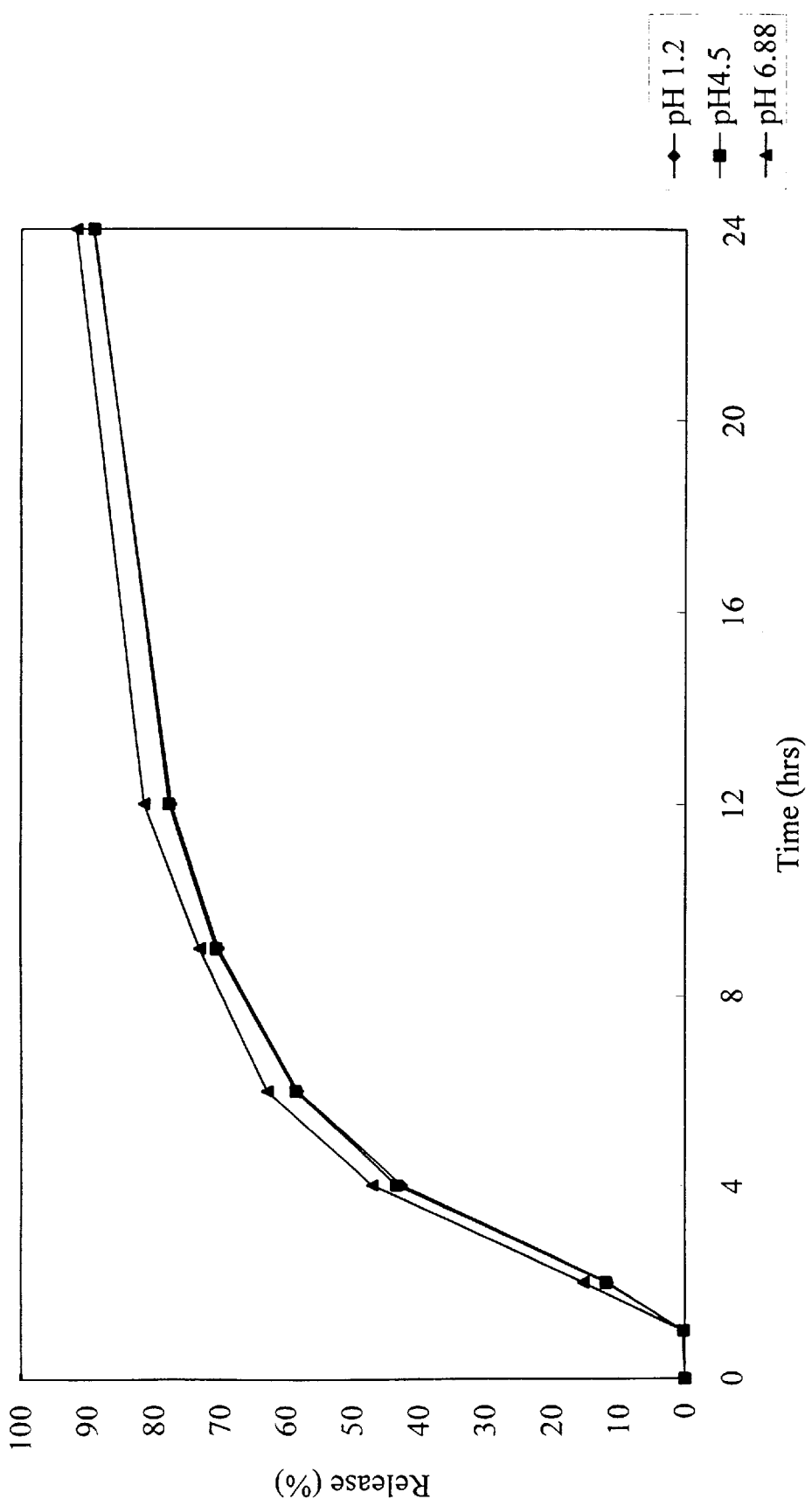
FIG. 30 depicts the dissolution curves of release-controlling-film coated pellets F-52 (250 mg) at pH 1.2 (—♦—), 4.5 (—■—) and 6.88 (—▲—).
Figure 31:
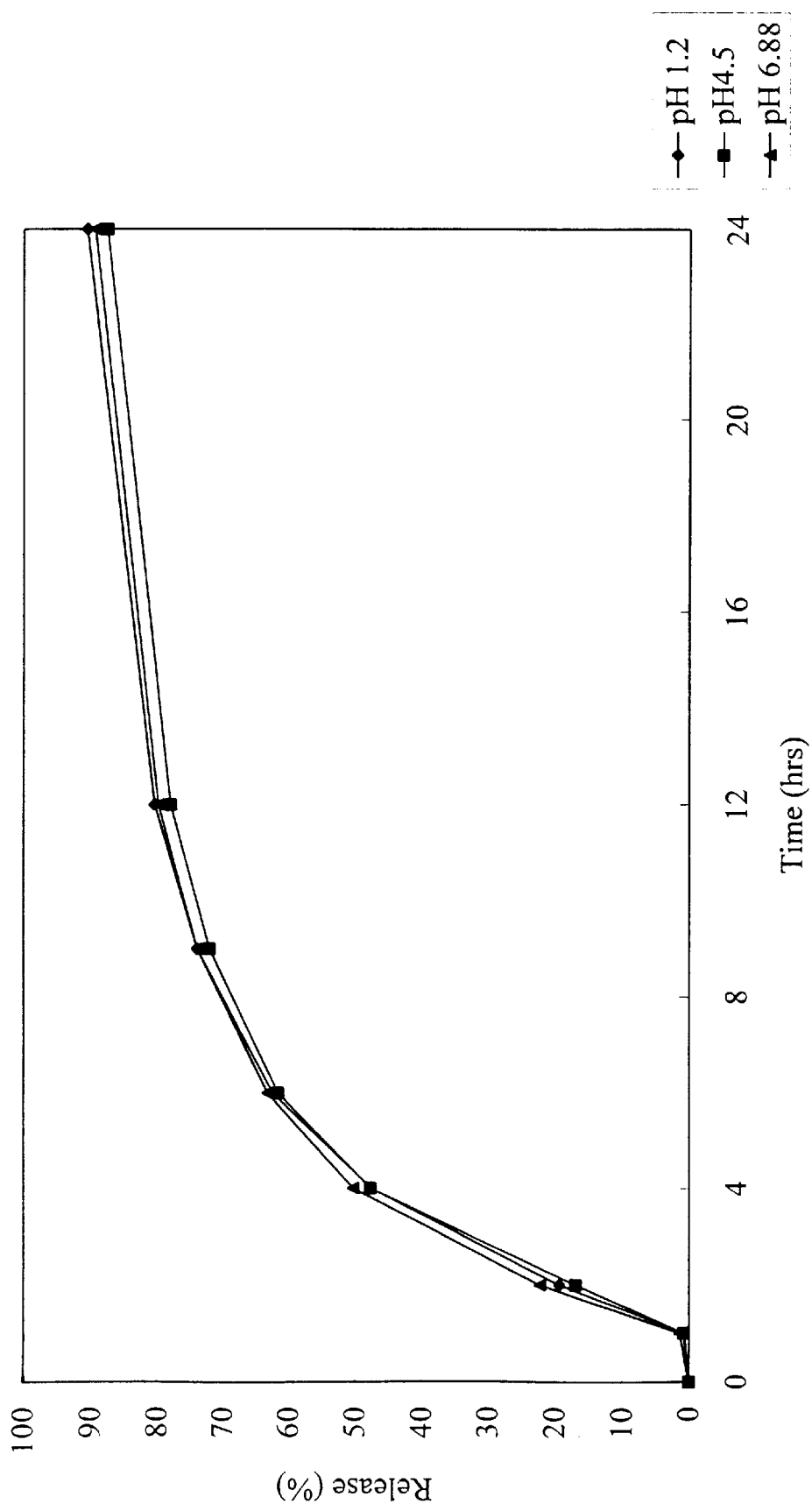
FIG. 31 depicts the dissolution curves of release-controlling-film coated pellets F-53 (250 mg) at pH 1.2 (—♦—), 4.5 (—■—) and 6.88 (—▲—).
Figure 32:
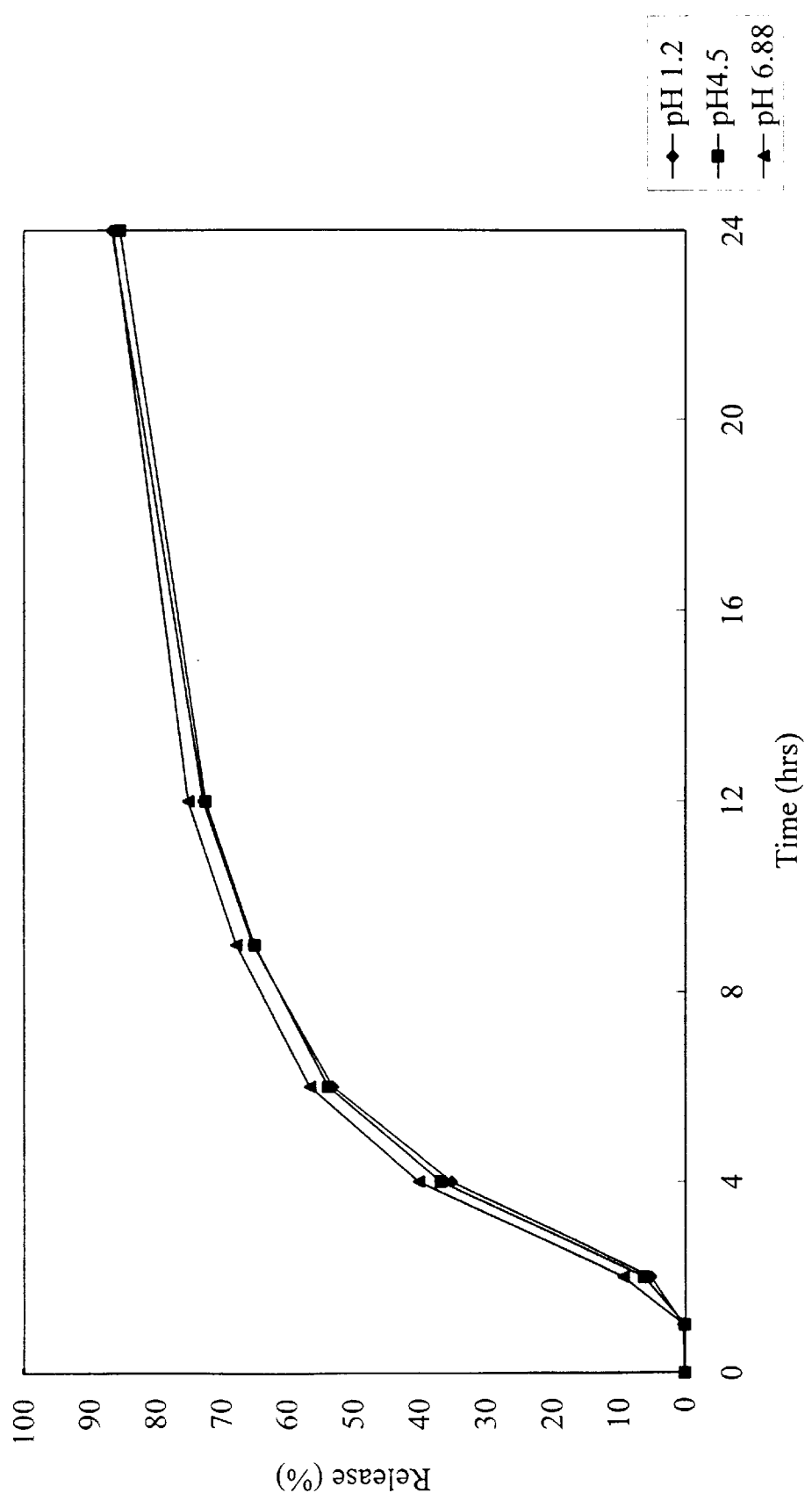
FIG. 32 depicts the dissolution curves of release-controlling-film coated pellets F-54 (250 mg) at pH 1.2 (—♦—), 4.5 (—■—) and 6.88 (—▲—).
Figure 33:
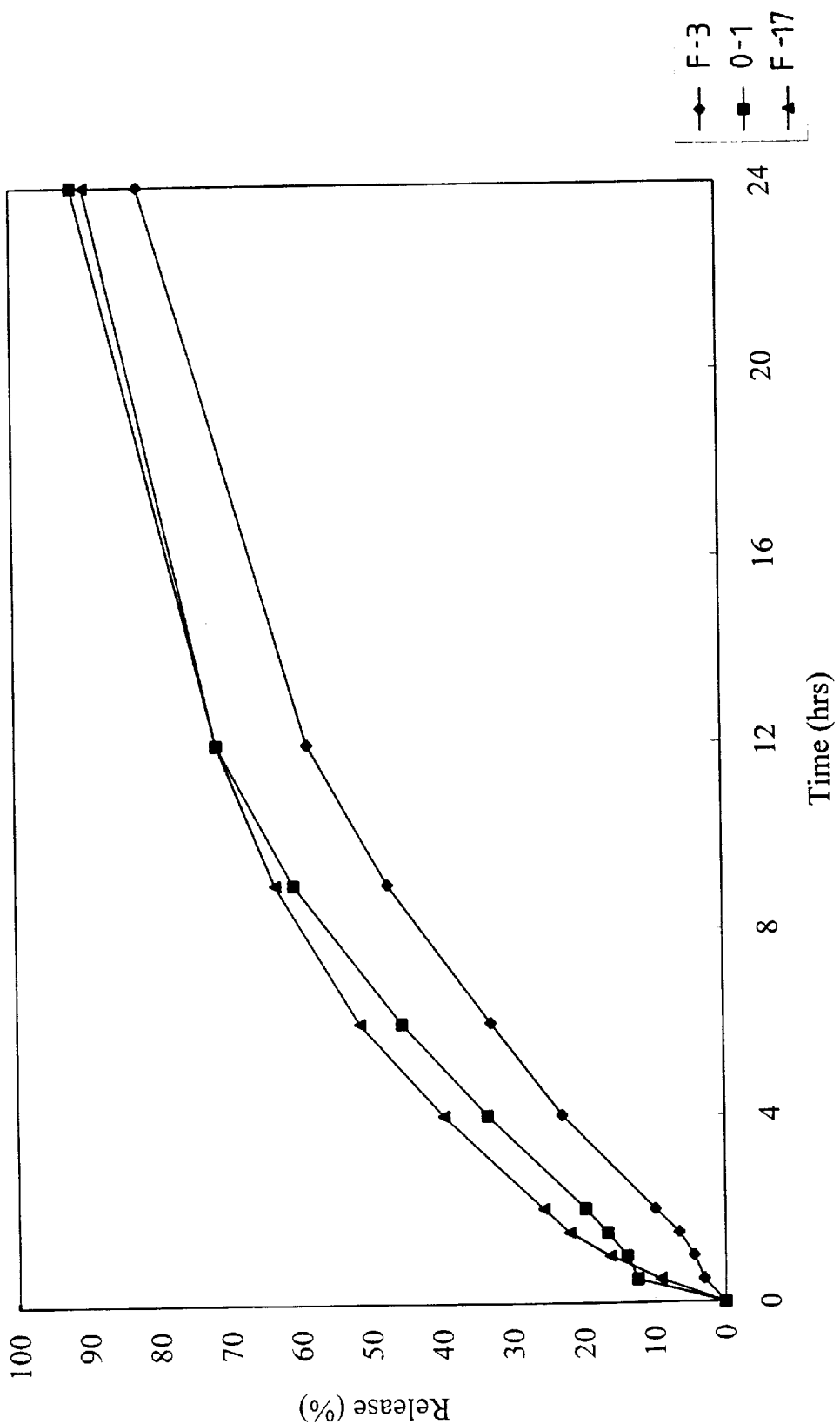
FIG. 33 depicts the dissolution curves of release-controlling-film coated pellets F-3 (—♦—) and F-17 (—▲—), and controlled release dosage form O-1 (—■—).
Figure 34:
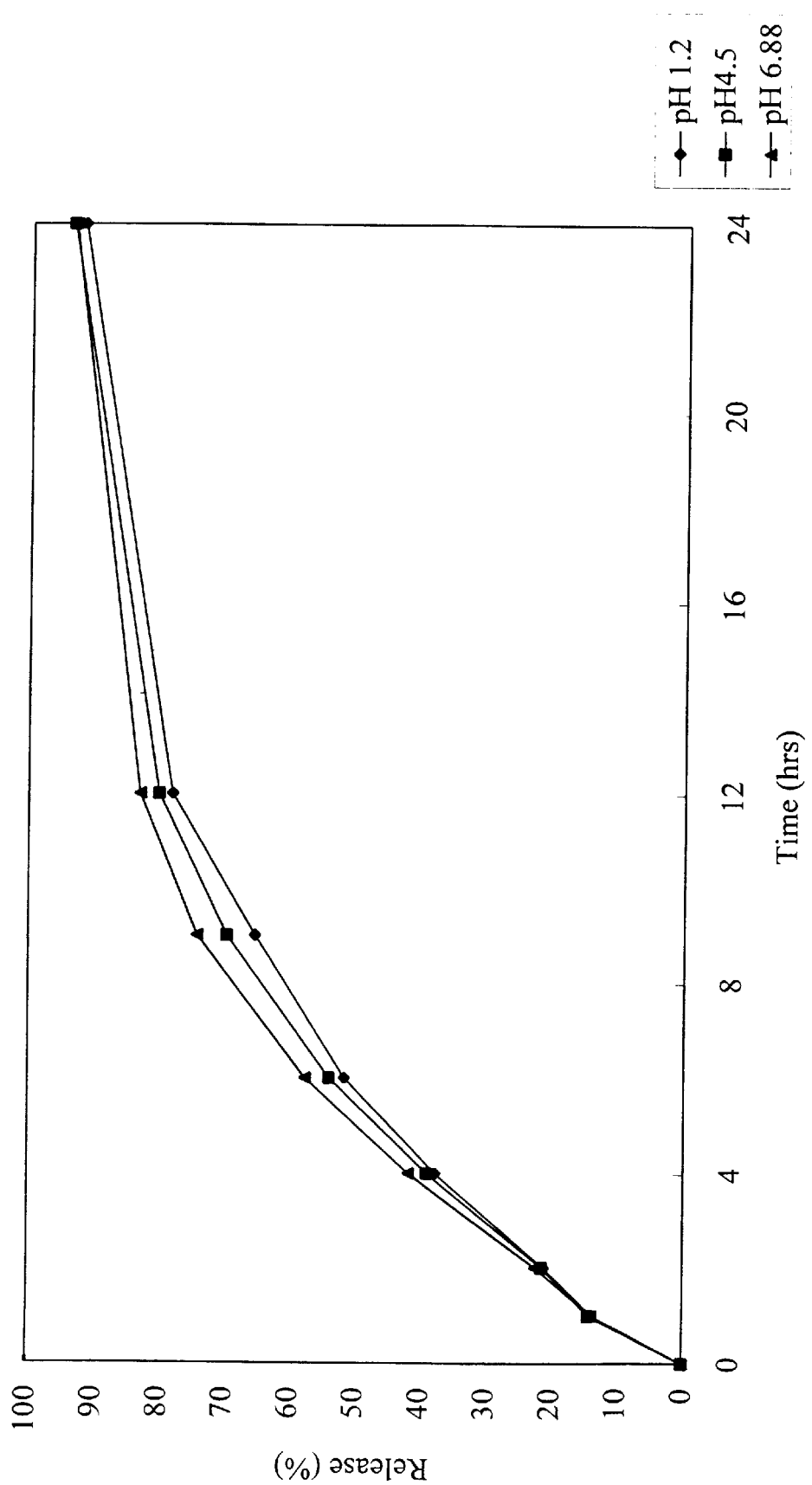
FIG. 34 depicts the dissolution curves of controlled release dosage form O-1 (215 mg) at pH 1.2 (—♦—), 4.5 (—■—) and 6.88 (—▲—).
Figure 35:
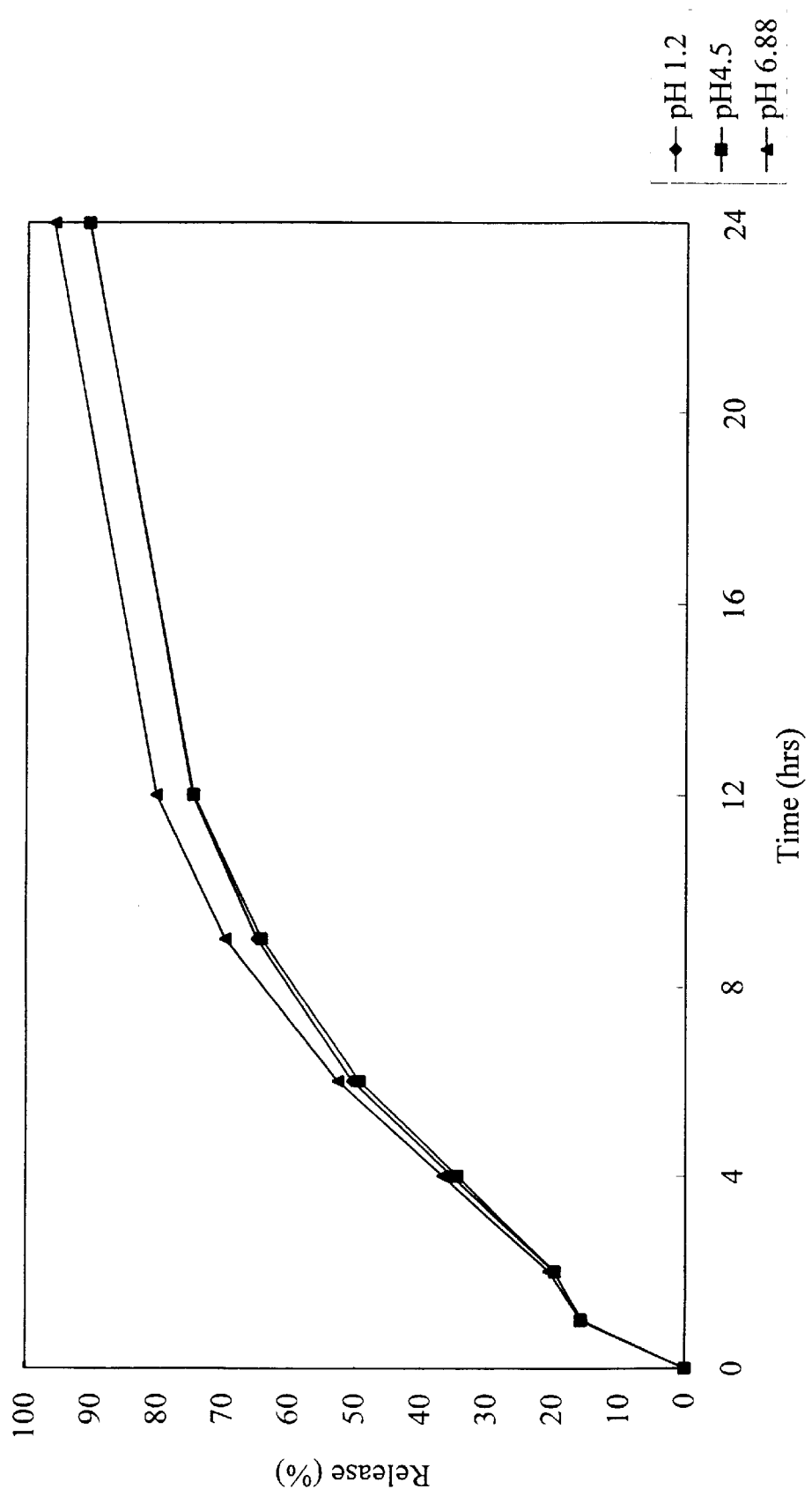
FIG. 35 depicts the dissolution curves of controlled release dosage form O-2 (218.77 mg) at pH 1.2 (—♦—), 4.5 (—■—) and 6.88 (—▲—).
Figure 36:
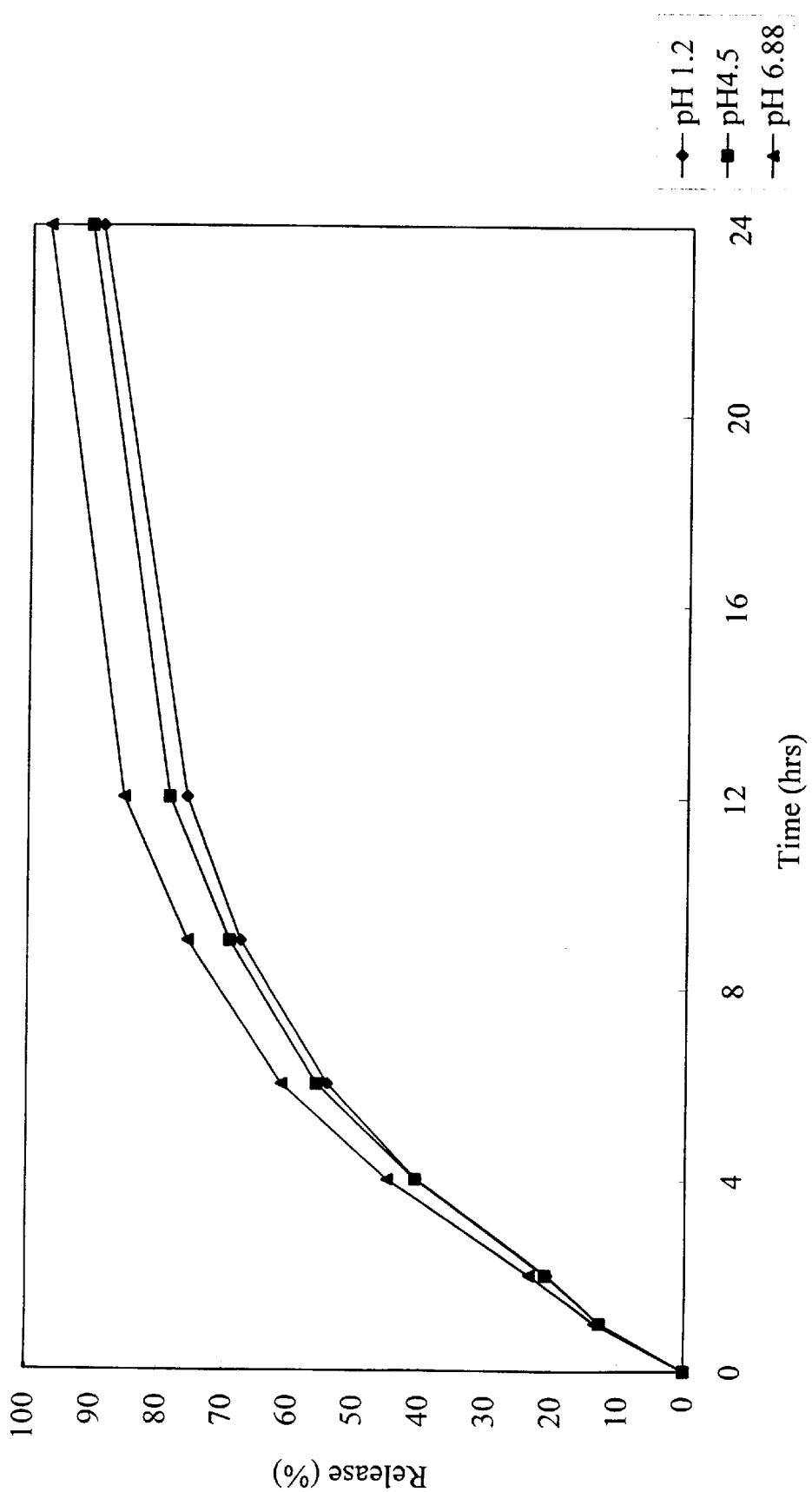
FIG. 36 depicts the dissolution curves of controlled release dosage form O-3 (233.8 mg) at pH 1.2 (—♦—), 4.5 (—■—) and 6.88 (—▲—).
Figure 37:
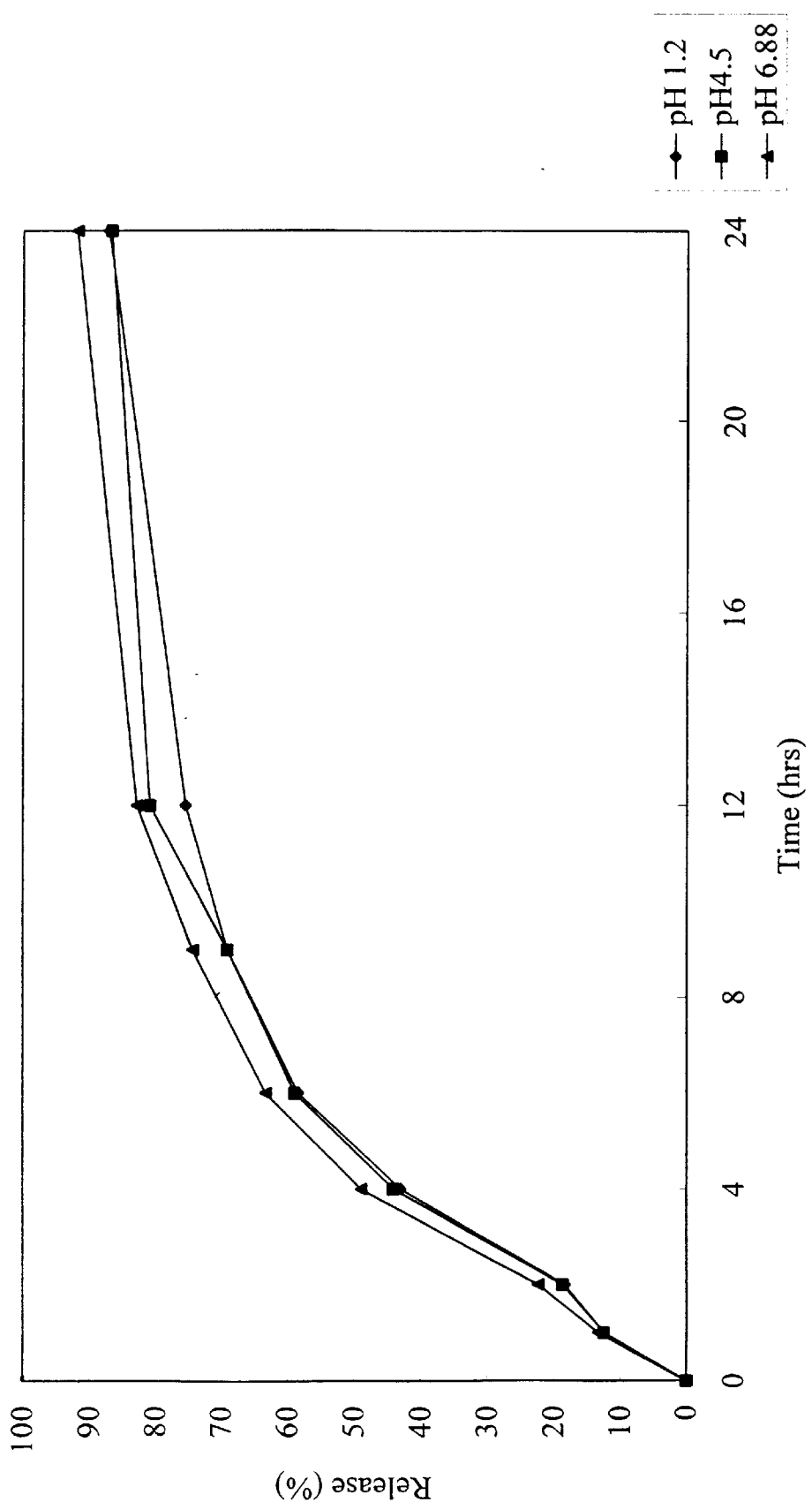
FIG. 37 depicts the dissolution curves of controlled release dosage form O-4 (232.7 mg) at pH 1.2 (—♦—), 4.5 (—■—) and 6.88 (—▲—).
Figure 38:
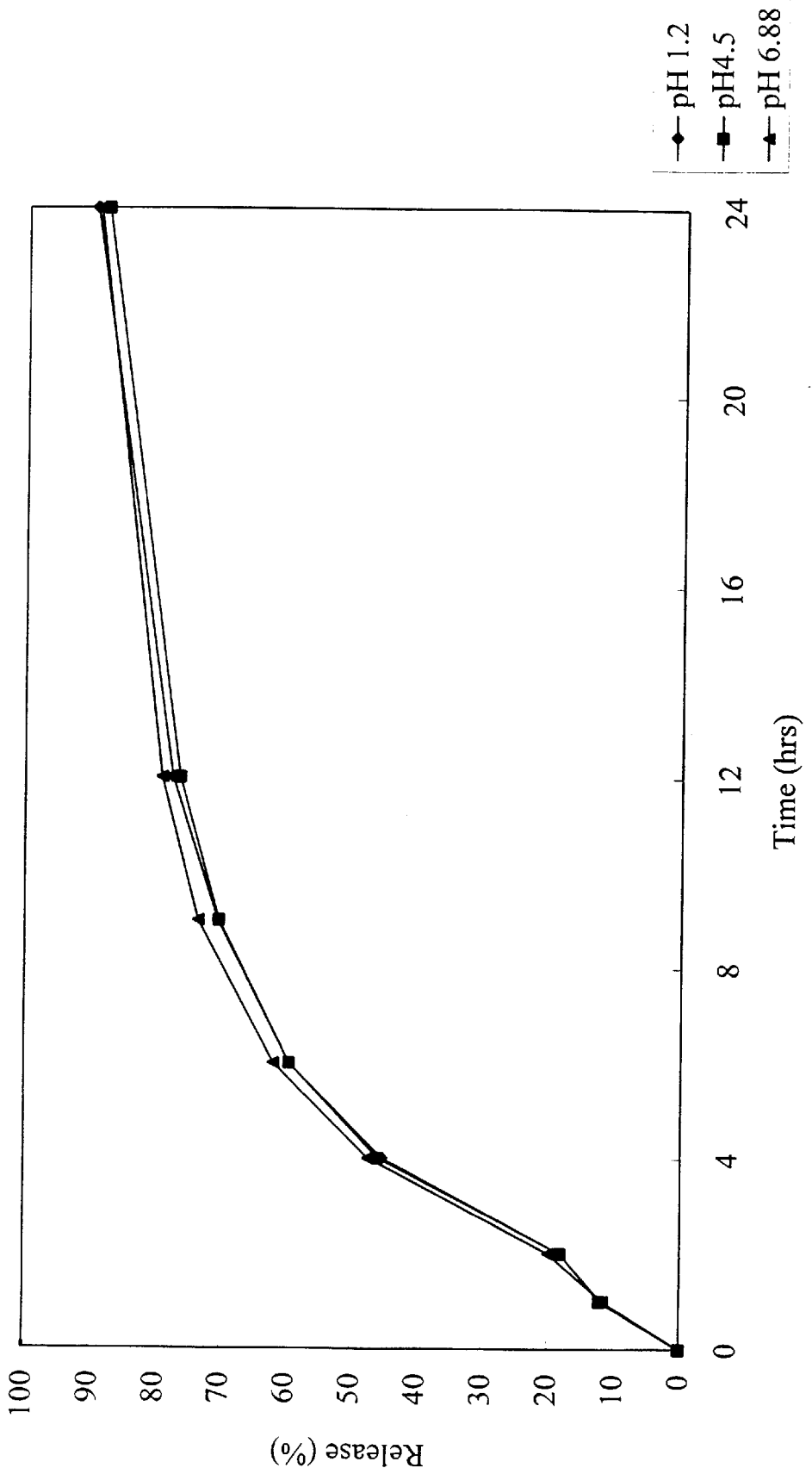
FIG. 38 depicts the dissolution curves of controlled release dosage form O-5 (230.3 mg) at pH 1.2 (—♦—), 4.5 (—■—) and 6.88 (—▲—).
Figure 39:
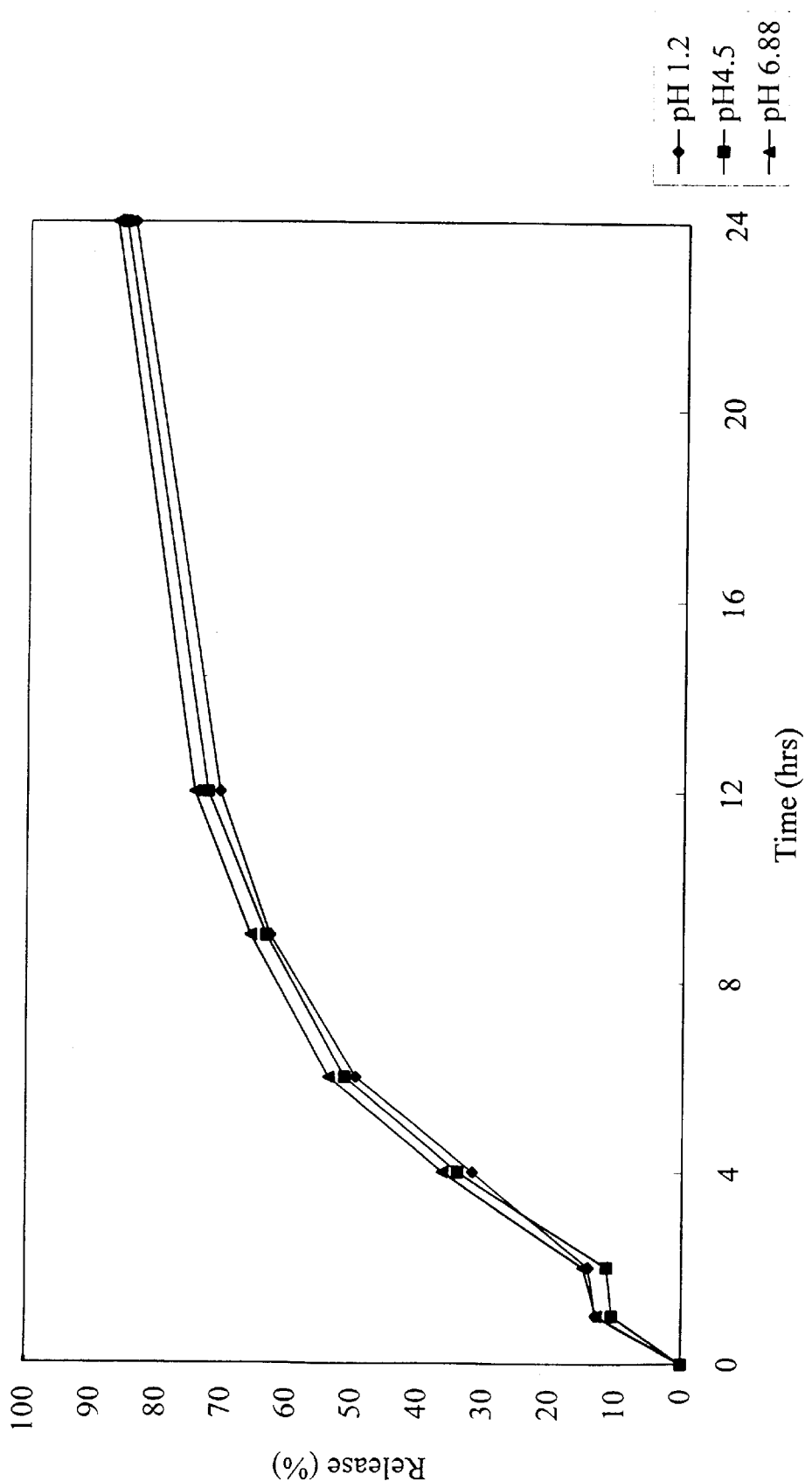
FIG. 39 depicts the dissolution curves of controlled release dosage form O-6 (230.3 mg) at pH 1.2 (—♦—), 4.5 (—■—) and 6.88 (—▲—).
Figure 40:
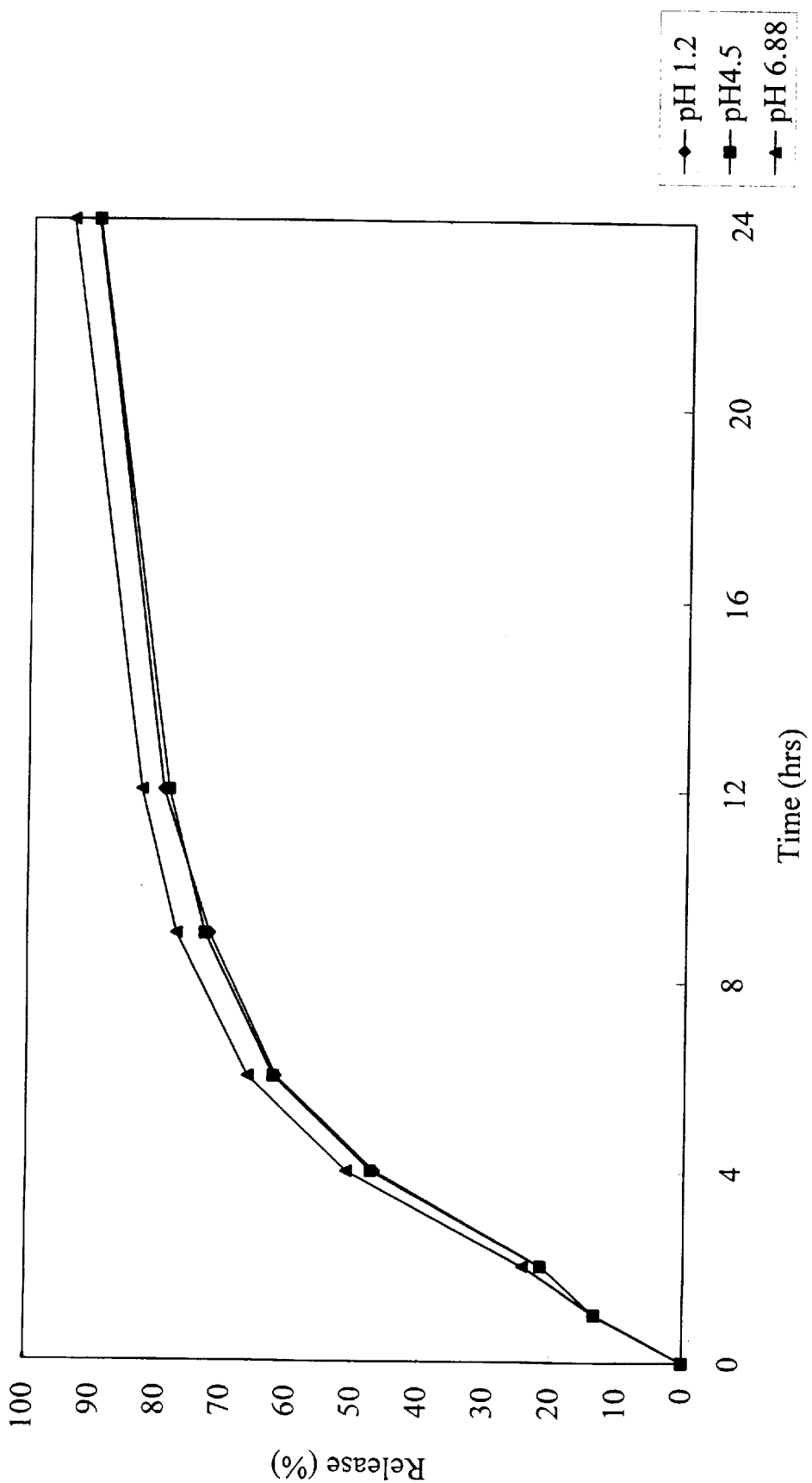
FIG. 40 depicts the dissolution curves of controlled release dosage form O-7 (230 mg) at pH 1.2 (—♦—), 4.5 (—■—) and 6.88 (—▲—).
Figure 41:
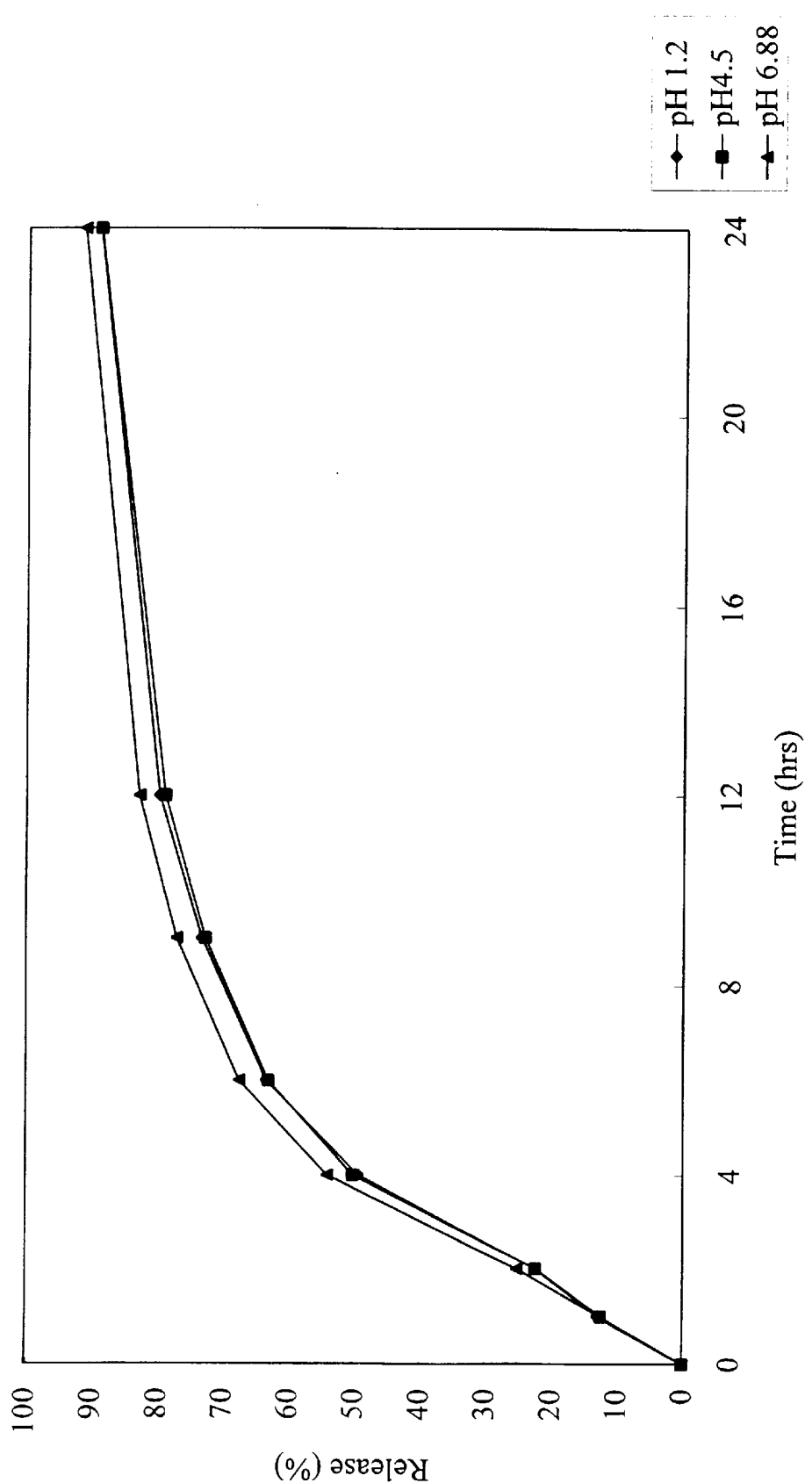
FIG. 41 depicts the dissolution curves of controlled release dosage form O-8 (230 mg) at pH 1.2 (—♦—), 4.5 (—■—) and 6.88 (—▲—).
Figure 42:
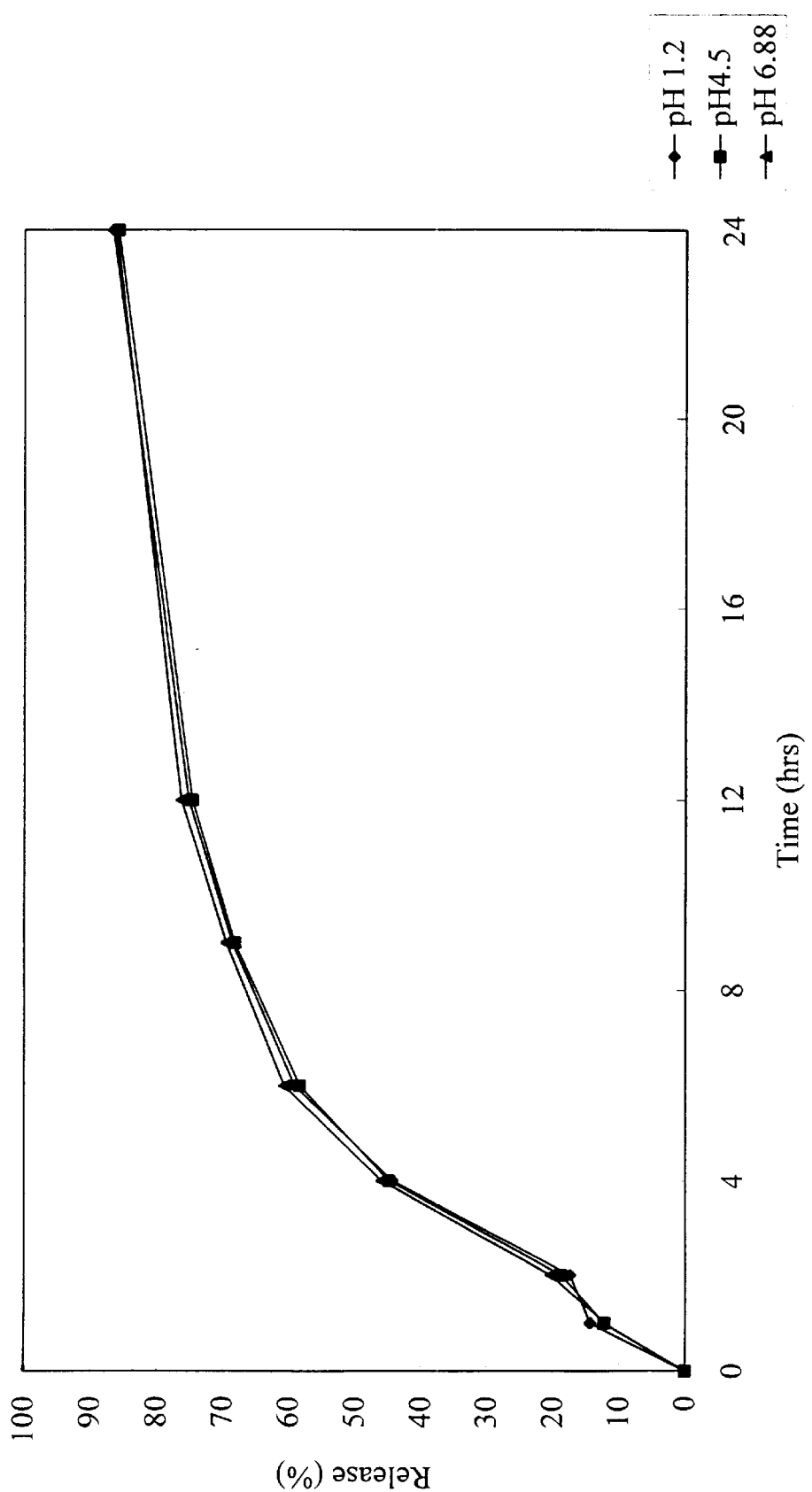
FIG. 42 depicts the dissolution curves of controlled release dosage form O-9 (230 mg) at pH 1.2 (—♦—), 4.5 (—■—) and 6.88 (—▲—).
Figure 43:
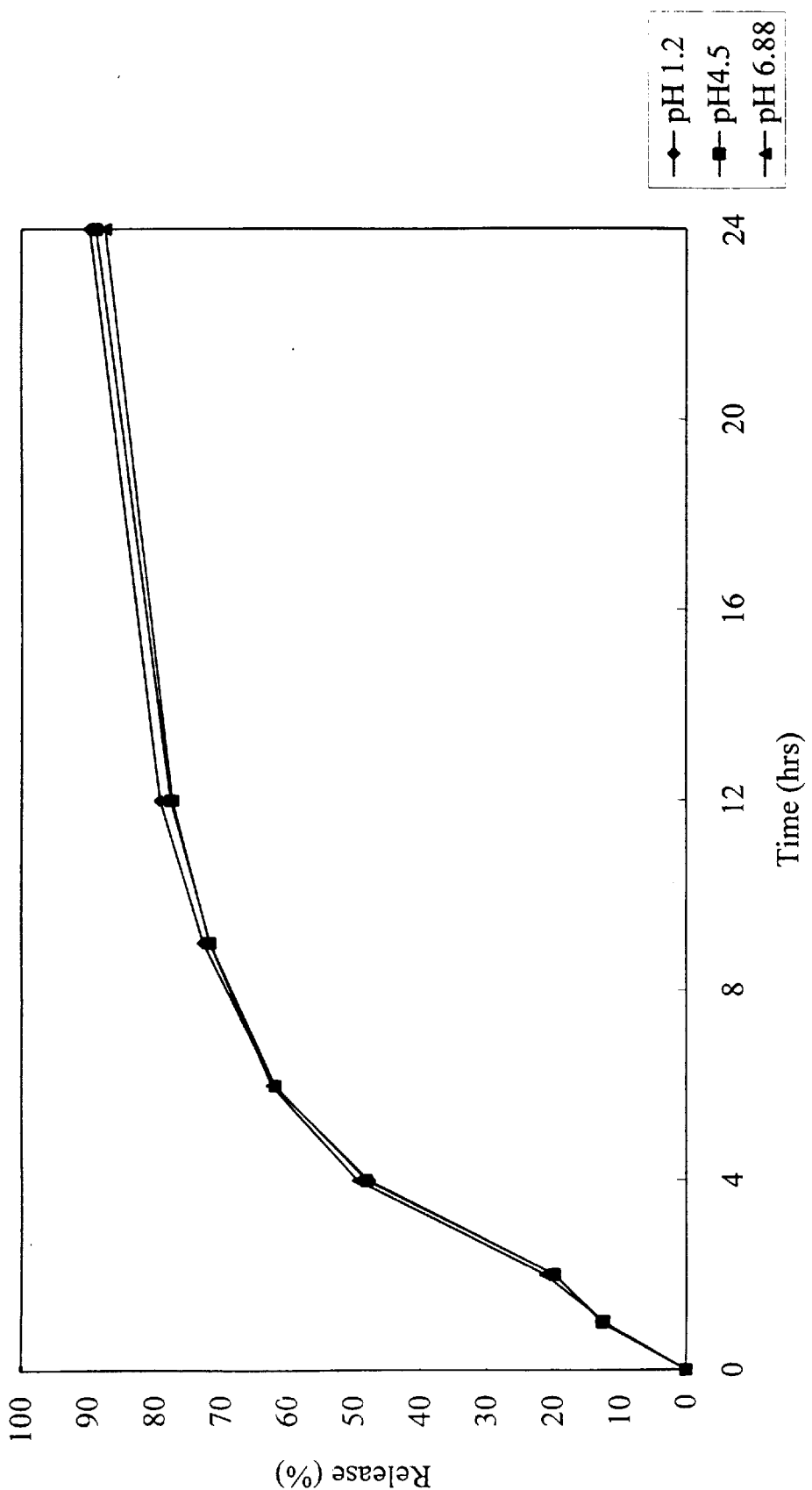
FIG. 43 depicts the dissolution curves of controlled release dosage form O-10 (230 mg) at pH 1.2 (—♦—), 4.5 (—■—) and 6.88 (—▲—).

The dissolution test on release-controlling-film-coated pellets and the release controlled dosage forms according to the invention was tested on standard USP No. 1 Dissolution Tester (Toyama, Sangoyo Co. Ltd., Japan). The tested pellets were stirred, 50 rpm, at 37° C. in deionized water or in HCl media (pH 1.2, 4.5 and 6.8). One ml of samples were diluted. filtered (PTFE, 13 mm, 0.45 $\mu$m), and quantitatively analyzed with UV-visible spectrophotometer (UV-160A, Shimadzu, Japan) at 240 nm at 0, 1, 2, 4, 6, 9, 12 and 24 hr. The accumulative percentages of dissolved Tacrine HCl were calculated. The results are shown in FIGS. 1 to 43.

The release-controlling layer in the controlled release dosage forms of the invention effectively controls the inner active layer to release suitable amount of tacrine for at least 24 hours. In addition, the controlled release dosage forms of the invention immediately release suitable amount of tacrine upon administration and continue the release for at least 24 hours.

EXAMPLE 7

Bioavailability Test

Dogs (weighed 17 to 20 Kg and aged 18 months) are kept in a temperature-and-humidity controlled animal room, and fasted overnight. On the day of test, the dogs are given the tested dosage forms (60 mg tacrine/capsule), and then water (30 ml). Blood samples are withdrawn immediately before and 0.5, 1, 2, 3, 4, 6, 8, 10, 12, 15, 16, 18, 21 and 24 hours after administration. Parameters such as apparent volume of distribution divided by bioavailability (Vd/F), first order absorption rate constant (Ka), first order elimination rate constant (kel), area under the blood concentration versus time curve (AUC), half-life ($t_{1/2}$) clearance, maximum concentration ($C_{max}$) and time to peak concentration ($T_{peak}$) are determined in accordance with Bourne, D. W. A., "Boomer, a Simulation and Modeling Program for Pharmacokinetic and Pharmacodynamic Data Analysis," Computer Method Prog. Biomed, 29, 191–195 (1989).

What is claimed is:

1. A controlled release tacrine dosage form comprising a multi-layered pellet or pellets comprising:

(a) a core;

(b) an inner active layer comprising tacrine and a binder;

(c) a release-controlling layer comprising one or more release-controlling film-forming polymer; and (d) an active overcoat comprising tacrine and a binder.

2. The controlled release dosage form of claim 1 wherein the core is a non-pareil seed.

3. The controlled release dosage form of claim 1 wherein the binder is selected from the group consisting of polyvinylpyrrolidone, acacia, gelatin, glucose, guar gum, pregelatinized starch, sodium alginate, cellulose derivatives, and mixtures thereof.

4. The controlled release dosage form of claim 3 wherein the binder is a cellulose derivative selected from the group consisting of ethylcellulose, hydroxypropylcellulose, hydroxypropylmethylcellulose, methylcellulose, sodium carboxymethylcellulose, and mixtures thereof.

5. The controlled release dosage form of claim 4 wherein the cellulose derivative is hydroxypropylmethylcellulose.

6. The controlled release dosage form of claim 1 wherein the release-controlling-film-forming polymer is selected from the group consisting of water insoluble polymers, water soluble polymers, enteric polymers, and mixtures thereof.

7. The controlled release dosage form of claim 6 wherein the release-controlling-film-forming polymer is a water insoluble polymer selected from the group consisting of cellulose derivatives, acrylic polymers, polyvinyl acetate, polyvinyl chloride, polyethylene, and mixtures thereof.

8. The controlled release dosage form of claim 7 wherein the cellulose derivative is ethylcellulose.

9. The controlled release dosage form of claim 7 wherein the acrylic polymers is selected from the group consisting of polyacrylamide, polyacryl dextrin, polyalkylcyanoacrylate, polymethylmethacrylate, methacrylic resin copolymers, and mixtures thereof.

10. The controlled release dosage form of claim 6 wherein the release-controlling-film-forming polymer is a water soluble polymer selected from the group consisting of hydroxycellulose, hydroxypropylmethylcellulose, carboxymethylcellulose, and mixtures thereof.

11. The controlled release dosage form of claim 10 wherein the water soluble polymer is hydroxypropylmethylcellulose.

12. The controlled release dosage form of claim 6 wherein the enteric polymer is selected from the group consisting of cellulose acetate phthalate, hydroxypropylmethylcellulose acetate phthalate, hydroxypropylmethylcellulose acetate succinate, carboxymethylethylcellulose, styrene acrylic copolymers, methacrylic copolymers, maleic anhydride copolymers, shellac, and mixtures thereof.

13. The controlled release dosage form of claim 1 wherein the release-controlling layer further comprises a plasticizing agent.

14. The controlled release dosage form of claim 13 wherein the plasticizing agent is selected from the group consisting of esters of phthalic acid, adipic acid, and sebacic acid, ethylene glycol, polyethylene glycol and their derivatives, tricresyl phosphate, castor oil, citrates, triacetin, acetyl glycerides, and mixtures thereof.

15. The controlled release dosage form of claim 14 wherein the plasticizing agent is selected from the group consisting of dibutyl sebacate, dibutyl phthalate and triethyl citrate.

16. The controlled release dosage form of claim 1 wherein the core, the active inner layer, the release-controlling layer and the active overcoat comprise 42–62%, 25–45%, 3.5–13.5% and 2.5–6.5% by weight of the dosage form, respectively.

17. The controlled release dosage form of claim 1 wherein the weight ratio of tacrine in the active inner layer to the active overcoat is in the range from about 12:1 to about 1:1.

18. The controlled release dosage form of claim 17 wherein the weight ratio is in the range from about 10:1 to about 3:1.

19. The controlled release dosage form of claim 18 wherein the weight ratio is in the range from about 8:1 to about 5:1.

20. A process for preparing the controlled release dosage form of claim 1, which comprises:

(a) coating a suitable core with a mixture of tacrine and a binder to obtain a coated pellet;

(b) further coating the pellet obtained in step (a) with a release-controlling-film-forming polymer or a mixture thereof; and (c) further coating the pellet obtained in step (b) with a mixture of tacrine and a binder.

21. A method of treating a subject afflicted with a condition selected from the group consisting of Alzheimer's Disease, pains originating from end-stage cancers, myasthenia gravis, tricyclic anti-depressive agent toxication and tardive dyskinesia, the method comprising administrating to the subject a controlled release tacrine dosage form according to claim 1 in an amount effective to treat the condition.

22. The method according to claim 21, wherein the condition is Alzheimer's Disease.

* * * * *